US009951145B2

(12) United States Patent
Kim et al.

(10) Patent No.: US 9,951,145 B2
(45) Date of Patent: Apr. 24, 2018

(54) CH3 DOMAIN VARIANT PAIR INDUCING FORMATION OF HETERODIMER OF HEAVY CHAIN CONSTANT REGION OF ANTIBODY AT HIGH EFFICIENCY, METHOD FOR PREPARING SAME, AND USE THEREOF

(71) Applicant: AJOU UNIVERSITY INDUSTRY-ACADEMIC COOPERATION FOUNDATION, Suwon-si, Gyeonggi-do (KR)

(72) Inventors: Yong Sung Kim, Suwon-si (KR); Hye Ji Choi, Gumi-si (KR); Eun Sil Sung, Suwon-si (KR)

(73) Assignee: AJOU UNIVERSITY INDUSTRY—ACADEMIC COOPERATION FOUNDATION, Suwon-si (KR)

(*) Notice: Subject to any disclaimer, the term of this patent is extended or adjusted under 35 U.S.C. 154(b) by 112 days.

(21) Appl. No.: 14/647,480

(22) PCT Filed: Nov. 27, 2013

(86) PCT No.: PCT/KR2013/010861
§ 371 (c)(1),
(2) Date: May 27, 2015

(87) PCT Pub. No.: WO2014/084607
PCT Pub. Date: Jun. 5, 2014

(65) Prior Publication Data
US 2015/0307628 A1 Oct. 29, 2015

(30) Foreign Application Priority Data

Nov. 27, 2012 (KR) .................. 10-2012-0135586

(51) Int. Cl.
A61K 39/00 (2006.01)
C07K 16/46 (2006.01)
C07K 16/00 (2006.01)
C07K 16/28 (2006.01)

(52) U.S. Cl.
CPC .......... C07K 16/46 (2013.01); C07K 16/00 (2013.01); C07K 16/2878 (2013.01); C07K 16/468 (2013.01); A61K 2039/505 (2013.01); C07K 2317/31 (2013.01); C07K 2317/526 (2013.01); C07K 2317/622 (2013.01); C07K 2319/30 (2013.01)

(58) Field of Classification Search
CPC ............................................. A61K 2039/505
See application file for complete search history.

(56) References Cited

U.S. PATENT DOCUMENTS

| 5,807,706 | A | 9/1998 | Carter et al. |
| 2010/0286374 | A1 | 11/2010 | Kannan et al. |
| 2011/0054151 | A1 | 3/2011 | Lazar et al. |
| 2012/0149876 | A1* | 6/2012 | Von Kreudenstein . C07K 16/00 530/387.3 |

FOREIGN PATENT DOCUMENTS

| WO | 2009089004 A1 | 7/2009 |
| WO | 2012025530 A1 | 3/2012 |
| WO | 2012032080 A1 | 3/2012 |

OTHER PUBLICATIONS

Choi et al. (PLoS One. Dec. 16, 2015; 10 (12): e0145349; pp. 1-20).*
Choi et al. (Mol Cancer Ther. Dec. 2013; 12 (12): 2748-59).*
Korean Intellectual Property Office, Communication dated Mar. 24, 2015 issued in corresponding Korean application No. 10-2013-0145564.
Merchant AM et al., "An efficient route to human bispecific IgG", Nature Biotechnology 16, 677-681 (1998) doi:10.1038/nbt0798-677.
Moore GL et al., "A novel bispecific antibody format enables simultaneous bivalent and monovalent co-engagement of distinct target antigens", mAbs 3:6, 546-557; Nov./Dec. 2011, Landes Bioscience, DOI: 10.4161/mabs.3.6.18123.
European Patent Office, Communication dated May 12, 2016 issued in corresponding European application No. 13859121.9.
H-J Choi et al, Molecular Cancer Therapeutics, "A Heterodimeric Fc-Based Bispecific Antibody Simultaneously Targeting VEGFR-2 and Met Exhibits Potent Antitumor Activity," vol. 12, No. 12, Oct. 16, 2013, 13 pages in total.
Ridgway et al, Protein Engineering, "'Knobs-into-Holes' engineering of antibody Ch3 domains for heavy chain heterodimerization," vol. 9 No. 7, Jan. 1, 1996, 5 pages in total.
K. Gunasekaran et al, Journal of Biological Chemistry, Enhancing Antibody Fc Heterodimer Formation through Electrostatic Steering Effects: Applications to Bispecific Molecules and Monovalent IgG, vol. 285 No. 25, Jun. 18, 2010, 10 pages in total.
Klein et al, MABS, "Progress in overcoming the chain association issue in bispecific heterodimeric IgG antibodies," vol. 4 No. 6, Nov. 1, 2012, 11 pages in total.

* cited by examiner

Primary Examiner — Stephen Rawlings
(74) Attorney, Agent, or Firm — Sughrue Mion, PLLC

(57) ABSTRACT

Disclosed are a CH3 domain variant pair of an antibody, a method for preparing same, and a use thereof. A mutation is induced in the CH3 domain so as to improve a yield of forming a heterodimer heavy chain constant region of an antibody. The CH3 domain heterodimer forms a heterodimer heavy chain constant region with a high efficiency of 90 to 95% or more and also has outstanding heat stability. A heterodimer heavy chain constant region including the CH3 domain heterodimer can construct a bispecific monoclonal antibody which simultaneously recognizes two kinds of antigens. The CH3 domain heterodimer and the bispecific antibody or fusion protein of an antibody constant region comprising same can be usefully applied to the treatment or prevention of a disease associated with a target antigen or a target protein.

26 Claims, 29 Drawing Sheets

[Fig. 1]
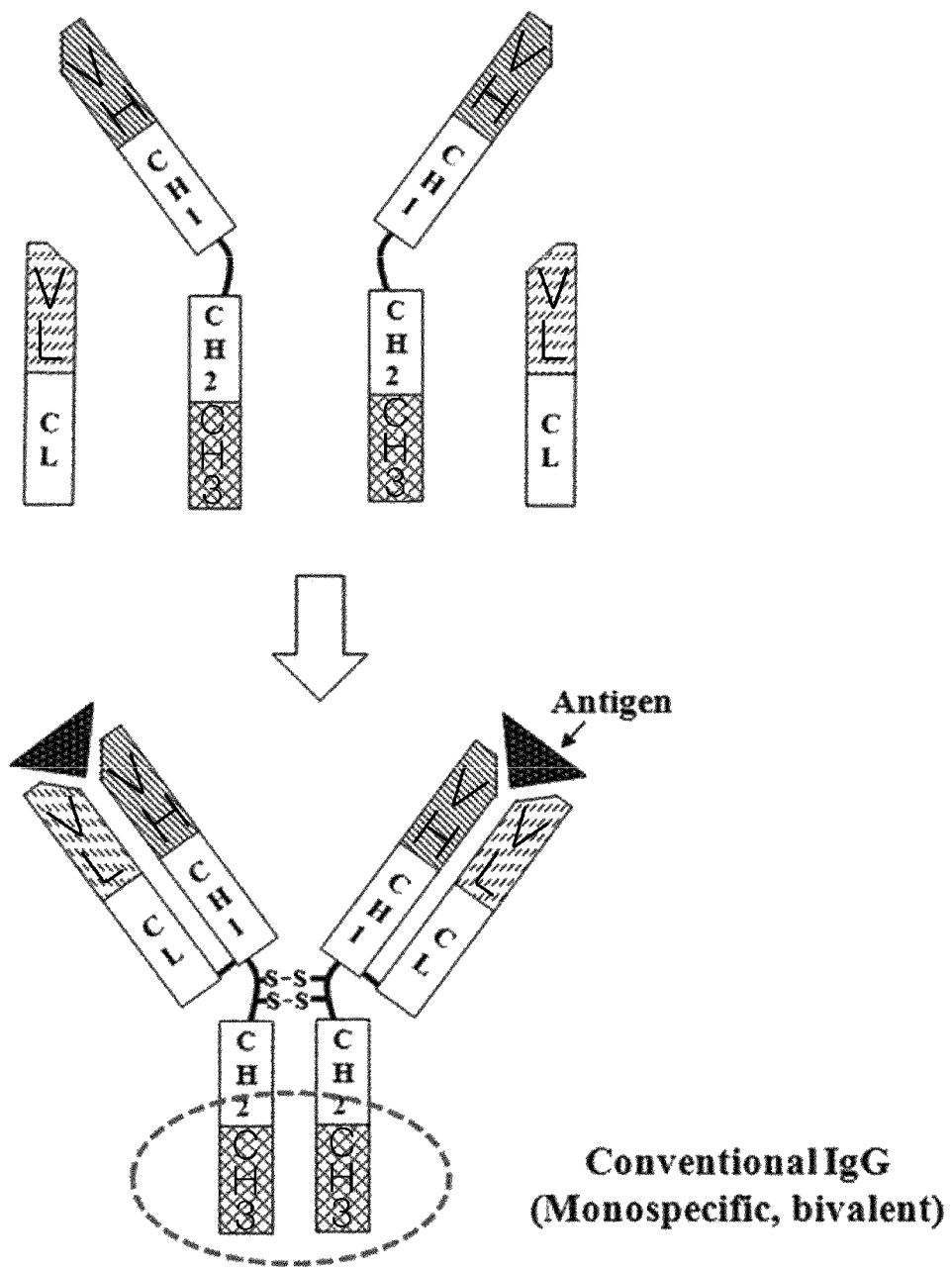

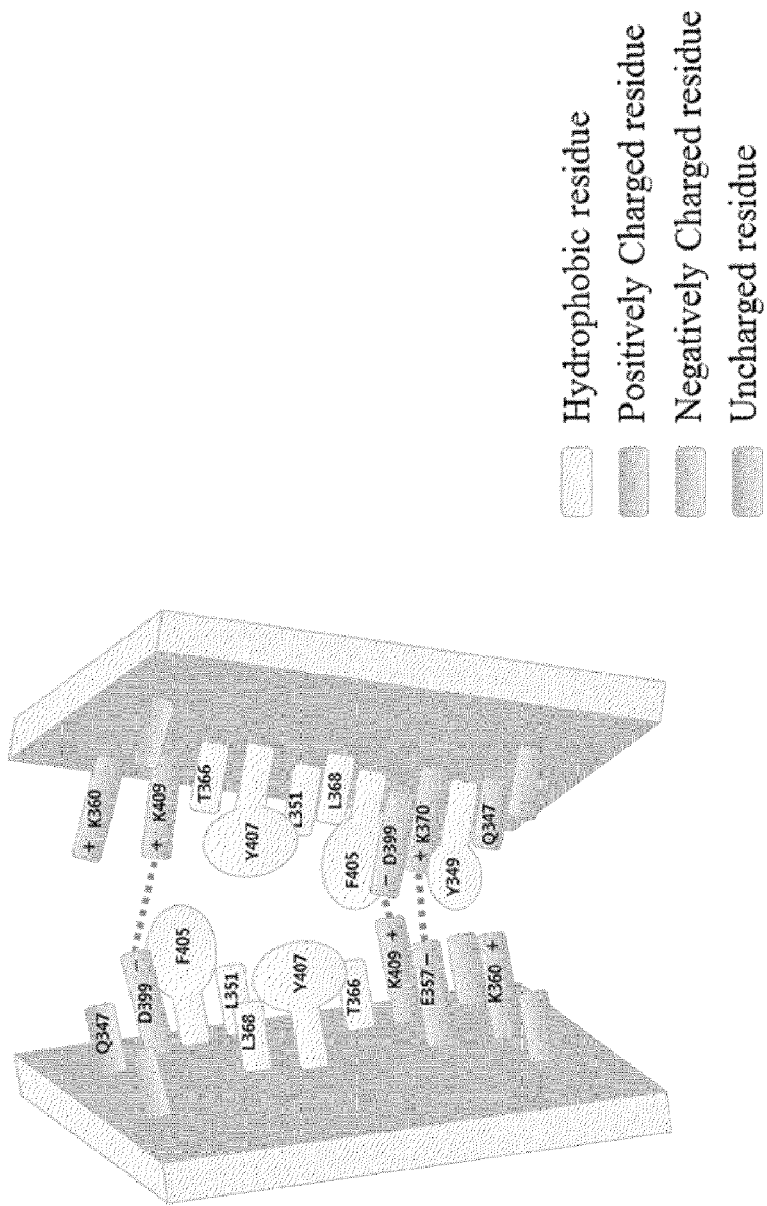
[Fig. 2] Wild type CH3 domain interface

[Fig. 3]
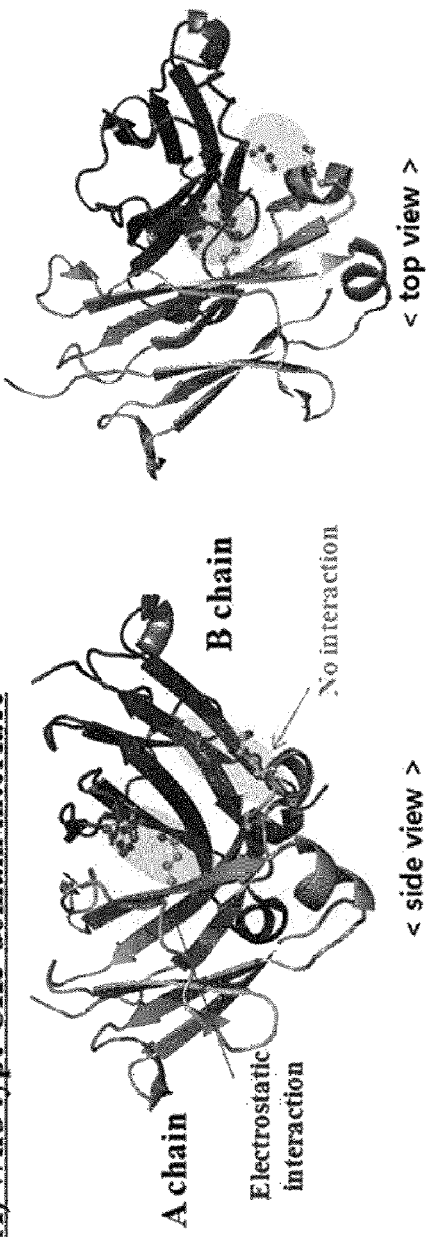
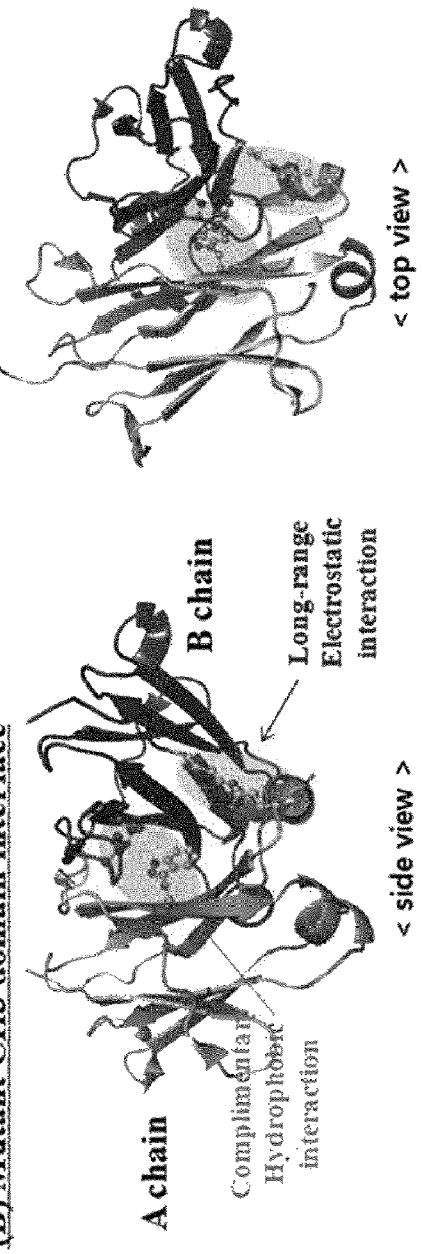

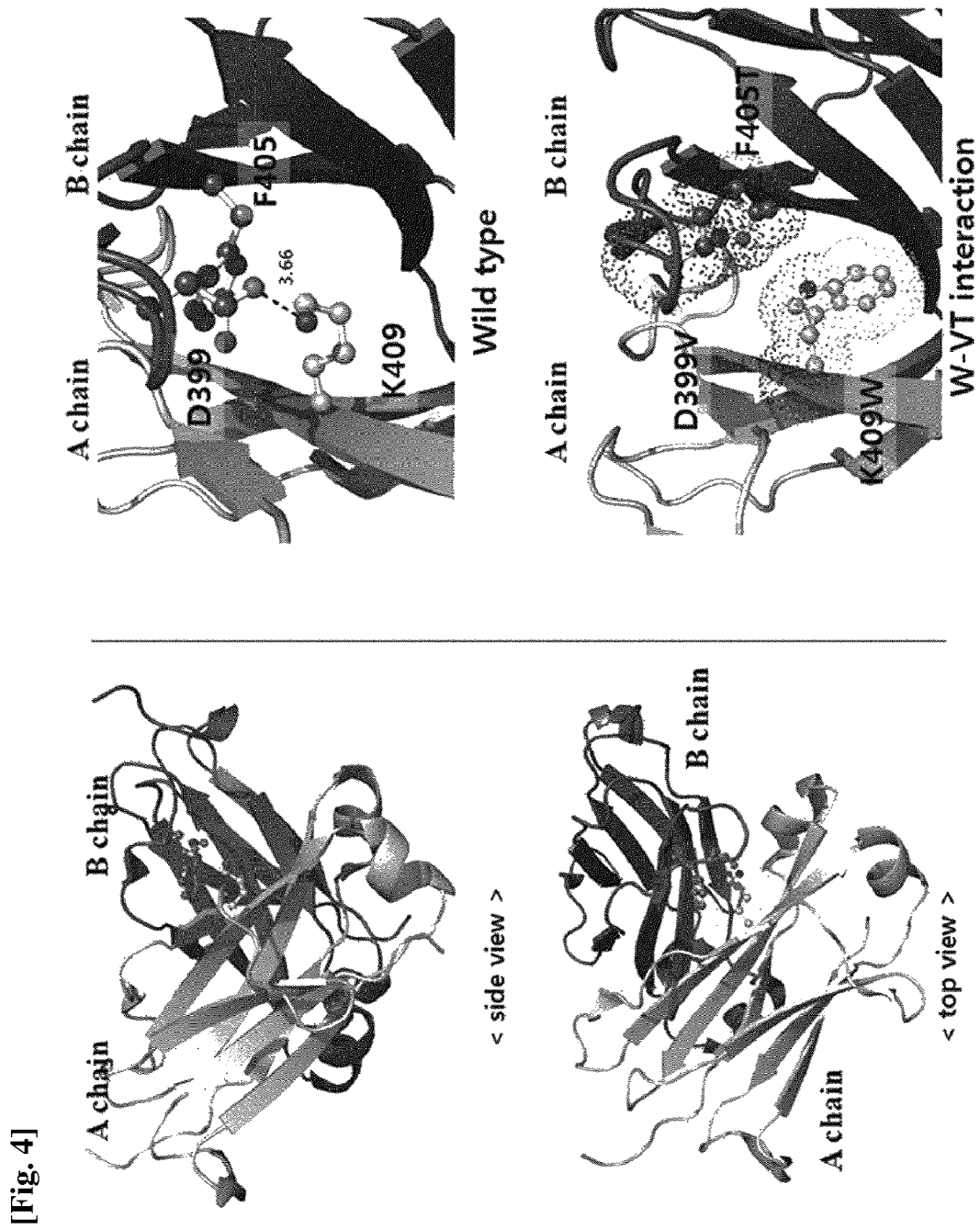
[Fig. 4]

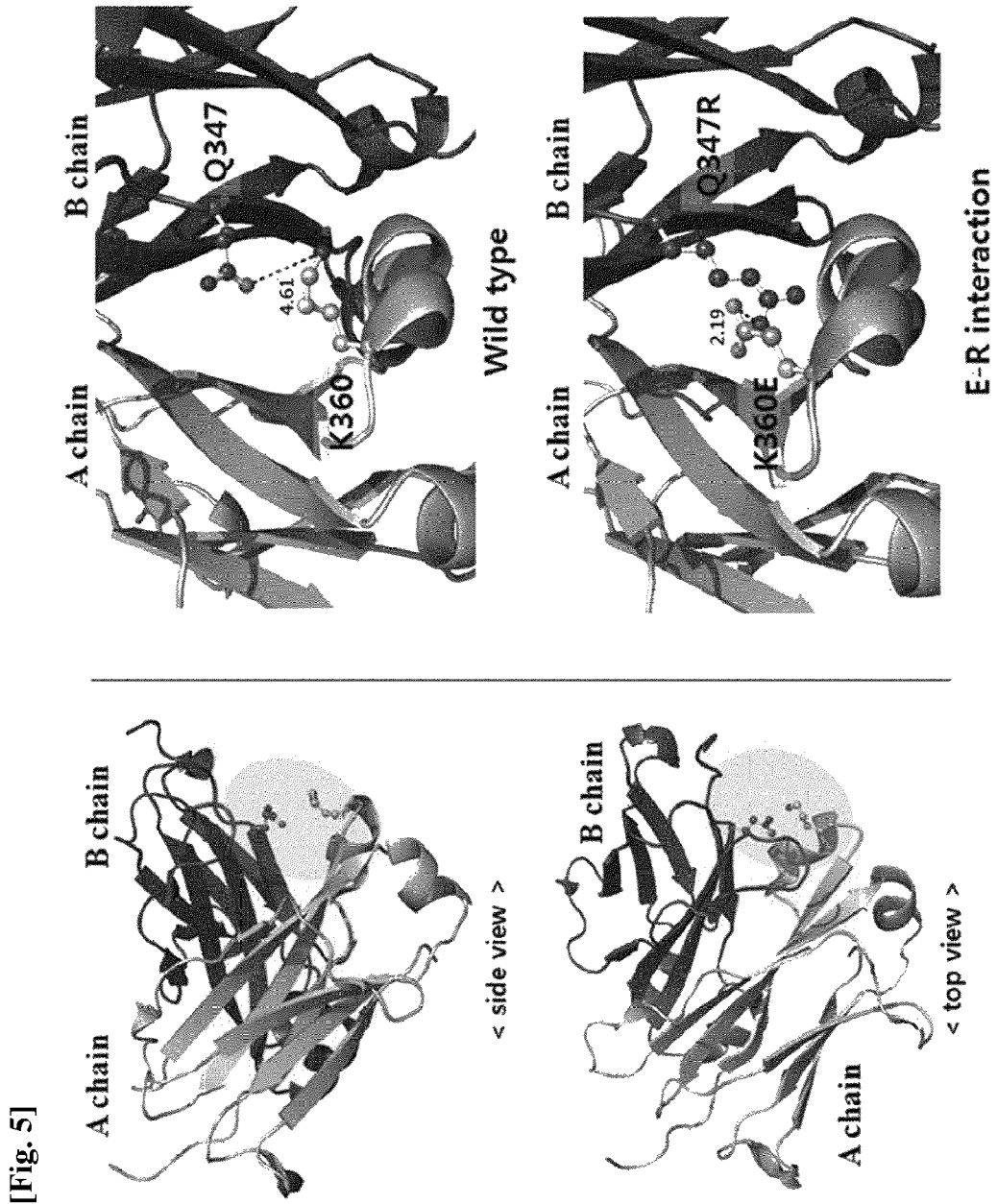
[Fig. 5]

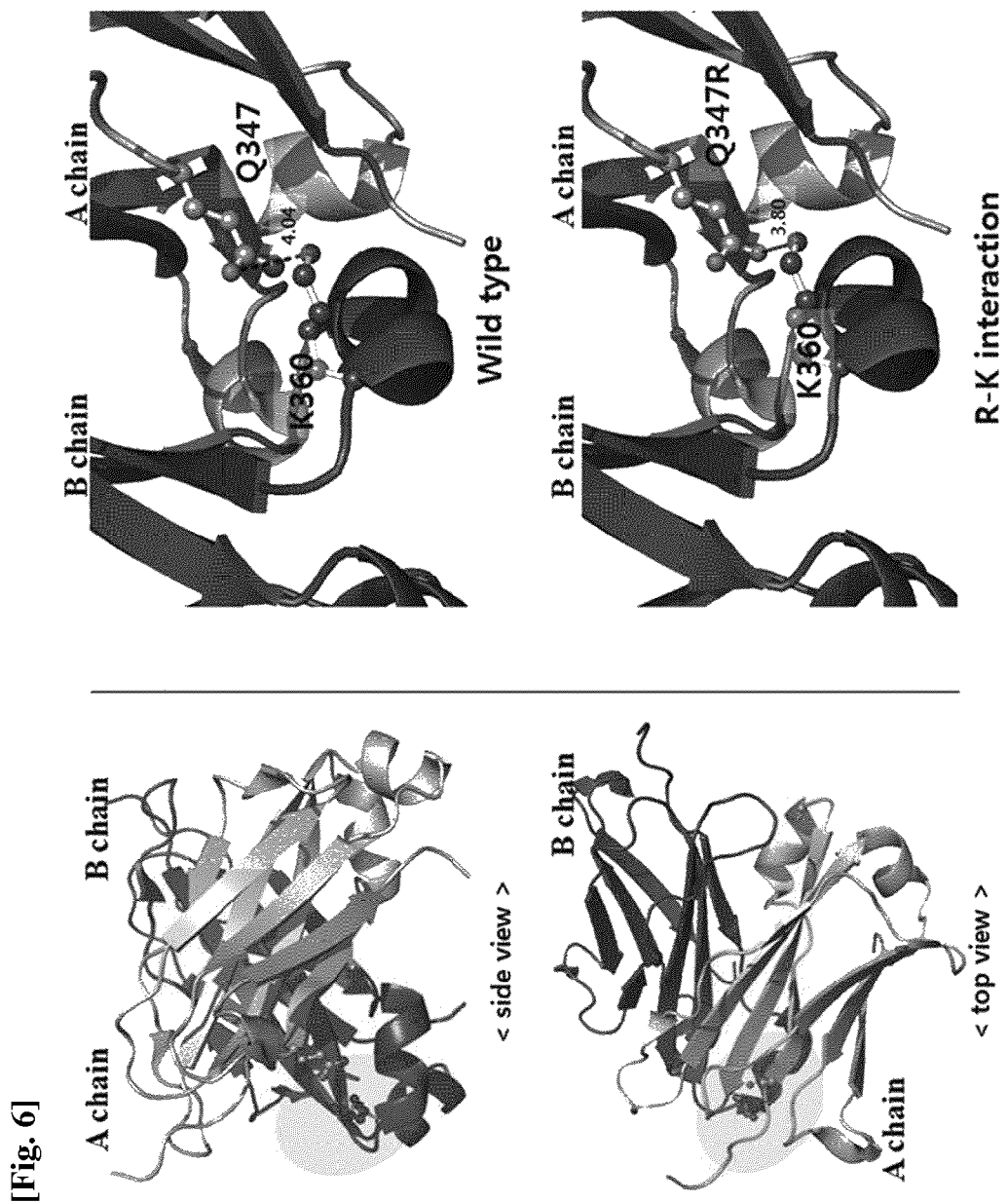

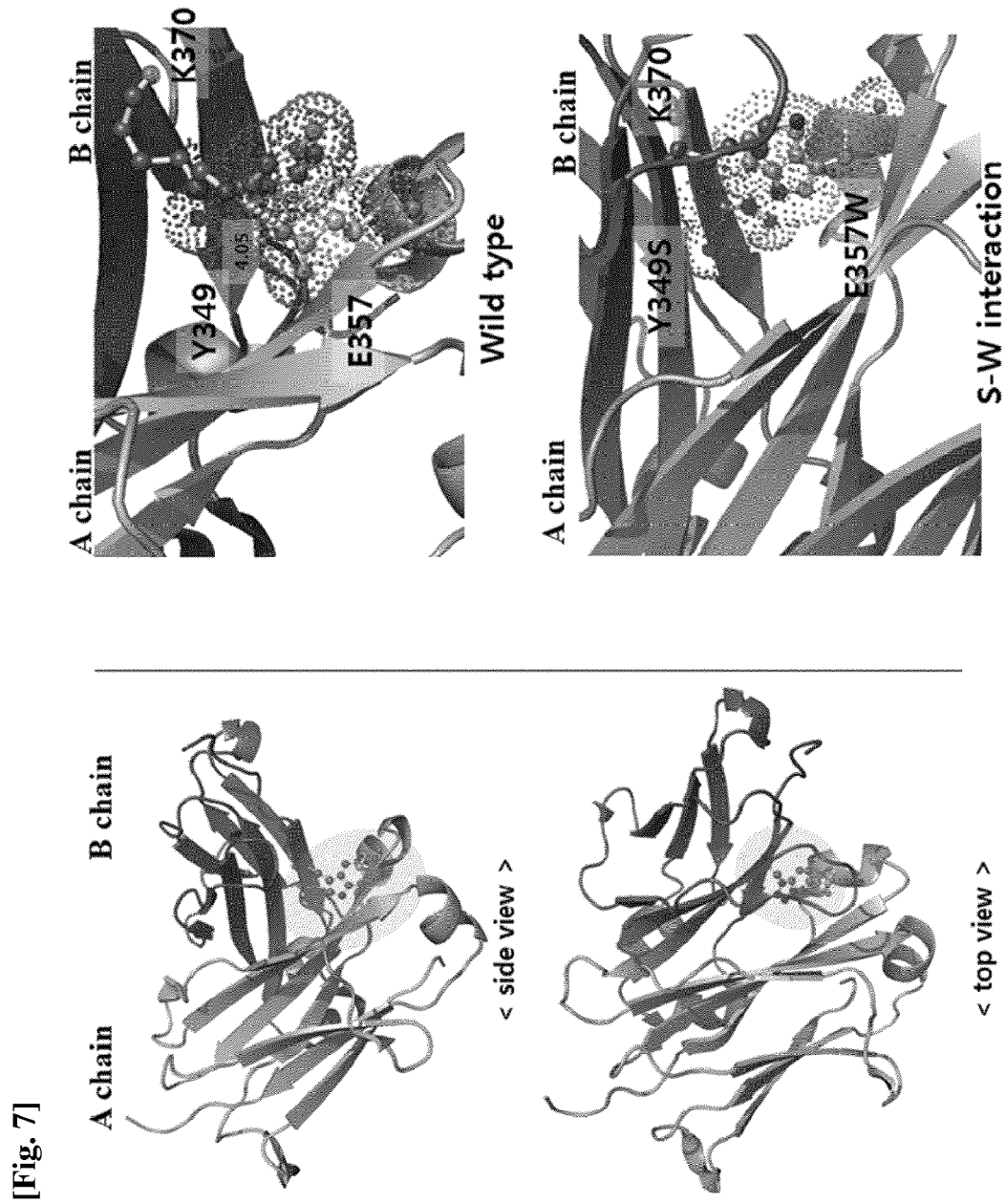
[Fig. 7]

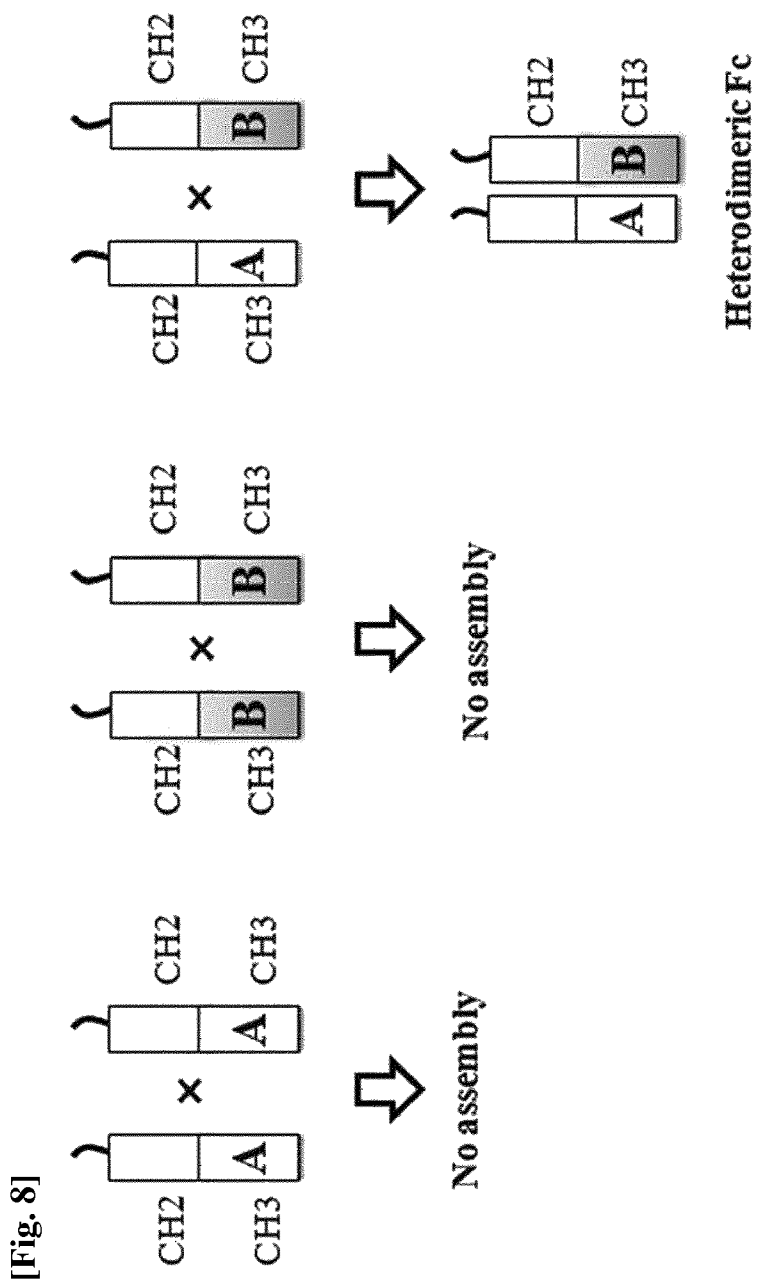

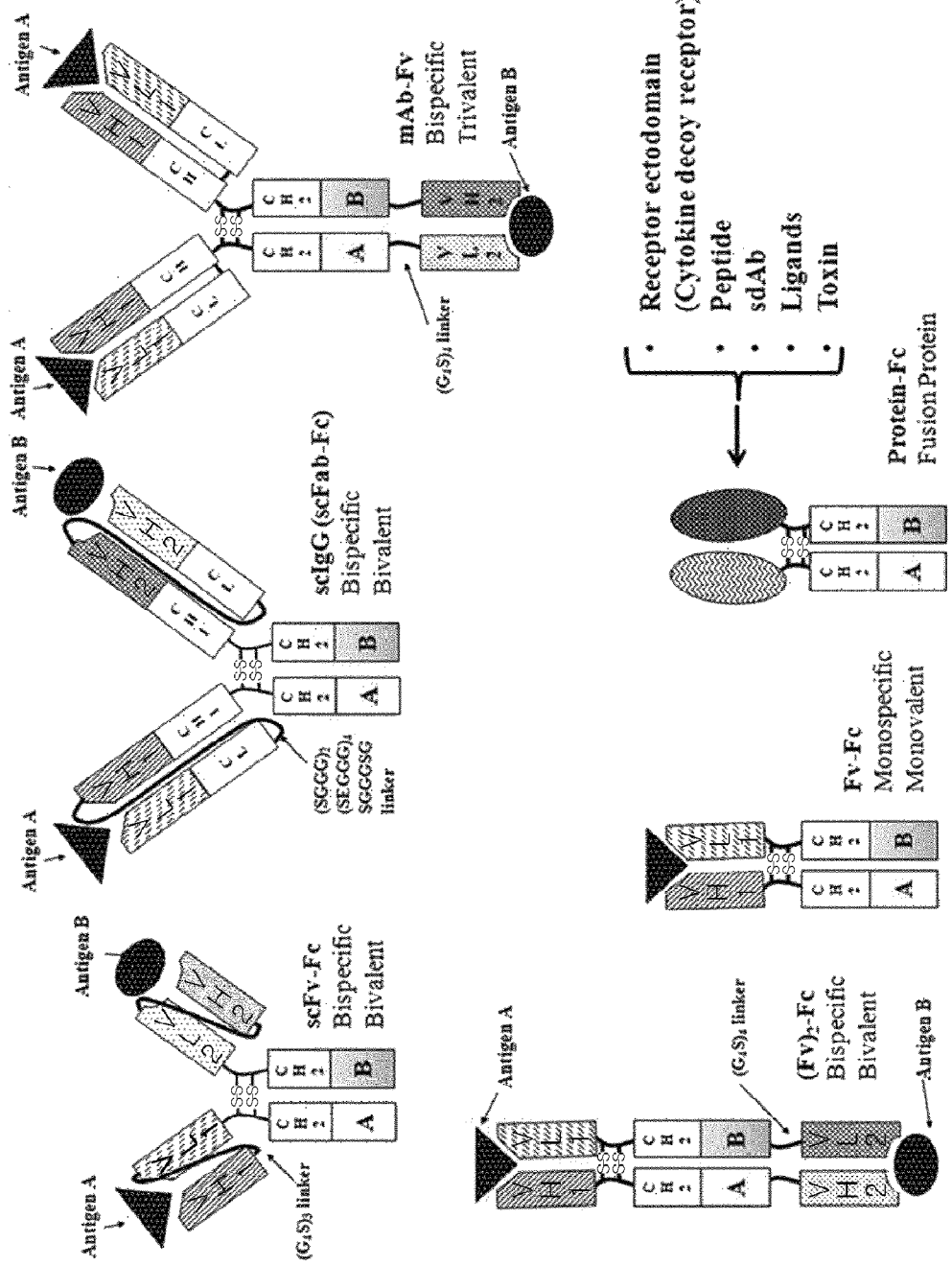
[Fig. 9]

[Fig. 10]

|  | 350 | 360 | 370 | 380 | 390 | 400 |
|---|---|---|---|---|---|---|
| hIgG1 | GQPREPQVYT | LPPSRDELTK | NQVSLTCLVK | GFYPSDIAVE | WESNGQPENN | YKTTPPVLDS |
| hIgG2 | GQPREPQVYT | LPPSREEMTK | NQVSLTCLVK | GFYPSDIAVE | WESNGQPENN | YKTTPPMLDS |
| hIgG3 | GQPREPQVYT | LPPSREEMTK | NQVSLTCLVK | GFYPSDISVE | WESSGQPENN | YNTTPPMLDS |
| hIgG4 | GQPREPQVYT | LPPSQEEMTK | NQVSLTCLVK | GFYPSDIAVE | WESNGQPENN | YKTTPPVLDS |
| mIgG1 | GRPKAPQVYT | IPPPKEQMAK | DKVSLTCMIT | DFFPEDITVE | WQWNGQPAEN | YKNTOPIMNT |
| mIgG2A | GPVRAPQVYV | LPPPAEEMTK | KEFSLTCMIT | GFLPAEIAVD | WTSNGRTEQN | YKNIATVLDS |
| mIgG2B | GLVRAPQVYI | LPPPAEQLSR | KDVSLTCLVV | GFNPGDISVE | WTSNGHTEEN | YKDTAPVLDS |
| mIgG3 | GRAQTPQVYT | IPPPREQMSK | KKVSLTCLVT | NFFSEAISVE | WERNGELEQD | YKNTPPILDS |

|  | 410 | 420 | 430 | 440 | 447 |
|---|---|---|---|---|---|
| hIgG1 | DGSFFLYSKL | TVDKSRWQQG | NVFSCSVMHE | ALHNHYTQKS | LSLSPGK |
| hIgG2 | DGSFFLYSKL | TVDKSRWQQG | NVFSCSVMHE | ALHNHYTQKS | LSLSPGK |
| hIgG3 | DGSFFLYSKL | TVDKSRWQQG | NIFSCSVMHE | ALHNRFTQKS | LSLSPGK |
| hIgG4 | DGSFFLYSRL | TVDKSRWQEG | NVFSCSVMHE | ALHNHYTQKS | LSLSLGK |
| mIgG1 | NGSYFVYSKL | NVQKSNWEAG | NTFTCSVLHE | GLHNHHTEKS | LSHSPGL |
| mIgG2A | DGSYFMYSKL | RVQKSTWERG | SLFACSVVHE | VLHNHLTTKT | ISRSLGK |
| mIgG2B | DGSYFIYSKL | NMKTSKWEKT | DSFSCNVRHE | GLKNYYLKKT | ISRSPGL |
| mIgG3 | DGTYFLYSKL | TVDTDSWLQG | EIFTCSVVHE | ALHNHHTQKN | LSRSPEL |

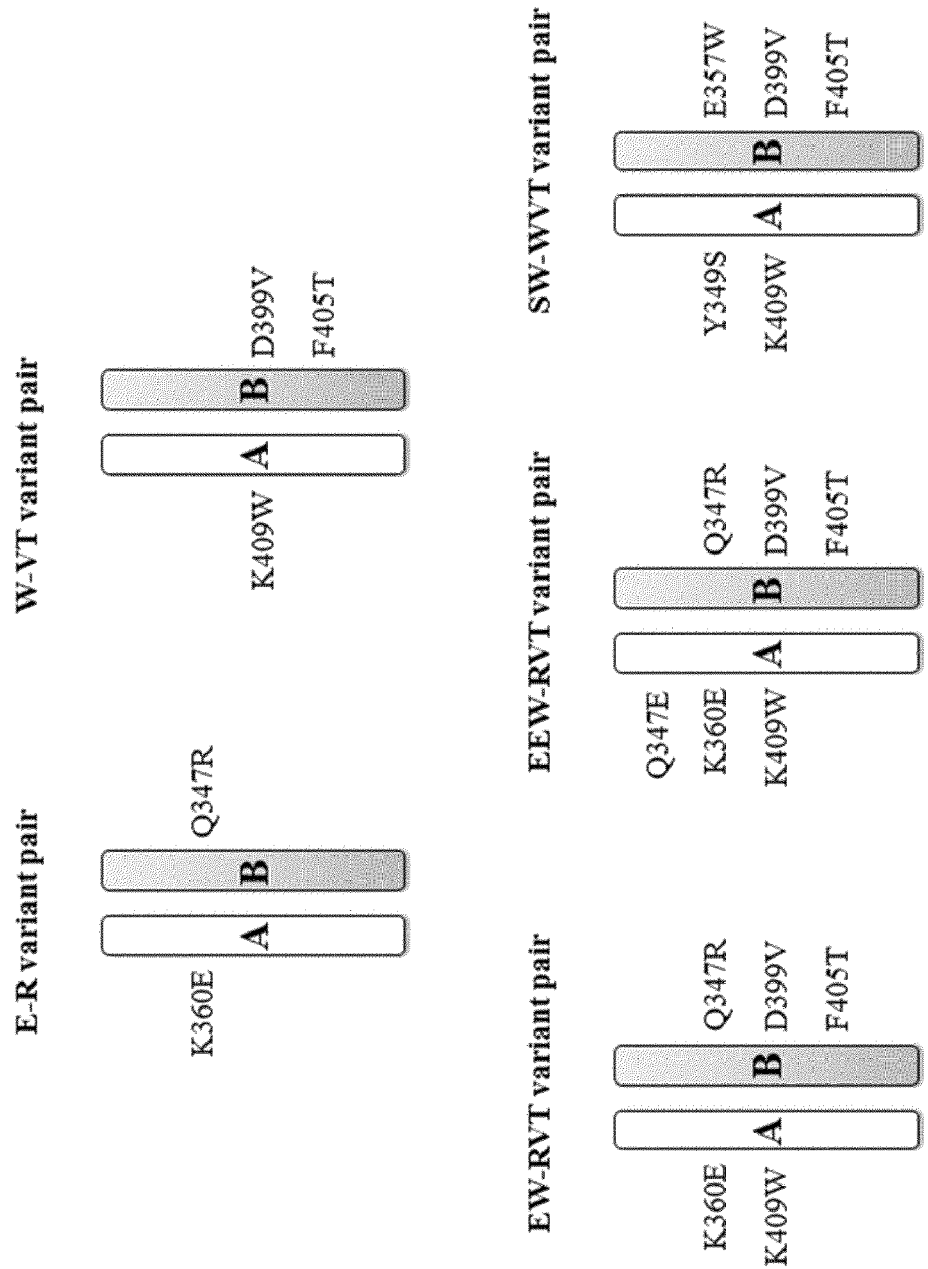
[Fig. 11]

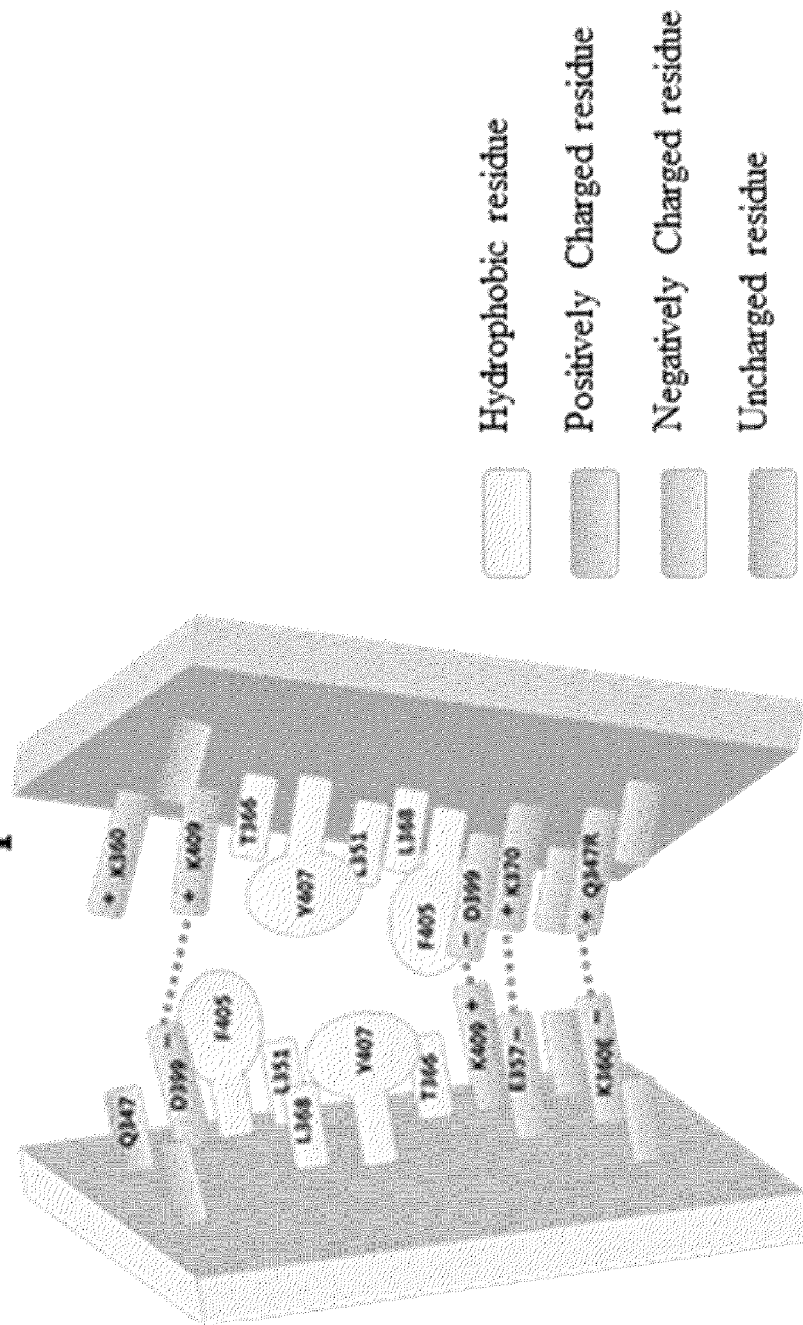

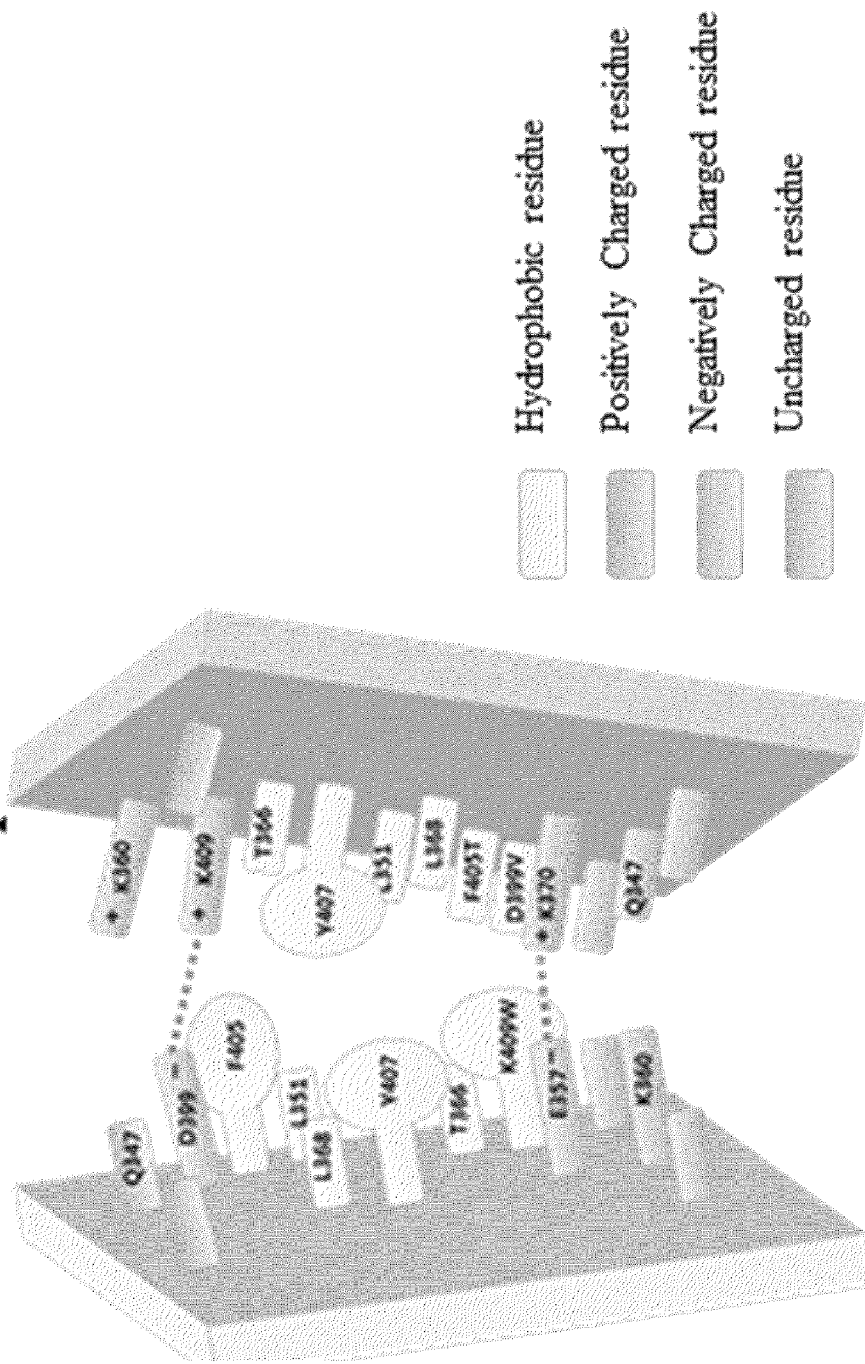
[Fig. 12b]

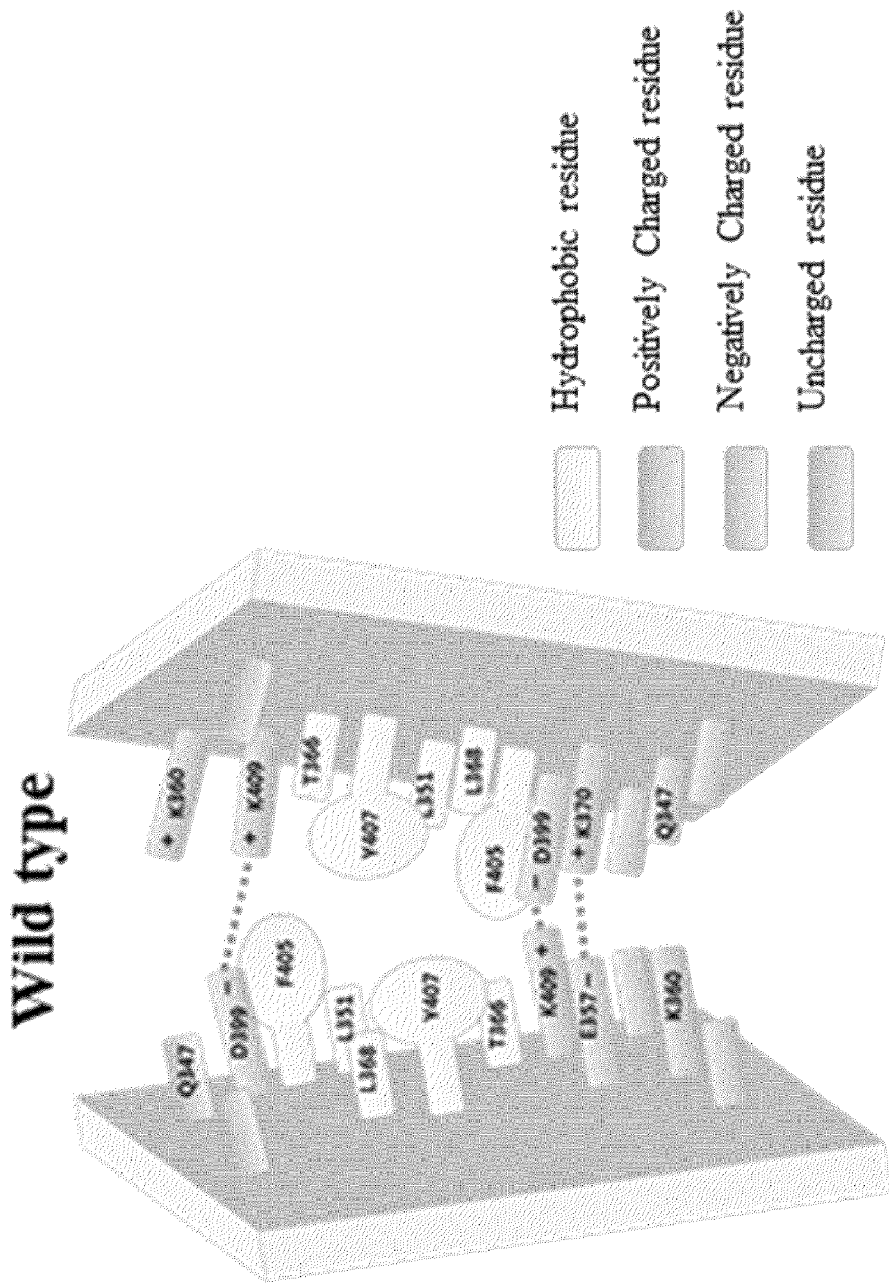
[Fig. 12c]

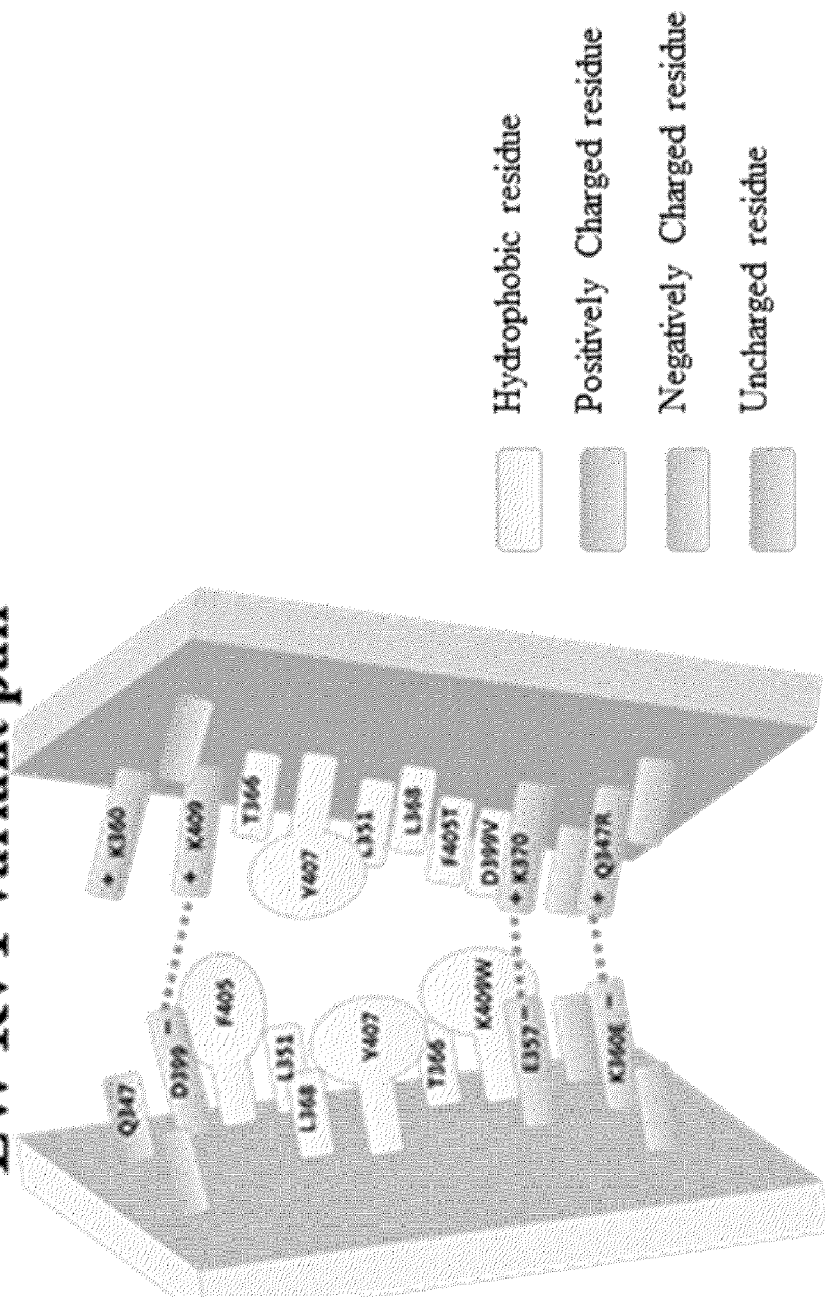

[Fig. 12e]

EEW-RVT variant pair

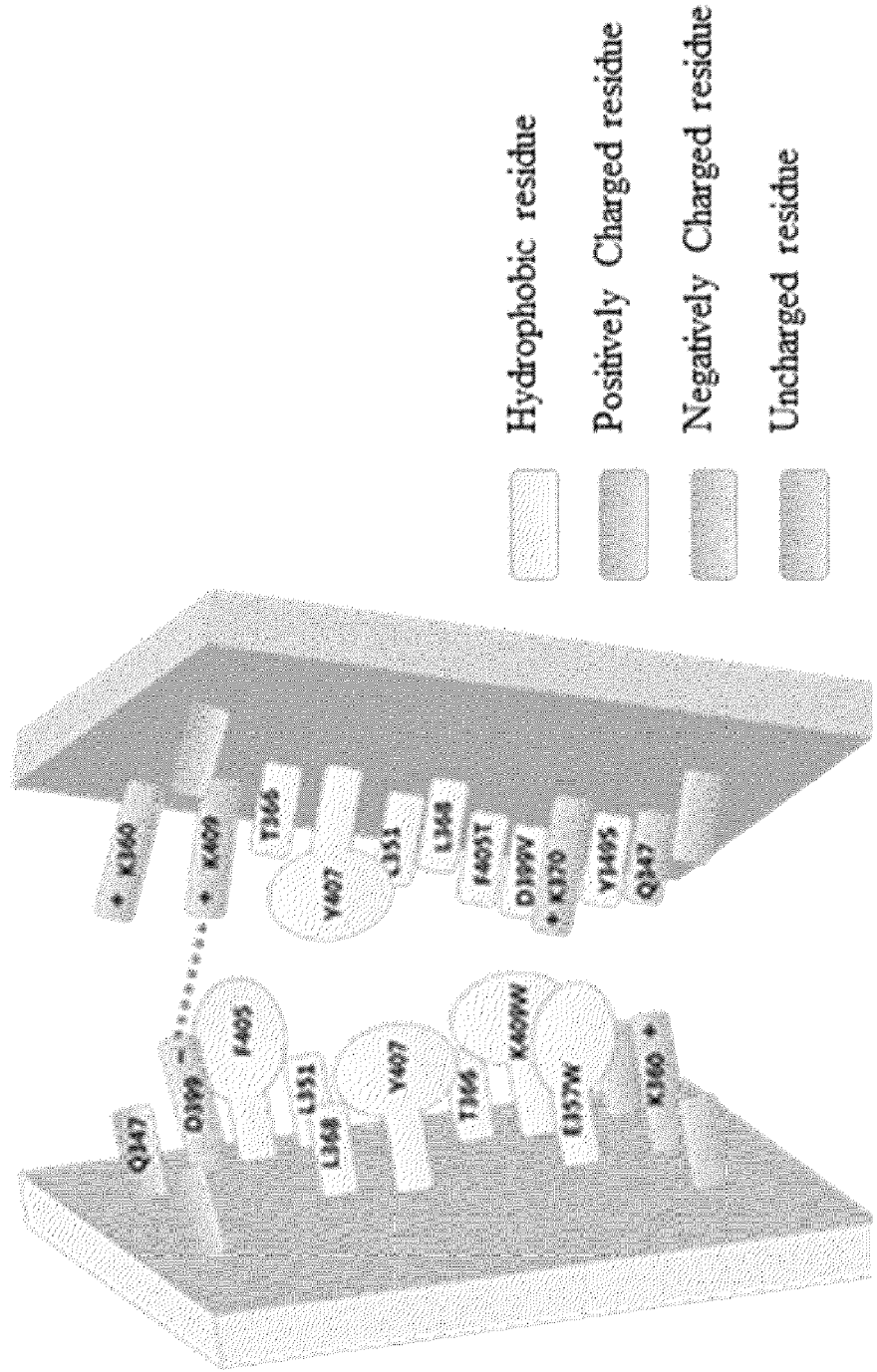
[Fig. 12f]

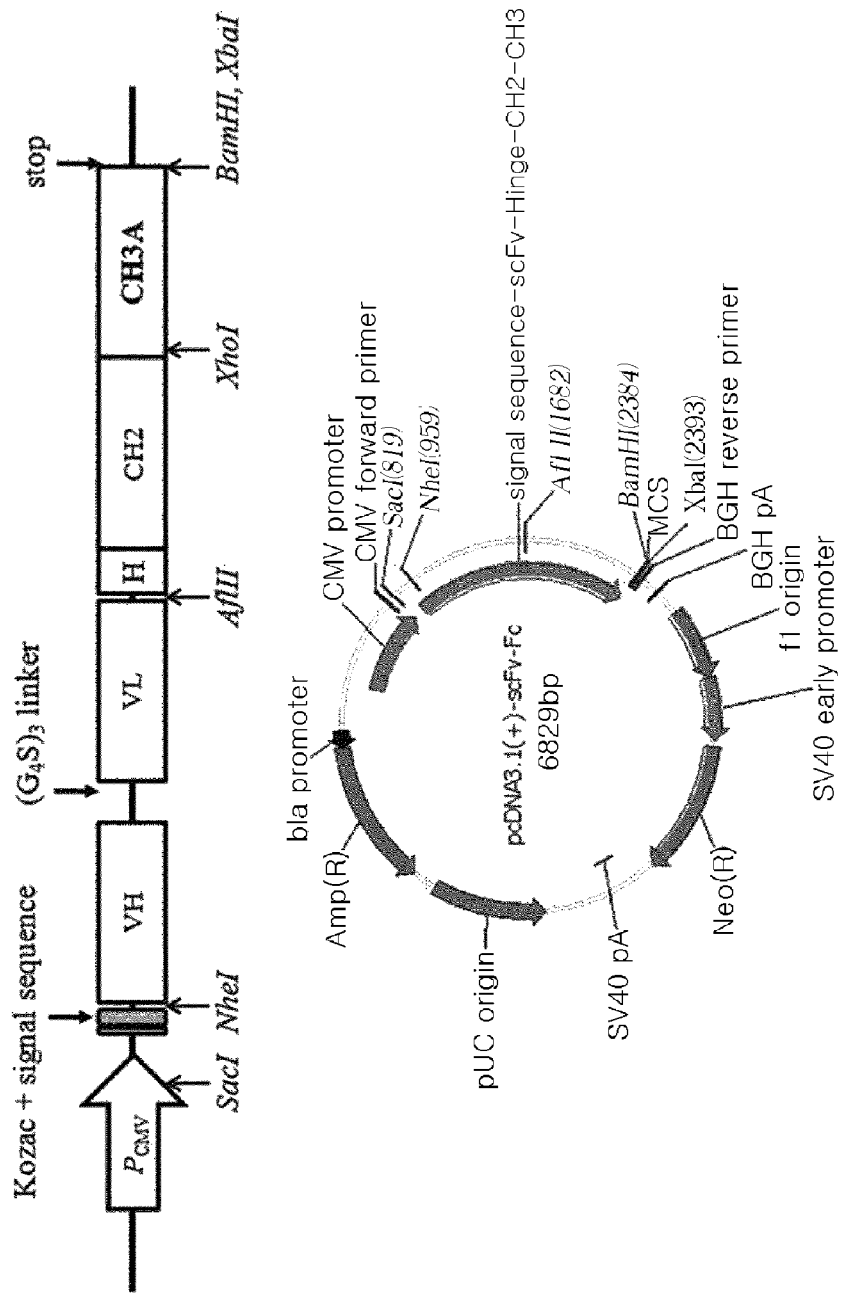
[Fig. 13]
pcDNA3.1(+)-scFv-Fc (CH3 A chain)

[Fig. 14]
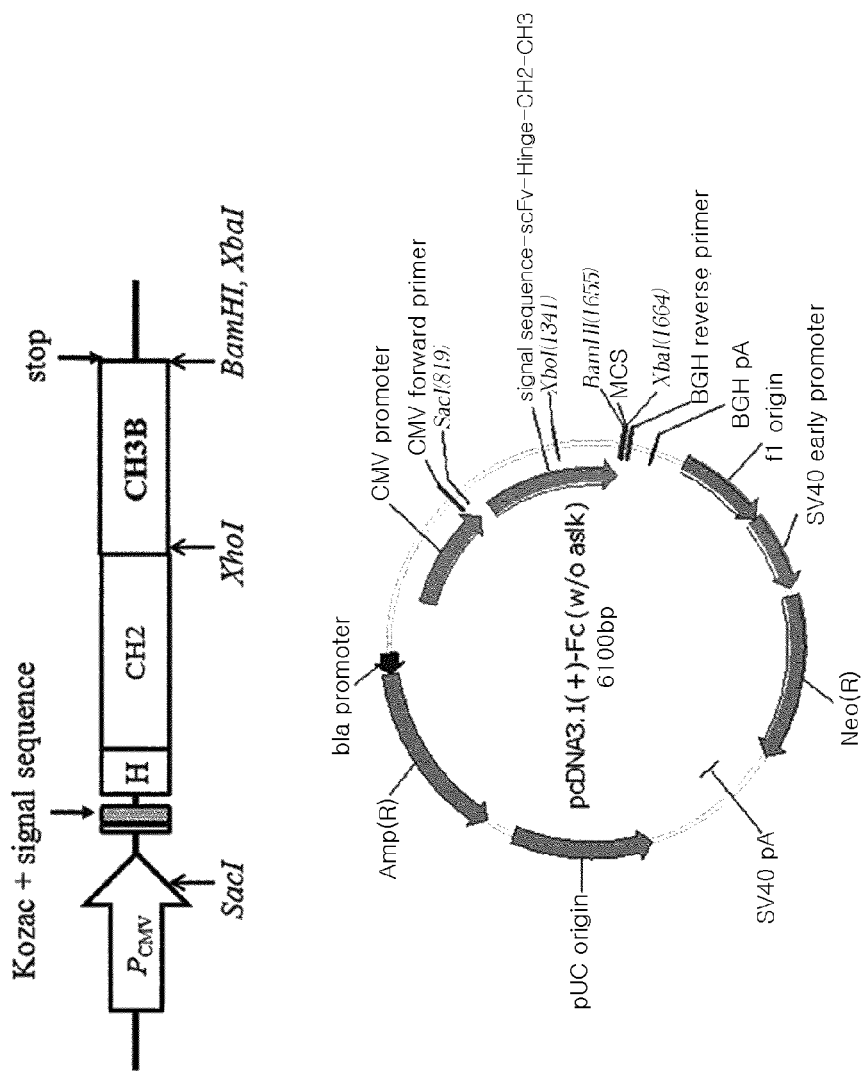

[Fig. 15]
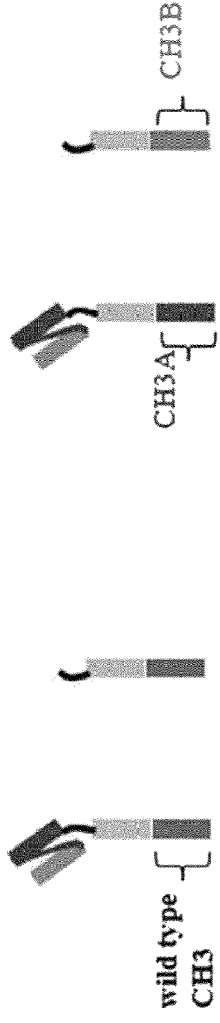
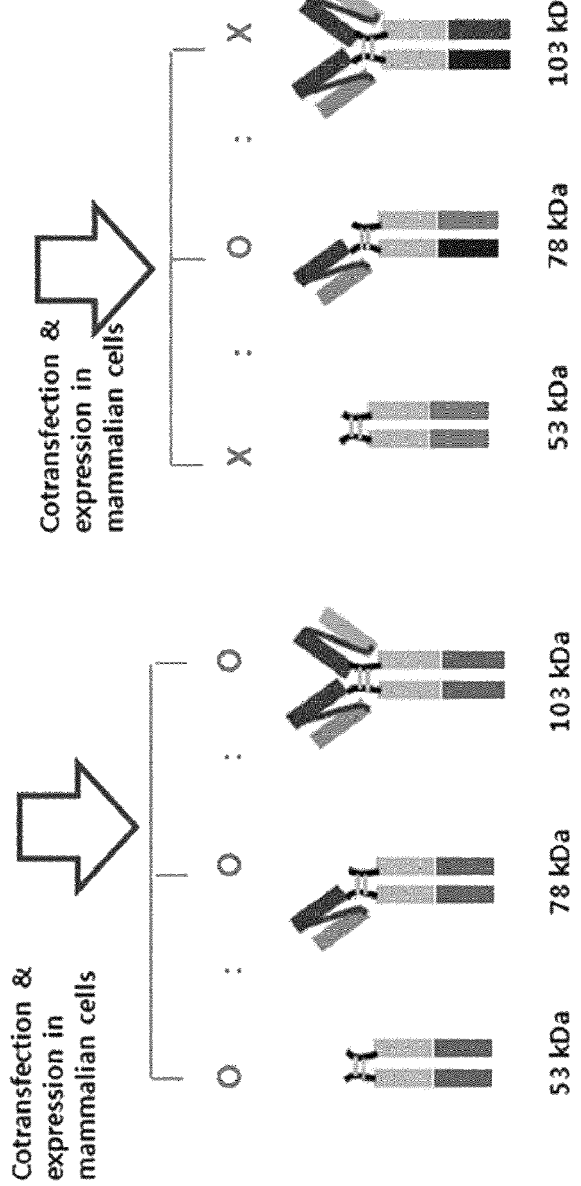

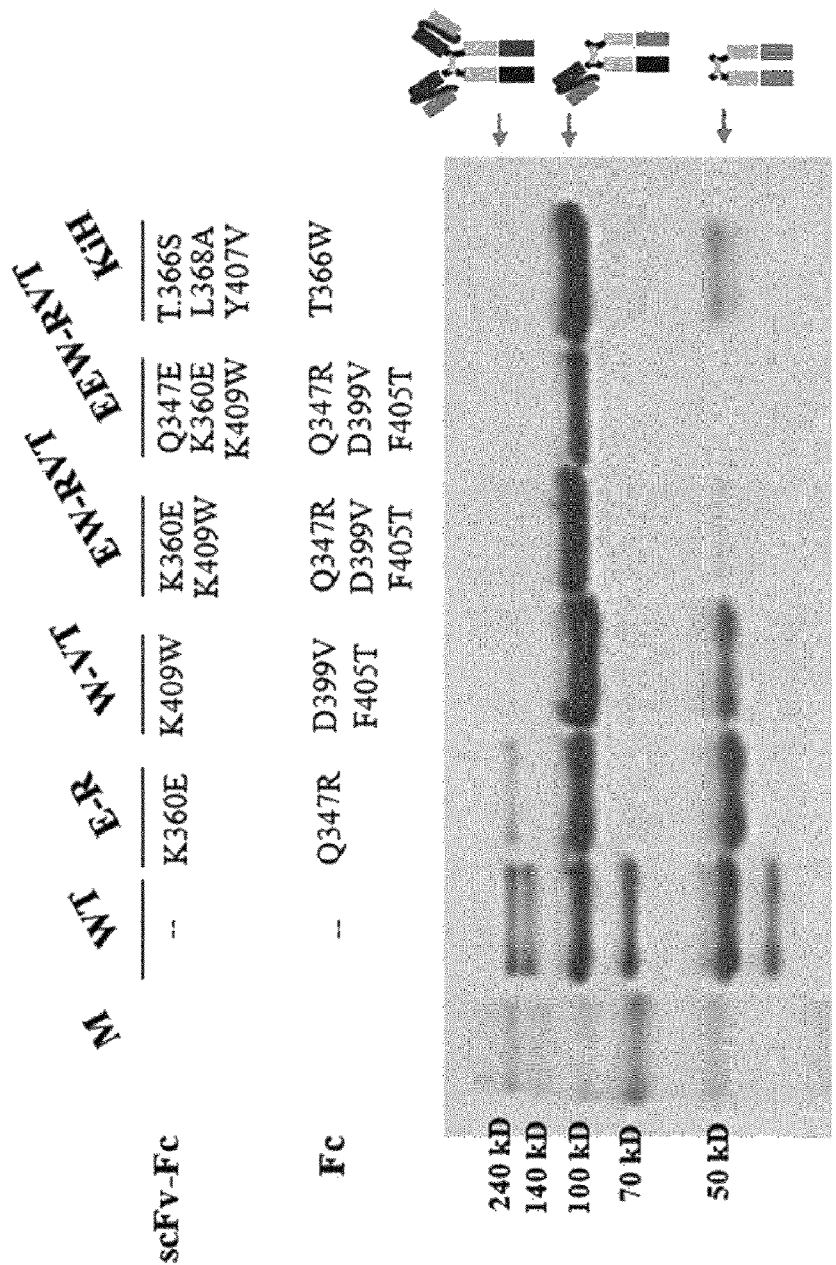
[Fig. 16]
Non-Reducing SDS-PAGE
(purified heterodimer, 10 μg)

[Fig. 17]
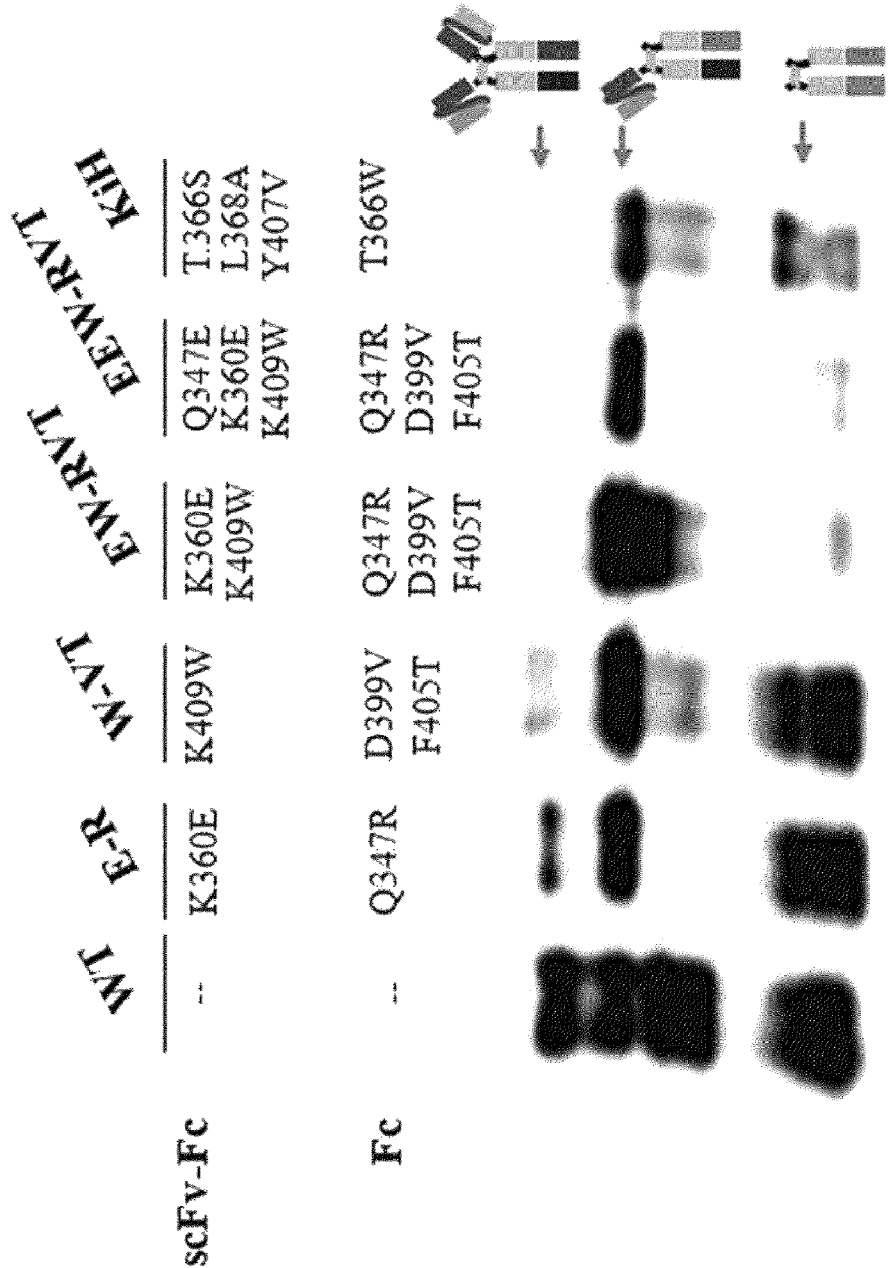

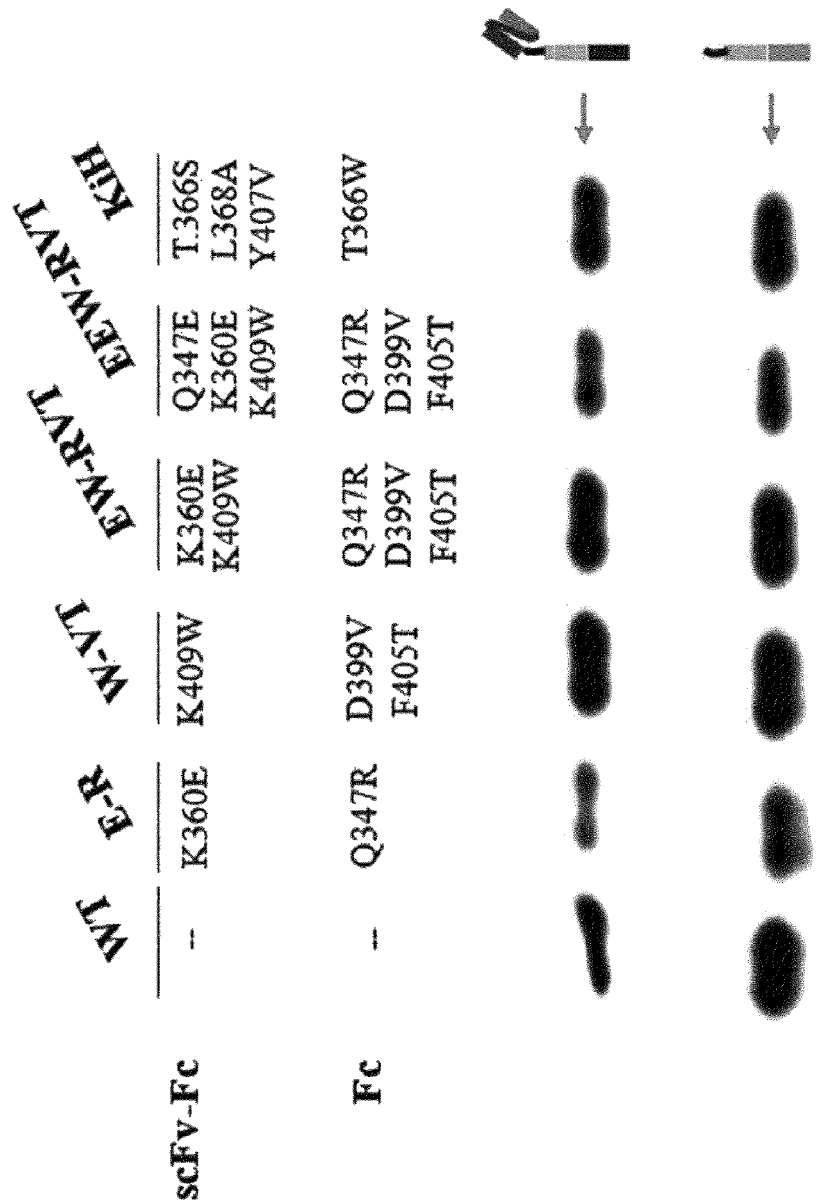
[Fig. 18]

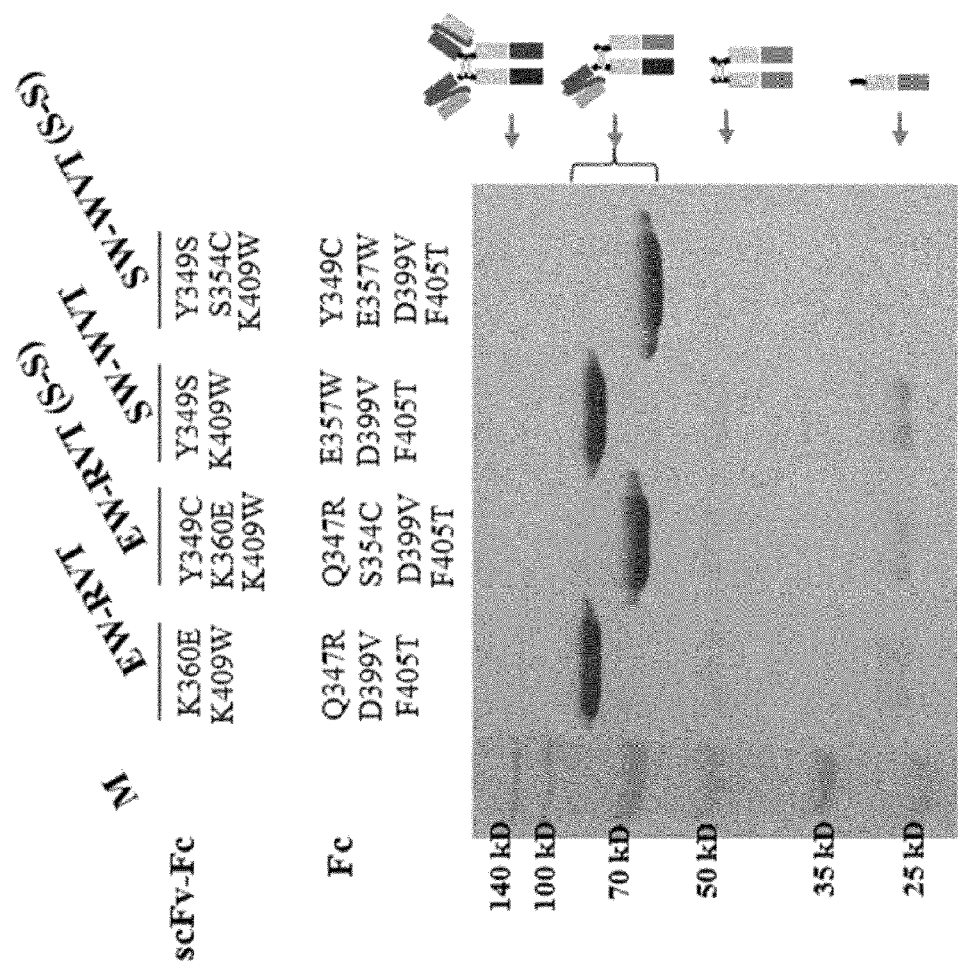
[Fig. 19]

[Fig. 20]
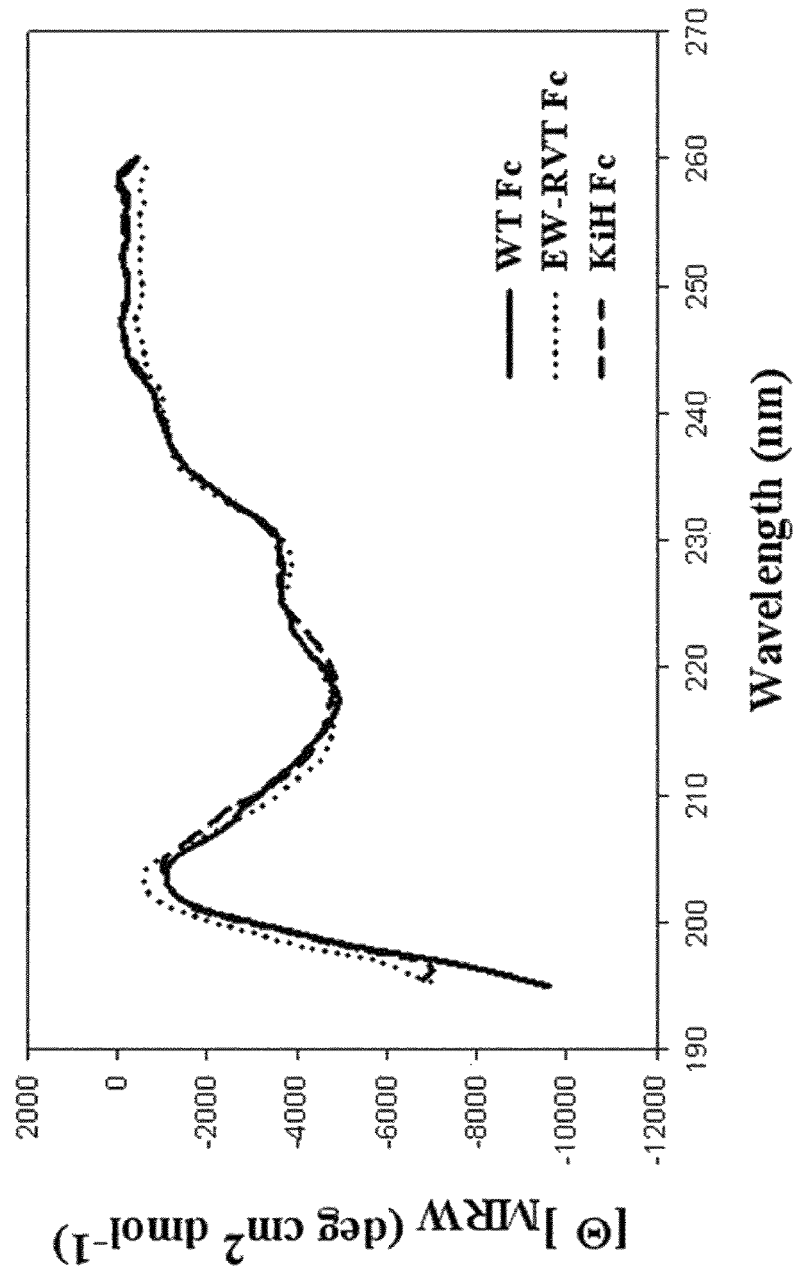

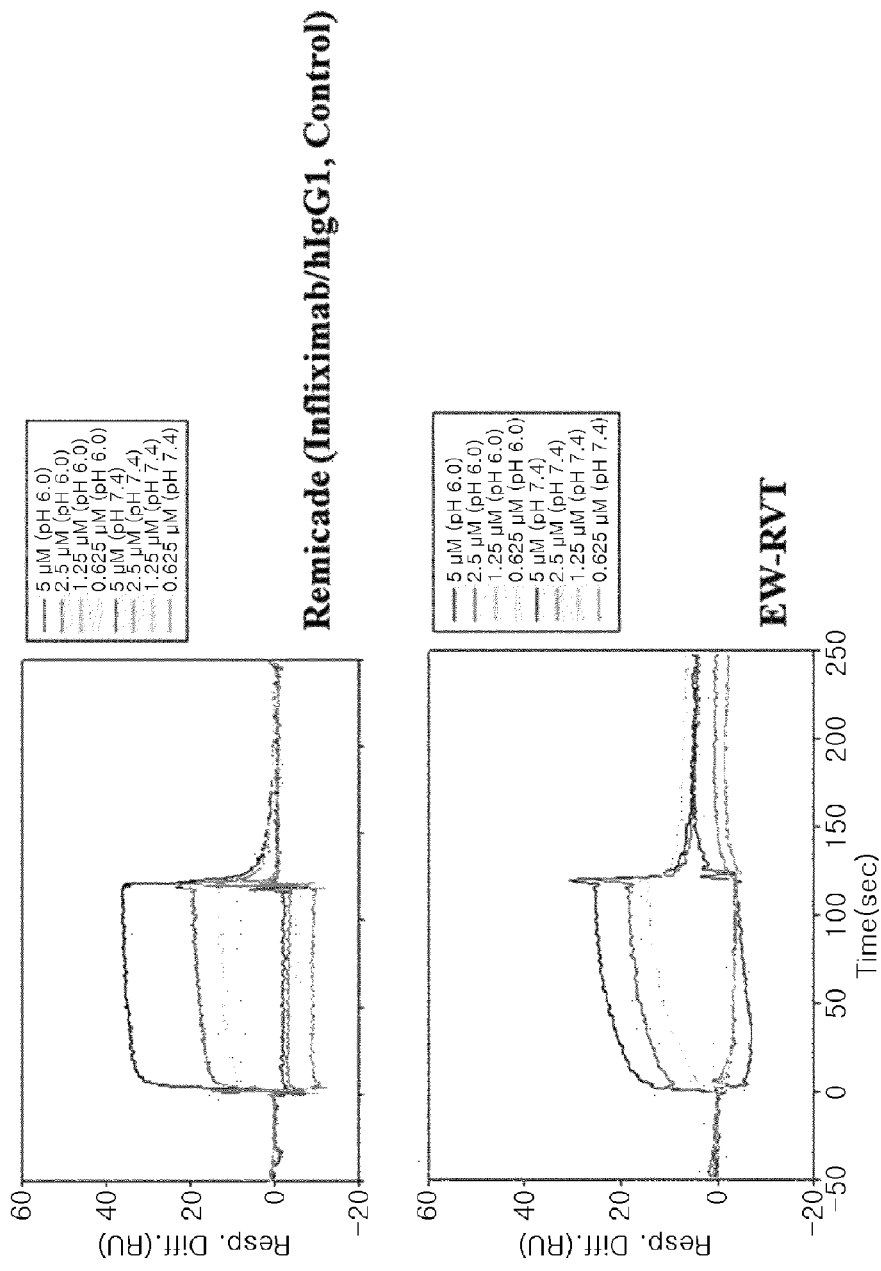

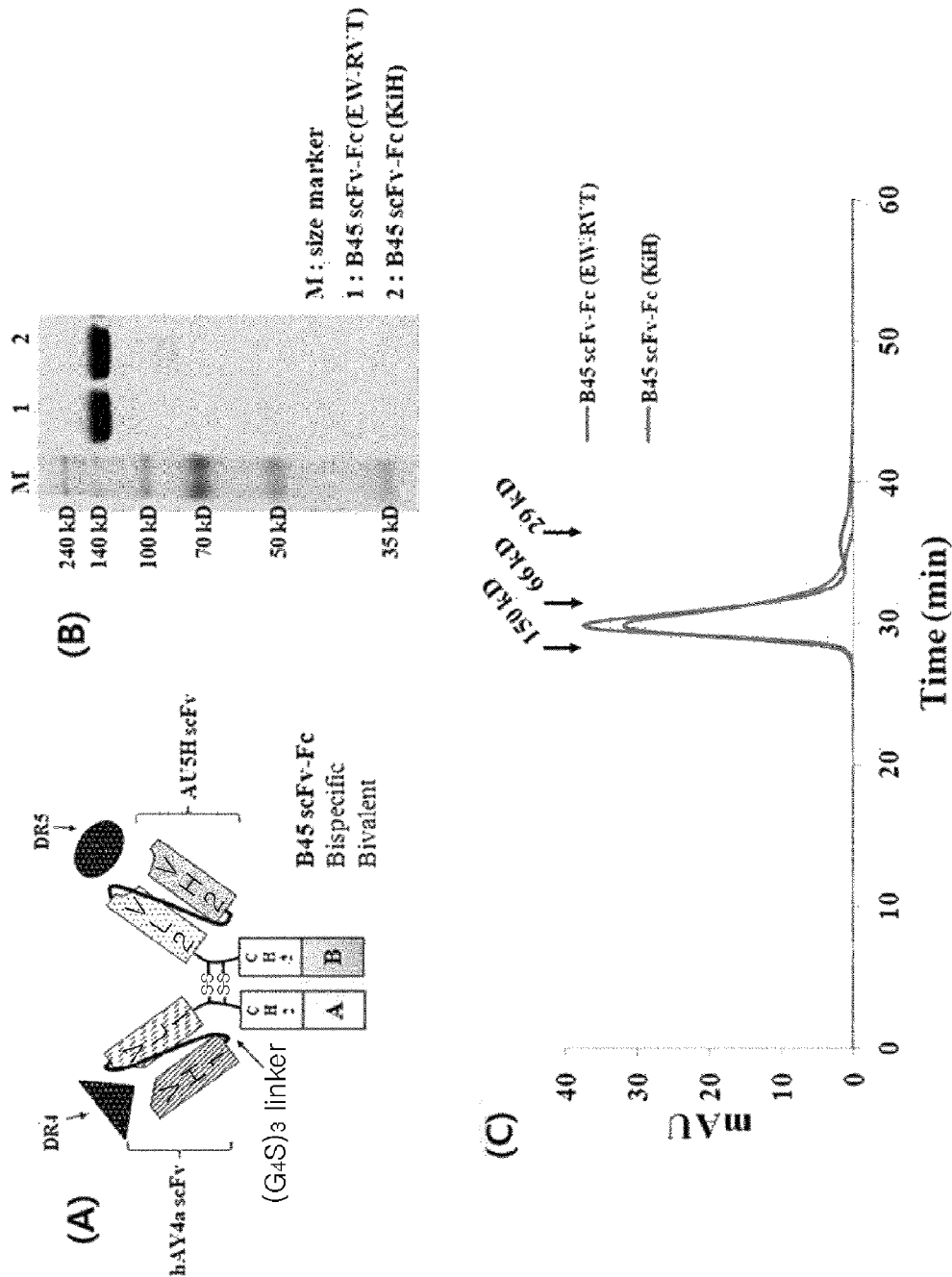

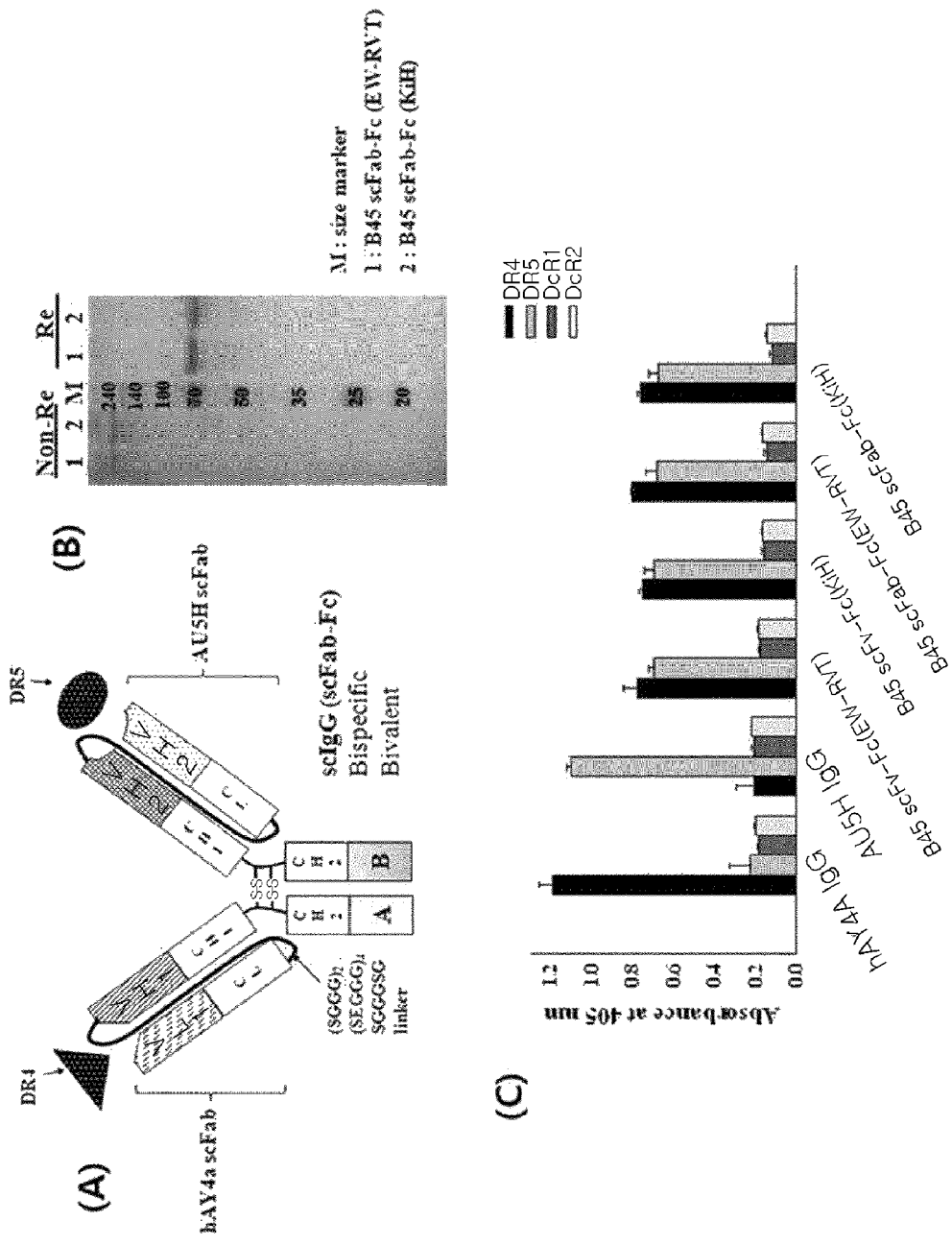

[Fig. 24]
HCT116
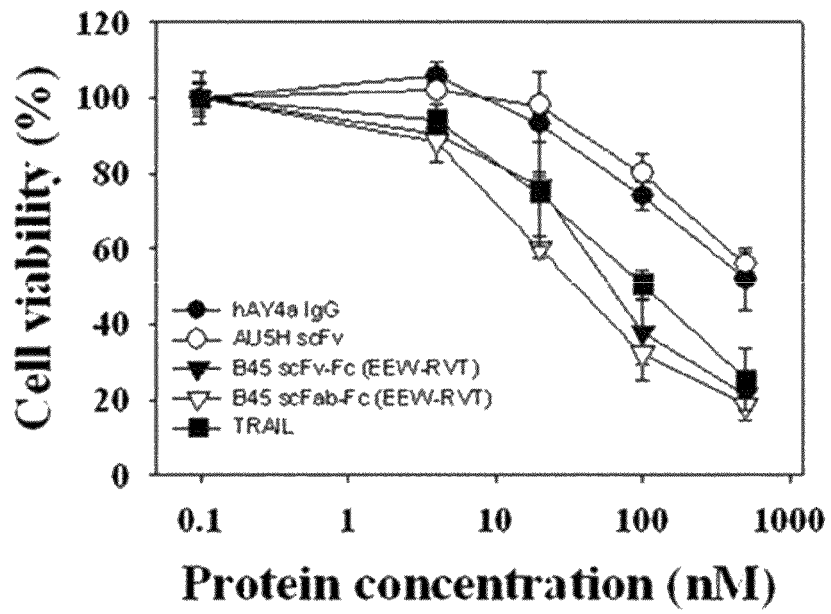
HeLa
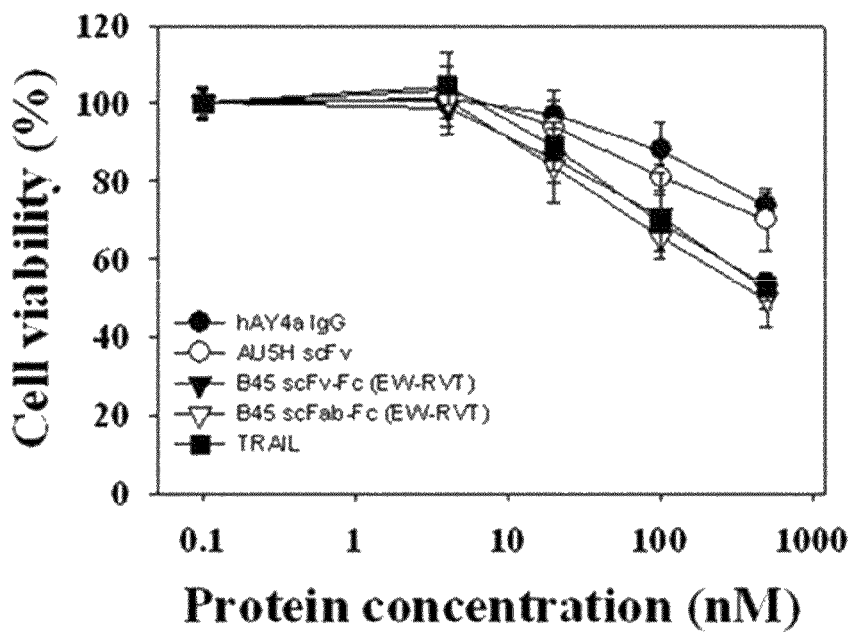

SEQUENCE LISTING

<160> NUMBER OF SEQ ID NOS: 36

<210> SEQ ID NO 1
<211> LENGTH: 107
<212> TYPE: PRT
<213> ORGANISM: Artificial Sequence

```
<220> FEATURE:
<223> OTHER INFORMATION: Synthetic construct of Wild type CH3A
      (EU numbering 341-447)

<400> SEQUENCE: 1

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Synthetic construct of Wild type CH3B
      (EU numbering 341-447)

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Synthetic construct of E-R CH3A (EU numbering
      341-447)

<400> SEQUENCE: 3

Gly Gln Pro Arg Glu Pro Gln Val Tyr Thr Leu Pro Pro Ser Arg Asp
1               5                   10                  15

Glu Leu Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

Asn Asn Tyr Lys Thr Thr Pro Pro Val Leu Asp Ser Asp Gly Ser Phe
            50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Synthetic construct of E-R CH3B (EU numbering
      341-447)

<400> SEQUENCE: 4

Gly Gln Pro Arg Glu Pro Arg Val Tyr Thr Leu Pro Pro Ser Arg Asp
  1               5                  10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                 70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Synthetic construct of W-VT CH3A (EU numbering
      341-447)

<400> SEQUENCE: 5

Gly Gln Pro Arg Glu Pro Gln Val Tyr Thr Leu Pro Pro Ser Arg Asp
  1               5                  10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Trp Leu Thr Val Asp Lys Ser Arg Trp Gln Gln Gly
 65                 70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

-continued

<210> SEQ ID NO 6
<211> LENGTH: 107
<212> TYPE: PRT
<213> ORGANISM: Artificial Sequence
<220> FEATURE:
<223> OTHER INFORMATION: Synthetic construct of W-VT CH3B (EU numbering
      341-447)

<400> SEQUENCE: 6

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Synthetic construct of EW-RVT CH3A
      (EU numbering 341-447)

<400> SEQUENCE: 7

Gly Gln Pro Arg Glu Pro Gln Val Tyr Thr Leu Pro Pro Ser Arg Asp
 1               5                  10                  15

Glu Leu Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Trp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Synthetic construct of EW-RVT CH3B
      (EU numbering 341-447)

<400> SEQUENCE: 8

Gly Gln Pro Arg Glu Pro Arg Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Synthetic construct of EW-RVT (S-S) CH3A
      (EU numbering 341-447)

<400> SEQUENCE: 9

Gly Gln Pro Arg Glu Pro Gln Val Cys Thr Leu Pro Pro Ser Arg Asp
 1               5                  10                  15

Glu Leu Thr Glu Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Synthetic construct of EW-RVT (S-S) CH3B
      (EU numbering 341-447)

<400> SEQUENCE: 10

Gly Gln Pro Arg Glu Pro Arg Val Tyr Thr Leu Pro Pro Cys Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

```
<210> SEQ ID NO 11
<211> LENGTH: 107
<212> TYPE: PRT
<213> ORGANISM: Artificial Sequence
<220> FEATURE:
<223> OTHER INFORMATION: Synthetic construct of EEW-RVT CH3A
      (EU numbering 341-447)

<400> SEQUENCE: 11
```

| Gly | Gln | Pro | Arg | Glu | Pro | Glu | Val | Tyr | Thr | Leu | Pro | Pro | Ser | Arg | Asp |
|---|---|---|---|---|---|---|---|---|---|---|---|---|---|---|---|
| 1 | | | | 5 | | | | | 10 | | | | | 15 | |

| Glu | Leu | Thr | Glu | Asn | Gln | Val | Ser | Leu | Thr | Cys | Leu | Val | Lys | Gly | Phe |
|---|---|---|---|---|---|---|---|---|---|---|---|---|---|---|---|
| | | | 20 | | | | | 25 | | | | | 30 | | |

| Tyr | Pro | Ser | Asp | Ile | Ala | Val | Glu | Trp | Glu | Ser | Asn | Gly | Gln | Pro | Glu |
|---|---|---|---|---|---|---|---|---|---|---|---|---|---|---|---|
| | | 35 | | | | | 40 | | | | | 45 | | | |

| Asn | Asn | Tyr | Lys | Thr | Thr | Pro | Pro | Val | Leu | Asp | Ser | Asp | Gly | Ser | Phe |
|---|---|---|---|---|---|---|---|---|---|---|---|---|---|---|---|
| | 50 | | | | | 55 | | | | | 60 | | | | |

| Phe | Leu | Tyr | Ser | Trp | Leu | Thr | Val | Asp | Lys | Ser | Arg | Trp | Gln | Gln | Gly |
|---|---|---|---|---|---|---|---|---|---|---|---|---|---|---|---|
| 65 | | | | | 70 | | | | | 75 | | | | | 80 |

| Asn | Val | Phe | Ser | Cys | Ser | Val | Met | His | Glu | Ala | Leu | His | Asn | His | Tyr |
|---|---|---|---|---|---|---|---|---|---|---|---|---|---|---|---|
| | | | | 85 | | | | | 90 | | | | | 95 | |

| Thr | Gln | Lys | Ser | Leu | Ser | Leu | Ser | Pro | Gly | Lys |
|---|---|---|---|---|---|---|---|---|---|---|
| | | | 100 | | | | | 105 | | |

```
<210> SEQ ID NO 12
<211> LENGTH: 107
<212> TYPE: PRT
<213> ORGANISM: Artificial Sequence
<220> FEATURE:
<223> OTHER INFORMATION: Synthetic construct of EEW-RVT CH3B
      (EU numbering 341-447)

<400> SEQUENCE: 12
```

| Gly | Gln | Pro | Arg | Glu | Pro | Arg | Val | Tyr | Thr | Leu | Pro | Pro | Cys | Arg | Asp |
|---|---|---|---|---|---|---|---|---|---|---|---|---|---|---|---|
| 1 | | | | 5 | | | | | 10 | | | | | 15 | |

| Glu | Leu | Thr | Lys | Asn | Gln | Val | Ser | Leu | Thr | Cys | Leu | Val | Lys | Gly | Phe |
|---|---|---|---|---|---|---|---|---|---|---|---|---|---|---|---|
| | | | 20 | | | | | 25 | | | | | 30 | | |

| Tyr | Pro | Ser | Asp | Ile | Ala | Val | Glu | Trp | Glu | Ser | Asn | Gly | Gln | Pro | Glu |
|---|---|---|---|---|---|---|---|---|---|---|---|---|---|---|---|
| | | 35 | | | | | 40 | | | | | 45 | | | |

| Asn | Asn | Tyr | Lys | Thr | Thr | Pro | Pro | Val | Leu | Val | Ser | Asp | Gly | Ser | Phe |
|---|---|---|---|---|---|---|---|---|---|---|---|---|---|---|---|
| | 50 | | | | | 55 | | | | | 60 | | | | |

| Thr | Leu | Tyr | Ser | Lys | Leu | Thr | Val | Asp | Lys | Ser | Arg | Trp | Gln | Gln | Gly |
|---|---|---|---|---|---|---|---|---|---|---|---|---|---|---|---|
| 65 | | | | | 70 | | | | | 75 | | | | | 80 |

| Asn | Val | Phe | Ser | Cys | Ser | Val | Met | His | Glu | Ala | Leu | His | Asn | His | Tyr |
|---|---|---|---|---|---|---|---|---|---|---|---|---|---|---|---|
| | | | | 85 | | | | | 90 | | | | | 95 | |

| Thr | Gln | Lys | Ser | Leu | Ser | Leu | Ser | Pro | Gly | Lys |
|---|---|---|---|---|---|---|---|---|---|---|
| | | | 100 | | | | | 105 | | |

```
<210> SEQ ID NO 13
<211> LENGTH: 107
<212> TYPE: PRT
<213> ORGANISM: Artificial Sequence
<220> FEATURE:
<223> OTHER INFORMATION: Synthetic construct of SW-WVT CH3A
      (EU numbering 341-447)

<400> SEQUENCE: 13
```

| Gly | Gln | Pro | Arg | Glu | Pro | Gln | Val | Ser | Thr | Leu | Pro | Pro | Ser | Arg | Asp |
|---|---|---|---|---|---|---|---|---|---|---|---|---|---|---|---|
| 1 | | | | 5 | | | | | 10 | | | | | 15 | |

| Glu | Leu | Thr | Lys | Asn | Gln | Val | Ser | Leu | Thr | Cys | Leu | Val | Lys | Gly | Phe |
|---|---|---|---|---|---|---|---|---|---|---|---|---|---|---|---|
| | | | 20 | | | | | 25 | | | | | 30 | | |

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Synthetic construct of SW-WVT CH3B
      (EU numbering 341-447)

<400> SEQUENCE: 14

Gly Gln Pro Arg Glu Pro Gln Val Tyr Thr Leu Pro Pro Ser Arg Asp
 1               5                  10                  15

Trp Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Val Ser Asp Gly Ser Phe
 50                  55                  60

Thr Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: Synthetic construct of SW-WVT (S-S) CH3A
      (EU numbering 341-447)

<400> SEQUENCE: 15

Gly Gln Pro Arg Glu Pro Gln Val Ser Thr Leu Pro Pro Cys Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Trp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

```
<210> SEQ ID NO 16
<211> LENGTH: 107
<212> TYPE: PRT
<213> ORGANISM: Artificial Sequence
<220> FEATURE:
<223> OTHER INFORMATION: Synthetic construct of SW-WVT (S-S) CH3B
      (EU numbering 341-447)

<400> SEQUENCE: 16

Gly Gln Pro Arg Glu Pro Gln Val Cys Thr Leu Pro Pro Ser Arg Asp
 1               5                  10                  15

Trp Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Val Ser Asp Gly Ser Phe
    50                  55                  60

Thr Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic construct of KiH (Genentech) CH3A
      (EU numbering 341-447)

<400> SEQUENCE: 17

Gly Gln Pro Arg Glu Pro Gln Val Tyr Thr Leu Pro Pro Ser Arg Asp
 1               5                  10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Synthetic construct of KiH (Genentech) CH3B
      (EU numbering 341-447)

<400> SEQUENCE: 18

Gly Gln Pro Arg Glu Pro Gln Val Tyr Thr Leu Pro Pro Ser Arg Asp
 1               5                  10                  15

Glu Leu Thr Lys Asn Gln Val Ser Leu Trp Cys Leu Val Lys Gly Phe
            20                  25                  30
```

Tyr Pro Ser Asp Ile Ala Val Glu Trp Glu Ser Asn Gly Gln Pro Glu
            35                  40                  45

Asn Asn Tyr Lys Thr Thr Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 19
<211> LENGTH: 223
<212> TYPE: PRT
<213> ORGANISM: Artificial Sequence
<220> FEATURE:
<223> OTHER INFORMATION: Synthetic construct of Wild type Fc (A chain)
      (EU numbering 225-447)

<400> SEQUENCE: 19

Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 20
<211> LENGTH: 223
<212> TYPE: PRT
<213> ORGANISM: Artificial Sequence
<220> FEATURE:
<223> OTHER INFORMATION: Synthetic construct of Wild type Fc (B chain)
      (EU numbering 225-447)

<400> SEQUENCE: 20

```
Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 21
<211> LENGTH: 223
<212> TYPE: PRT
<213> ORGANISM: Artificial Sequence
<220> FEATURE:
<223> OTHER INFORMATION: Synthetic construct of E-R Fc (A chain)
      (EU numbering 225-447)

<400> SEQUENCE: 21

```
Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125
```

Pro Ser Arg Asp Glu Leu Thr Glu Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220

<210> SEQ ID NO 22
<211> LENGTH: 223
<212> TYPE: PRT
<213> ORGANISM: Artificial Sequence
<220> FEATURE:
<223> OTHER INFORMATION: Synthetic construct of E-R Fc (B chain)
      (EU numbering 225-447)

<400> SEQUENCE: 22

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Asp Pro Glu
             35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Arg Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
    210                 215                 220

<210> SEQ ID NO 23
<211> LENGTH: 223
<212> TYPE: PRT
<213> ORGANISM: Artificial Sequence
<220> FEATURE:
<223> OTHER INFORMATION: Synthetic construct of W-VT Fc (A chain)
      (EU numbering 225-447)

<400> SEQUENCE: 23

```
Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 24
<211> LENGTH: 223
<212> TYPE: PRT
<213> ORGANISM: Artificial Sequence
<220> FEATURE:
<223> OTHER INFORMATION: Synthetic construct of W-VT Fc (B chain)
      (EU numbering 225-447)

<400> SEQUENCE: 24

```
Thr Cys Pro Pro Cys Pro Ala Pro Glu Leu Leu Gly Gly Pro Ser Val
  1               5                  10                  15

Phe Leu Phe Pro Pro Lys

```
Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220
```

<210> SEQ ID NO 25
<211> LENGTH: 223
<212> TYPE: PRT
<213> ORGANISM: Artificial Sequence
<220> FEATURE:
<223> OTHER INFORMATION: Synthetic construct of EW-RVT Fc (A chain)
      (EU numbering 225-447)

<400> SEQUENCE: 25

```
Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Glu Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220
```

<210> SEQ ID NO 26
<211> LENGTH: 223
<212> TYPE: PRT
<213> ORGANISM: Artificial Sequence
<220> FEATURE:
<223> OTHER INFORMATION: Synthetic construct of EW-RVT Fc (B chain)
      (EU numbering 225-447)

-continued

```
<400> SEQUENCE: 26

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Lys Phe Asn Trp Tyr Val Asp Gly Val Glu Val His Asn Ala Lys
     50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Arg Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 27
<211> LENGTH: 223
<212> TYPE: PRT
<213> ORGANISM: Artificial Sequence
<220> FEATURE:
<223> OTHER INFORMATION: Synthetic construct of EW-RVT (S-S) Fc
      (A chain) (EU numbering 225-447)

<400> SEQUENCE: 27

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Lys Phe Asn Trp Tyr Val Asp Gly Val Glu Val His Asn Ala Lys
     50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Cys Thr Leu Pro
        115                 120                 125
```

```
Pro Ser Arg Asp Glu Leu Thr Glu Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
210                 215                 220

<210> SEQ ID NO 28
<211> LENGTH: 223
<212> TYPE: PRT
<213> ORGANISM: Artificial Sequence
<220> FEATURE:
<223> OTHER INFORMATION: Synthetic construct of EW-RVT (S-S) Fc
      (B chain) (EU numbering 225-447)

<400> SEQUENCE: 28

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Arg Val Tyr Thr Leu Pro
        115                 120                 125

Pro Cys Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
210                 215                 220

<210> SEQ ID NO 29
<211> LENGTH: 223
<212> TYPE: PRT
<213> ORGANISM: Artificial Sequence
<220> FEATURE:
<223> OTHER INFORMATION: Synthetic construct of EEW-RVT Fc (A chain)
      (EU numbering 225-447)
```

-continued

```
<400> SEQUENCE: 29

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Glu Val Tyr Thr Leu Pro
        115                 120                 125

Pro Ser Arg Asp Glu Leu Thr Glu Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 30
<211> LENGTH: 223
<212> TYPE: PRT
<213> ORGANISM: Artificial Sequence
<220> FEATURE:
<223> OTHER INFORMATION: Synthetic construct of EEW-RVT Fc (B chain)
      (EU numbering 225-447)

<400> SEQUENCE: 30

Thr Cys Pro Pro Cys Pro Ala Pro Glu Leu Leu Gly Gly Pro Ser Val
1               5                   10                  15

Phe Leu Phe Pro Pro Lys Pro Lys Asp Thr

```
Pro Cys Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220
```

<210> SEQ ID NO 31
<211> LENGTH: 223
<212> TYPE: PRT
<213> ORGANISM: Artificial Sequence
<220> FEATURE:
<223> OTHER INFORMATION: Synthetic construct of SW-WVT Fc (A chain)
      (EU numbering 225-447)

<400> SEQUENCE: 31

```
Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Ser Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Trp Leu Thr Val Asp Lys Ser Arg
            180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
    210                 215                 220
```

<210> SEQ ID NO 32
<211> LENGTH: 223
<212> TYPE: PRT
<213> ORGANISM: Artificial Sequence
<220> FEATURE:
<223> OTHER INFORMATION: Synthetic construct of SW-WVT Fc (B chain)
      (EU numbering 225

<400> SEQUENCE: 32

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Trp Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Val Ser
                165                 170                 175

Asp Gly Ser Phe Thr Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 33
<211> LENGTH: 223
<212> TYPE: PRT
<213> ORGANISM: Artificial Sequence
<220> FEATURE:
<223> OTHER INFORMATION: Synthetic construct of SW-WVT (S-S) Fc
(A chain) (EU numbering 225-447)

<400> SEQUENCE: 33

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Ser Thr Leu Pro
        115                 120                 125
```

```
Pro Cys Arg Asp Glu Leu Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Asp Ser
                165                 170                 175
Asp Gly Ser Phe Phe Leu Tyr Ser Trp Leu Thr Val Asp Lys Ser Arg
                180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
    210                 215                 220
```

<210> SEQ ID NO 34
<211> LENGTH: 223
<212> TYPE: PRT
<213> ORGANISM: Artificial Sequence
<220> FEATURE:
<223> OTHER INFORMATION: Synthetic construct of SW-WVT (S-S) Fc
      (B chain) (EU numbering 225-447)

<400> SEQUENCE: 34

```
Thr Cys Pro Pro Cys Pro Ala Pro Glu Leu Leu Gly Gly Pro Ser Val
  1               5                  10                  15
Phe Leu Phe Pro Pro Lys Pro Lys Asp Thr Leu Met Ile Ser Arg Thr
                 20                  25                  30
Pro Glu Val Thr Cys Val Val Val Asp Val Ser His Glu Asp Pro Glu
             35                  40                  45
Val Lys Phe Asn Trp Tyr Val Asp Gly Val Glu Val His Asn Ala Lys
 50                  55                  60
Thr Lys Pro Arg Glu Glu Gln Tyr Asn Ser Thr Tyr Arg Val Val Ser
 65                  70                  75                  80
Val Leu Thr Val Leu His Gln Asp Trp Leu Asn Gly Lys Glu Tyr Lys
                 85                  90                  95
Cys Lys Val Ser Asn Lys Ala Leu Pro Ala Pro Ile Glu Lys Thr Ile
            100                 105                 110
Ser Lys Ala Lys Gly Gln Pro Arg Glu Pro Gln Val Cys Thr Leu Pro
        115                 120                 125
Pro Ser Arg Asp Trp Leu Thr Lys Asn Gln Val Ser Leu Thr Cys Leu
    130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Val Ser
                165                 170                 175
Asp Gly Ser Phe Thr Leu Tyr Ser Lys Leu Thr Val Asp Lys Ser Arg
                180                 185                 190
Trp Gln Gln Gly Asn Val Phe Ser Cys Ser Val Met His Glu Ala Leu
                195                 200                 205
His Asn His Tyr Thr Gln Lys Ser Leu Ser Leu Ser Pro Gly Lys
    210                 215                 220
```

<210> SEQ ID NO 35
<211> LENGTH: 223
<212> TYPE: PRT
<213> ORGANISM: Artificial Sequence
<220> FEATURE:
<223> OTHER INFORMATION: Synthetic construct of KiH (Genentech) Fc
      (A chain) (EU numbering 225-447)

<400> SEQUENCE: 35

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Ser Cys Ala
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Val Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 36
<211> LENGTH: 223
<212> TYPE: PRT
<213> ORGANISM: Artificial Sequence
<220> FEATURE:
<223> OTHER INFORMATION: Synthetic construct of KiH (Genentech) Fc
      (B chain) (EU numbering 225-447)

<400> SEQUENCE: 36

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125
```

-continued

| | | | | | | | | | | | | | | |
|---|---|---|---|---|---|---|---|---|---|---|---|---|---|---|
| Pro | Ser | Arg | Asp | Glu | Leu | Thr | Lys | Asn | Gln | Val | Ser | Leu | Trp | Cys | Leu |
| | 130 | | | | | 135 | | | | 140 | | | | | |
| Val | Lys | Gly | Phe | Tyr | Pro | Ser | Asp | Ile | Ala | Val | Glu | Trp | Glu | Ser | Asn |
| 145 | | | | | 150 | | | | 155 | | | | | 160 | |
| Gly | Gln | Pro | Glu | Asn | Asn | Tyr | Lys | Thr | Thr | Pro | Pro | Val | Leu | Asp | Ser |
| | | | | 165 | | | | 170 | | | | | 175 | | |
| Asp | Gly | Ser | Phe | Phe | Leu | Tyr | Ser | Lys | Leu | Thr | Val | Asp | Lys | Ser | Arg |
| | | | 180 | | | | | 185 | | | | | 190 | | |
| Trp | Gln | Gln | Gly | Asn | Val | Phe | Ser | Cys | Ser | Val | Met | His | Glu | Ala | Leu |
| | | 195 | | | | | 200 | | | | | 205 | | | |
| His | Asn | His | Tyr | Thr | Gln | Lys | Ser | Leu | Ser | Leu | Ser | Pro | Gly | Lys | |
| | 210 | | | | | 215 | | | | 220 | | | | | |

CH3 DOMAIN VARIANT PAIR INDUCING FORMATION OF HETERODIMER OF HEAVY CHAIN CONSTANT REGION OF ANTIBODY AT HIGH EFFICIENCY, METHOD FOR PREPARING SAME, AND USE THEREOF

CROSS REFERENCE TO RELATED APPLICATIONS

This application is a National Stage of International Application No. PCT/KR2013/010861 filed Nov. 27, 2013, claiming priority based on Korean Patent Application No. 10-2012-0135586, filed Nov. 27, 2012, the contents of all of which are incorporated herein by reference in their entirety.

TECHNICAL FIELD

The present invention relates to a CH3 domain variant pair inducing a mutation to a CH3 domain for improving a yield of formation of a heterodimer at a heavy chain constant region of an antibody (immunoglobulin G, IgG), a heterodimeric Fc pair protein using the CH3 mutation pair, a bispecific antibody, and a fusion protein.

The present invention also relates to a pharmaceutical composition including the heterodimer, a heterodimeric Fc pair having the same, a bispecific antibody, and a fusion protein.

The present invention also relates to a method for preparing a CH3 domain variant pair and a heterodimeric Fc pair protein in which formation of the antibody CH3 domain heterodimeric Fc is preferred.

BACKGROUND ART

In the late 19th century, the fact that, when serum of an experimental animal to which diphtheria and tetanus of a non-lethal dose were administered was administered to other animals, diphtheria and tetanus can be prevented was found. After the finding, clinical use of the concept of serum therapy, that is, antibody therapy was gradually started. However, the early antibody treatment had very limited practicability due to problems of obtaining a high purity antibody and contamination by blood-borne infectious agents. In order to address such problems in the traditional antibody treatment, a rodent-originated monoclonal antibody of a pure form was produced on a large scale at a relatively low cost according to a hybridoma fusion technique developed in 1975. However, due to several problems and side effects such as a short half-life, an immune response to an anti-mouse antibody, reduced efficacy, and a fatal allergic reaction when a mouse originated monoclonal antibody is administered to a human body, a clinical use thereof was limited.

Due to the advent of a gene recombinant technique, which was a starting point of a biotechnology revolution in the 1980s, a humanized antibody in which a mouse monoclonal antibody is humanized through gene manipulation could be prepared; various immunological side effects caused when the antibody is administered to a patient were minimized; and the foundation of an active clinical use of a therapeutic antibody was established. Meanwhile, fundamental technology with which a complete human monoclonal antibody can be produced with the aid of a phage display technique or a transgenic mouse has been developed since the mid-1990s. Currently, many domestic and international pharmaceutical companies enthusiastically conduct a great deal of research and investment for developing a new drug using an antibody. Today, US Food and Drug Administration (FDA) approved new antibody drugs numbering about 26 which are commercially available worldwide, and 300 or more therapeutic antibodies are in a clinical trial step, which will show the importance of the antibody in the pharmaceutical industry. Meanwhile, preclinical and clinical trial results showing that, when an antibody having target selectivity and a chemotherapeutic agent having no target specificity are co-administered, side effects are suppressed and a therapeutic effect is improved have been recently reported. Therefore, usefulness of the antibody will be further increased in anti-cancer treatment.

Meanwhile, currently, a new antibody drug is being developed mainly for cancer and autoimmune diseases. In particular, a new antibody drug in the form of IgG or an intact antibody does not show a satisfactory therapeutic effect for solid tumors, and a high antibody production cost may be an obstacle to develop the new antibody drug. Therefore, the development of a new antibody drug of a recombinant protein form that has a more improved biological effect than the antibody in the related art has been continuously attempted. One of these is a bispecific antibody in which one antibody can bind to at least two target molecules, on which a research has been started since the mid-1980s to use the antibody, in particular, for anti-cancer treatment.

Natural antibodies (immunoglobulin G (IgG), IgM, IgD, IgE, and IgA) have a form in which two heavy chains having the same amino acid sequence and two light chains having the same sequence are assembled. In this case, formation of a homodimer of the same two heavy chains is induced through an interaction between the final domains (that is, a CH3 domain in IgG, a CH4 domain in IgM, a CH3 domain in IgD, CH2 and CH4 domains in IgE, and a CH3 domain in IgA) of a constant region (Fc, crystallizable fragment) of an antibody. Then, a disulfide bond between hinge regions is induced, and a homodimer between robust heavy chains is formed. Specifically, an assembly of a heavy chain and a light chain in human IgG1 is induced by a disulfide bond between the 5th Cys in a heavy chain hinge region and the 107th Cys in a kappa light chain.

Therefore, a natural monoclonal antibody (mAb) has a characteristic of bivalent binding to one type of an antigen. On the other hand, the bispecific antibody refers to an antibody in a single molecule form that can simultaneously or alternatively bind to two types of antigens. Such a bispecific antibody is known in the related art as a manipulated protein such as a dispecific or multi-specific antibody that can bind to two or more antigens, and can be prepared using cell fusion, chemical bonding, and recombinant DNA techniques.

In the related art, a bispecific antibody was prepared using a quadroma technique in which somatic cell fusion of two different hybridoma cell lines expressing a mouse monoclonal antibody having desired specificity is used (Milstein and Cuello 1983). In this case, two different light chains are randomly paired in quadroma cell lines to yield a maximum of 10 types of various antibodies, and it is very difficult to separate and purify a desired bispecific antibody from this antibody mixture. Accordingly, complex purification processes were necessary to obtain only a desired bispecific antibody since there exist byproducts that form a wrong pair and a production yield decreases (Morrison 2007).

As a method of addressing such problems, a bispecific antibody form in which antigen binding site fragments of a light chain and a heavy chain are connected by various chains and expressed in a single construct was developed. This form includes forms of single chain diabodies, a tandem single chain fragment variable (scFv) antibody and the like (Holliger and Hudson 2005). Also, a bispecific antibody in which additional antigen binding antibody fragments are fused to the N-terminus or C-terminus of a heavy chain or a light chain of an antibody, which has a similar form to Ig, was prepared (Miller, Meng et al. 2003; Lu, Zhang et al. 2004).

However, the bispecific antibody based on such an antibody fragment assembly has problems in that an expression level decreases due to low stability, antibody aggregation is formed, and immunogenicity increases accordingly (Chan and Carter 2010). Also, the bispecific antibody based on only the antibody fragment assembly has no heavy chain constant region (Fc) of the antibody. Therefore, there is a problem in that the following are absent: stability that increases in association with Fc, a long serum half-life depending on an increased size and binding to an Fc receptor (neonatal Fc receptor, FcRn), an advantage of binding site preservation (protein A and protein G) in a purification process, an antibody-dependent cellular cytotoxicity and a complement-dependent cellular cytotoxicity (Chan and Carter 2010).

Therefore, ideally, it is necessary to develop a bispecific antibody having a structure that is very similar to naturally occurring antibodies (IgG, IgM, IgA, IgD, and IgE) and having a minimum sequence deviation therefrom.

In order to resolve the above problem, it was attempted to develop a bispecific antibody using a knob-into-hole technique. In this technique, through gene manipulation, a mutation is induced in a CH3 domain of two different Ig heavy chains, a hole structure is made in a CH3 domain of one Ig heavy chain, a knob structure is made a CH3 domain of the other Ig heavy chain, and two Ig heavy chains are induced to form a heterodimer (U.S. Pat. No. 7,695,936 B2; Korean Laid-open Patent Application No. 10-2010-0087394). In this case, amino acid residues included in a hydrophobic core contributing to formation of the homodimer between human Ig heavy chain CH3 domains are Leu351, Thr366, Leu368, and Tyr407 according to EU numbering of the amino acid number of the antibody chain (Cunningham, Pflumm et al. 1969). In the knob-into-hole technique, it was reported that, with respect to residues positioned at a hydrophobic core in a CH3 domain interface, a hole structure is made in one heavy chain CH3 domain such that hydrophobic amino acid residues having a large side chain are substituted with hydrophobic amino acids having a small side chain (Thr366Ser, Leu368Ala, Tyr407Val), a knob structure is made in the other heavy chain CH3 domain such that hydrophobic amino acid residues having a small side chain are substituted with hydrophobic amino acids having a large side chain (Thr366Trp), and when two mutation pairs, that is, heavy chain constant region mutation pairs in which CH3A (Thr366Ser, Leu368Ala, and Tyr407Val) and CH3B (Thr366Trp) are introduced were co-expressed, formation of the heterodimeric Fc is preferred more than formation of the homodimer heavy chain constant region (Ridgway, Presta et al. 1996). However, in the knob-into-hole technique, it was reported that a yield of formation of the heterodimeric Fc (heterodimer heterodimeric Fc) is about 80% (Ridgway, Presta et al. 1996). In order to promote stabilization of the heterodimer, there is a case where a phage display and a disulfide bridge are introduced for further increasing the interaction (Atwell, Ridgway et al. 1997; Merchant, Zhu et al. 1998, and U.S. Pat. No. 5,731,168A).

As another method in which formation of the heterodimeric Fc (heterodimer heterodimeric Fc) is enhanced, there is an example where a mutation is induced in a charged amino acid in an interface between CH3 domains. Specifically, a CH3 domain in one constant region is induced to have positively charged side chain amino acids, and a CH3 domain in the other constant region is induced to have negatively charged side chain amino acids, thereby inhibiting formation of the homodimer due to electrostatic repulsion, and enhancing formation of the heterodimer due to electrostatic interaction (Gunasekaran, Pentony et al. 2010, and US Laid-open Patent Application No. 2010/0286374 A1). That is, Lys392Asp and Lys409Asp are introduced into one CH3 domain, Glu356Lys and Asp399Lys are introduced into the other CH3 domain, and thus, formation of the heterodimer was induced. A yield of formation of the heterodimeric Fc of the CH3 domain mutation is about 90%.

As still another method in which formation of the heterodimeric Fc (heterodimer heterodimeric Fc) is enhanced, there is an example where a complementary mutation is induced in a region forming a hydrophobic core region of a CH3 interface due to a size difference between hydrophobic amino acid side chains, and thus, formation of the heterodimer is enhanced (Moore, Bautista et al. 2011, and US Laid-open Patent Application No. US 2011/0054151 A1). Specifically, Ser364His and Phe495Ala are introduced into one CH3 domain, Tyr349Thr and Thr394Phe are introduced into the other CH3 domain, and thus, formation of the heterodimer was induced. A yield of formation of the heterodimeric Fc of the CH3 domain mutation is about 80 to 90%.

However, the heterodimeric Fc including the developed CH3 domain variant pair has a lower thermodynamic stability and expression yield than that of a wild type antibody.

Therefore, it is necessary to develop the heterodimeric Fc having a yield of formation of the heterodimer as high as possible, having a thermodynamic stability and expression yield that is similar to or more increased than that of a wild type, but there is still no report satisfying such necessity.

DISCLOSURE

Technical Problem

The present invention is devised to develop a technique for stably increasing a yield of formation of a heterodimeric Fc of an antibody to 90% or more, and provides a CH3 heterodimer in which a mutation is induced in a CH3 domain in order to increase a yield of formation of the heterodimeric Fc, and a method of preparing the same.

The present invention also provides a heterodimeric Fc pair including the CH3 heterodimer, a bispecific antibody, and a fusion protein.

The present invention also provides a bispecific antibody or an antibody constant region-fused protein including the CH3 heterodimer and having an expression level, a production yield and a thermodynamic stability that are similar to or more improved than an original wild type antibody.

The present invention also provides an antibody or an antibody constant region-fused protein including the CH3 heterodimer, maintaining an intrinsic function of a heavy chain constant region (Fc) of an original wild type antibody, that is, a binding ability to FcRn (neonatal Fc receptor) and FcRs (Fc gamma receptors), having a long serum half-life, maintaining an effector function, and preserving a binding site (protein A and protein G) in a purification process.

The present invention also provides a bispecific antibody or an antibody constant region-fused protein including the CH3 heterodimer, and capable of simultaneously targeting two types of different antigens.

The present invention also provides a method for preparing a CH3 domain variant (heterodimeric CH3) pair and a heterodimeric Fc pair (hinge-CH2-CH3A and hinge-CH2-Ch3B) protein in which formation of the heterodimeric Fc is preferred.

The scope of the present invention is not limited to the above-described objects, and other unmentioned objects may be clearly understood by those skilled in the art from the following descriptions.

Technical Solution

The present invention provides a heterodimer including antibody CH3 domains including the following binding (a): (a) in a first group of CH3 domain selected from the group consisting of Tyr349, Asp356, Glu357, Ser364, Lys370, Lys392, Asp399, Phe405 and Lys409, a binding between i) an amino acid selected from the group consisting of alanine (A), threonine (T), serine (S), valine (V), methionine (M), and glycine (G), which is substituted in at least one position of the first group, and ii) an amino acid selected from the group consisting of phenylalanine (F), tyrosine (Y) and tryptophan (W), which is substituted in at least one position of the first group (wherein, the positions are numbered according to the EU index).

The heterodimer including antibody CH3 domains may further include the following binding (b): (b) in a second group of CH3 domain selected from the group consisting of Gln347, Tyr349, Thr350, Ser354, Lys360, Ser364, Asn390, Thr394, Pro395, Val397 and Ser400, a binding between i) lysine (K) or arginine (R), which is substituted in at least one position of the second group, and ii) aspartic acid (D) or glutamic acid (E), which is substituted in at least one position of the second group (wherein, the positions are numbered according to the EU index).

According to an aspect of the present invention, the position of the first group may be selected from the group consisting of Tyr349, Glu357, Asp399, Phe405 and Lys409.

According to another aspect of the present invention, Lys409 of one CH3 domain may be substituted with tryptophan (W), and Asp399 and Phe405 of the other CH3 domain may be substituted with valine (V) and threonine (T), respectively.

According to still another aspect of the present invention, Tyr349 of one CH3 domain may be substituted with serine (S), and Glu357 of the other CH3 domain may be substituted with tryptophan (W).

According to yet another aspect of the present invention, the position of the second group may be Gln347 or Lys360.

According to yet another aspect of the present invention, Lys360 of one CH3 domain may be substituted with glutamic acid (E), and Gln347 of the other CH3 domain may be substituted with arginine (R).

According to yet another aspect of the present invention, Gln347 of one CH3 domain may be substituted with glutamic acid (E).

According to yet another aspect of the present invention, Lys360 and Lys409 of one CH3 domain may be substituted with glutamic acid (E) and tryptophan (W), respectively, and Gln347, Asp399 and Phe405 of the other CH3 domain may be substituted with arginine (R), valine (V) and threonine (T), respectively.

According to yet another aspect of the present invention, Gln347, Lys360 and Lys409 of one CH3 domain may be substituted with glutamic acid (E), glutamic acid (E) and tryptophan (W), respectively, and Gln347, Asp399 and Phe405 of the other CH3 domain may be substituted with arginine (R), valine (V) and threonine (T), respectively.

According to yet another aspect of the present invention, Tyr349 and Lys409 of one CH3 domain may be substituted with serine (S) and tryptophan (W), respectively, and Glu357, Asp399 and Phe405 of the other CH3 domain may be substituted with tryptophan (W), valine (V) and threonine (T), respectively.

According to yet another aspect of the present invention, the heterodimer including antibody CH3 domains may further include the following binding (c): (c) in a third group of CH3 domain selected from the group consisting of Tyr349 and Ser354, a binding between i) cysteine (C) substituted in at least one position of the third group, and ii) cysteine (C) substituted in at least one position of the third group (wherein the positions are numbered according to the EU index).

Advantageous Effects

In a CH3 domain heterodimer of a heavy chain constant region of an antibody according to the present invention, a mutation is induced using a method different from the conventional method, formation of the homodimer is minimized, and the heterodimer can be formed at a high yield of 90 to 95% or more. When a heterodimeric Fc pair protein prepared using the CH3 domain heterodimer is expressed in animal cells, the protein has an expression level, a production yield and a thermodynamic stability that are similar to or more improved than an original wild type antibody.

Also, a heterodimeric Fc pair protein prepared using a CH3 domain heterodimer of a heavy chain constant region (heterodimeric Fc) of an antibody according to the present invention has advantages in that an intrinsic function of a heavy chain constant region (Fc) of an original wild type antibody, that is, a binding ability to FcRn (neonatal Fc receptor) and FcRs (Fc gamma receptors) is maintained, a long serum half-life is provided, a binding site (protein A and protein G) is preserved in a purification process, and an antibody-dependent cellular cytotoxicity and a complement-dependent cellular cytotoxicity can be maintained.

Also, in a heterodimeric Fc pair protein prepared using a CH3 domain heterodimer of a heavy chain constant region (heterodimeric Fc) of an antibody according to the present invention, CH3 domain variants are not individually expressed and synthesized again, but are simultaneously expressed in one cell. Therefore, a heterodimer constant region (heterodimeric Fc) can be produced at a high yield of about 90 to 95% or more with high efficiency.

In addition, it is possible to prepare a bispecific antibody according to the present invention in an scFv-Fc form in which two types of antibody fragments (scFvs) having different antigen specificity are fused to the N-terminus or C-terminus of a heterodimer constant region (heterodimeric Fc) pair protein, in an scIgG (scFab-Fc) form in which two types of scFabs are fused, and in an (Fv)$_2$-Fc form in which two types of a heavy chain variable region (VH) and light chain variable region (VL) pair, which form antigen binding Fv, are fused to the N-terminus and C-terminus of a heterodimeric Fc, respectively, at a high yield with high efficiency. Also, it is possible to prepare a bispecific antibody in a bispecific variable region-fused single antibody mAb-Fv form in which a single variable antigen binding domain (VH or VL) is fused to the C-terminus of a typical IgG heavy chain consisting of two heavy chain constant regions (Fcs) where a CH3 domain variant pair is included at a high yield with high efficiency. Also, it is possible to prepare a monovalent antigen binding antibody in an Fv-Fc form in which a heavy chain variable region (VH) and a light chain variable region (VL), which bind to a single antigen, are fused to the N-terminus or C-terminus of two heavy chain constant regions (Fcs) where a CH3 domain variant pair is included at a high yield with high efficiency. Also, it is possible to prepare an antibody constant region-fused protein (Protein-Fc) in which cell membrane receptor extracellular domains capable of binding to a specific protein, a peptide, a single domain antibody, a ligand, a toxin and the like are fused, and that can specifically recognize one type or two types of proteins at a high yield with high efficiency.

Also, since a bispecific antibody or an antibody constant region-fused protein (Protein-Fc) that can simultaneously target two types of antigens according to the present invention can simultaneously target two types of antigens related to tumors or immunological diseases caused by redundant, indirect and gradual operations of several proteins not by caused by one protein, it is possible to increase a therapeutic effect compared to a monoclonal antibody targeting only one type of a target protein.

In addition, an antibody (Fv-Fc) prepared according to the present invention in which a heavy chain variable region (VH) and a light chain variable region (VL), which bind to a single antigen, are fused to be capable of monovalently binding to a single antigen can more effectively target a target antigen when the antigen is targeted with a monovalent binding antibody (mAb) than when the antigen is targeted with a bivalent binding antibody (mAb). Therefore, a high effect for treating target antigen-related diseases can be expected.

In addition, an antibody constant region-fused protein (Protein-Fc) prepared according to the present invention in which cell membrane receptor extracellular domains capable of binding to a specific protein, a peptide, a single domain antibody, a ligand, a toxin and the like are fused to Fc can specifically recognize one type or two types of proteins and can effectively target a target protein that can be targeted using an existing homodimer heavy chain constant region (homodimeric Fc). Therefore, a high effect for treating target protein-related diseases can be expected.

DESCRIPTION OF DRAWINGS

FIG. 1 is a diagram schematically illustrating a structure of a natural IgG1 antibody specific to one antigen. A wild type IgG1 antibody has a form in which two heavy chains having the same amino acid sequence and two light chains having the same sequence are assembled. In order for two pairs of heavy chains to form a dimer, formation of the dimer is induced by an interaction between CH3 domains. Then, a disulfide bond between hinge regions is induced, and a homodimer between robust heavy chains is formed. The assembly of the heavy chain and the light chain is induced by a disulfide bond between the 5th Cys in a heavy chain hinge region and the 107th Cys in a kappa light chain.

FIG. 2 is a diagram schematically illustrating an interface between CH3 domains in a wild type IgG1 antibody. An inside of the interface includes residues related to hydrophobic interaction and residues having an electrostatic interaction. These residues contribute to formation of a dimer of the CH3 domain. Also, there are residues that exist in the interface, but have no interaction with residues adjacent thereto. These residues do not contribute to formation of the dimer, or participate in the interaction with a relatively weak non-covalent interaction.

FIG. 3 is a diagram illustrating an interaction between amino acid side chains in which a mutation is introduced in an interface between CH3 domains of a heavy chain structure of a human IgG1 antibody. An interface between CH3 domains was analyzed based on an Fc fragment structure (PDB code: 1FC1 (Deisenhofer 1981), 1L6X (Idusogie, Presta et al. 2000), and 3AVE (Matsumiya, Yamaguchi et al. 2007)) of the known human antibody. An interaction between amino acid side chains in which a mutation is introduced in an interface between CH3 domains is illustrated based on a 3AVE structure.

FIG. 3 (A) is a diagram illustrating Lys360 and Lys409 amino acid side chains in a CH3A domain and Gln347, Asp399, and Phe405 amino acid side chains in a CH3B domain in a CH3 domain of a wild type human IgG1 antibody. An existing K360 amino acid in one CH3 domain is adjacent to Gln347 amino acid in the other CH3 domain, but there is no interaction contributing to formation of the dimer in the CH3 domain. Also, Lys409 in one CH3 domain and Asp399 in the other CH3 domain are amino acid residues that significantly contribute to formation of the CH3 domain dimer due to the electrostatic interaction.

FIG. 3 (B) is a diagram illustrating a predicted model of a structure of a CH3 domain of a CH3 domain mutation. Lys360Glu and Lys409Trp mutations were introduced in one CH3 domain, and Gln347Arg, Asp399Val, and Phe405Thr mutations were introduced in the other CH3 domain. Therefore, existing Lys360 and Gln347 were substituted with Lys360Glu and Gln347Arg so that selective electrostatic interaction could be generated between residues having no interaction. This mutation strategy may contribute to selectively form a heterodimer of the CH3 domain. Also, mutations of Lys409Trp and Asp399Val and Phe405Thr in the other CH3 domain were introduced so that complementary hydrophobic interaction instead of the existing electrostatic interaction could be induced. This is a mutation strategy in which formation of the homodimer such as CH3A:CH3A, and CH3B:CH3B is inhibited and formation of the heterodimer of CH3A:CH3B is induced.

FIG. 4 illustrates an interaction between Lys409 in a CH3A domain and Asp399 and Phe405 residues in a CH3B domain in the mutation strategy. In a wild type CH3 domain interface, Lys409 in one domain electrostatically binds to Asp399 residues in the other domain, which contributes to formation of the dimer between the domains. Therefore, by introducing thereinto mutations of Lys409Trp in one CH3 domain and Asp399Val and Phe405Thr in the other CH3 domain, a mutation capable of inducing complementary hydrophobic interaction between only heterodimers instead of the existing electrostatic interaction was induced. This is a mutation strategy in which formation of the homodimer such as CH3A:CH3A, and CH3B:CH3B is inhibited and formation of the heterodimer of CH3A:CH3B is induced.

FIG. 5 illustrates an interaction between mutations of Lys360Glu in a CH3A domain and Gln347Arg in a CH3B domain in the mutation strategy. Mutation residues are adjacent in a wild type, but there is no interaction through which an existing CH3 domain contributes to form a dimer. Here, Lys360Glu and Gln347Arg mutations that can induce a long-range electrostatic interaction between only heterodimers were induced. This is a mutation strategy in which formation of the homodimer such as CH3A:CH3A and CH3B:CH3B is inhibited, and formation of the heterodimer of CH3A:CH3B is induced.

FIG. 6 illustrates an interaction between a Gln347E mutation in a CH3A domain and Lys360 residues in a CH3B domain in the mutation strategy. These residues are positioned at a region symmetrical with a Lys360Glu-Gln347Arg interaction region illustrated in FIG. 5 in the interface of the CH3 domain. Similar to the above Lys360Glu-Gln347Arg interaction region, residues of Gln347 in the CH3A domain and Lys360 in the CH3B domain are adjacent in the wild type, but there is no interaction through which an existing CH3 domain contributes to form a dimer. Here, a Gln347Glu mutation was introduced to induce selective electrostatic interaction with the Lys360 residue in the other CH3 domain. This is a mutation strategy in which formation of the homodimer such as CH3A:CH3A and CH3B:CH3B is inhibited, and formation of the heterodimer of CH3A:CH3B is induced.

FIG. 7 illustrates an interaction between Glu357 in a CH3A domain and Tyr349 and Lys370 residues in a CH3B domain in the mutation strategy. In a wild type CH3 domain interface, Glu357 in one domain electrostatically binds to Lys370 residues in the other domain, which contributes to formation of the dimer between the domains, and is adjacent to Tyr349 residues in the other domain. Therefore, by introducing thereinto mutations of Glu357Trp in one CH3 domain and Tyr349Ser in the other CH3 domain, a mutation capable of inducing complementary hydrophobic interaction between only heterodimers instead of the existing electrostatic interaction between Glu357 and Lys370 was induced. This is a mutation strategy in which formation of the homodimer such as CH3A:CH3A and CH3B:CH3B is inhibited, and formation of the heterodimer of CH3A:CH3B is induced.

FIG. 8 is a diagram schematically illustrating a case in which a CH3 domain mutation pair (CH3A and CH3B) into which the mutation according to the present invention is introduced inhibits formation of a heavy chain constant region homodimer according to an interaction of CH3A:CH3A or CH3B:CH3B and induces formation of a heterodimeric Fc according to an interaction of CH3A:CH3B.

FIG. 9 is a diagram schematically illustrating a bispecific antibody and an Fc-fusion protein that can be prepared using a heterodimeric Fc generated by connecting a heterodimer-forming CH3 mutation pair (CH3A:CH3B) according to the present invention to the C-terminus of a hinge-CH2 domain of a heavy chain constant region of an antibody. It is possible to prepare a bispecific single chain antibody fragment immunoglobulin (scFv-Fc) in which two types of single chain fragment variable (scFv) antibodies having different antigen binding specificity are fused to each amino terminus (N-terminus) in a heterodimeric Fc; a bispecific single chain immunoglobulin (scFab-Fc) in which two types of single chain antigen binding fragments (Fabs) having different antigen binding specificity are fused to each amino terminus (N-terminus); a bispecific variable region-fused immunoglobulin (Fv)2-Fc in which two types of a single variable antigen binding domain (VH or VL) of a heavy chain and a light chain derived from an antibody that recognizes different antigens are fused in a pair to the N-terminus and C-terminus of a heavy chain constant region, respectively; a bispecific variable region-fused single antibody mAb-Fv in which a single variable antigen binding domain (VH or VL) is fused to the C-terminus of a typical IgG heavy chain; a monovalent antigen binding variable region fused immunoglobulin (Fv-Fc) in which a single variable antigen binding domain (VH or VL) of a heavy chain and a light chain derived from an antibody that recognizes one type of an antigen is fused to the N-terminus of a heavy chain constant region; and an antibody constant region-fused protein (Protein-Fc) in which two types of a cellular membrane protein extracellular domain specifically recognizing a ligand, a peptide, a single domain antibody recognizing one type of an antigen, a single domain antibody, a peptide, a ligand protein, a toxin protein and the like are fused to the N-terminus of a heavy chain constant region.

FIG. 10 shows sequence comparison of CH3 domains of IgG1 (as represented by the amino acid sequence of SEQ ID NO: 1), IgG2 (as represented by the amino acid sequence of SEQ ID NO: 37), IgG3 (as represented by the amino acid sequence of SEQ ID NO: 38), and IgG4 (as represented by the amino acid sequence of SEQ ID NO: 39) of human antibodies with IgG1 (as represented by the amino acid sequence of SEQ ID NO: 40), IgG2A (as represented by the amino acid sequence of SEQ ID NO: 41), IgG2B (as represented by the amino acid sequence of SEQ ID NO: 42), and IgG3 (as represented by the amino acid sequence of SEQ ID NO: 43) of mouse antibodies. Gln347, Lys360, Asp399, Phe405, Lys409 residues, which are emphasized in bold font, are residues into which a mutation is introduced. It can be observed that the residues into which a mutation is introduced are preserved as almost similar residues regardless of the human antibody and a subtype of a mouse antibody IgG. Therefore, it can be understood that the mutation induced to form a heterodimer CH3 mutation pair in the present invention is not limited to the human antibody IgG1.

Figure 12E:
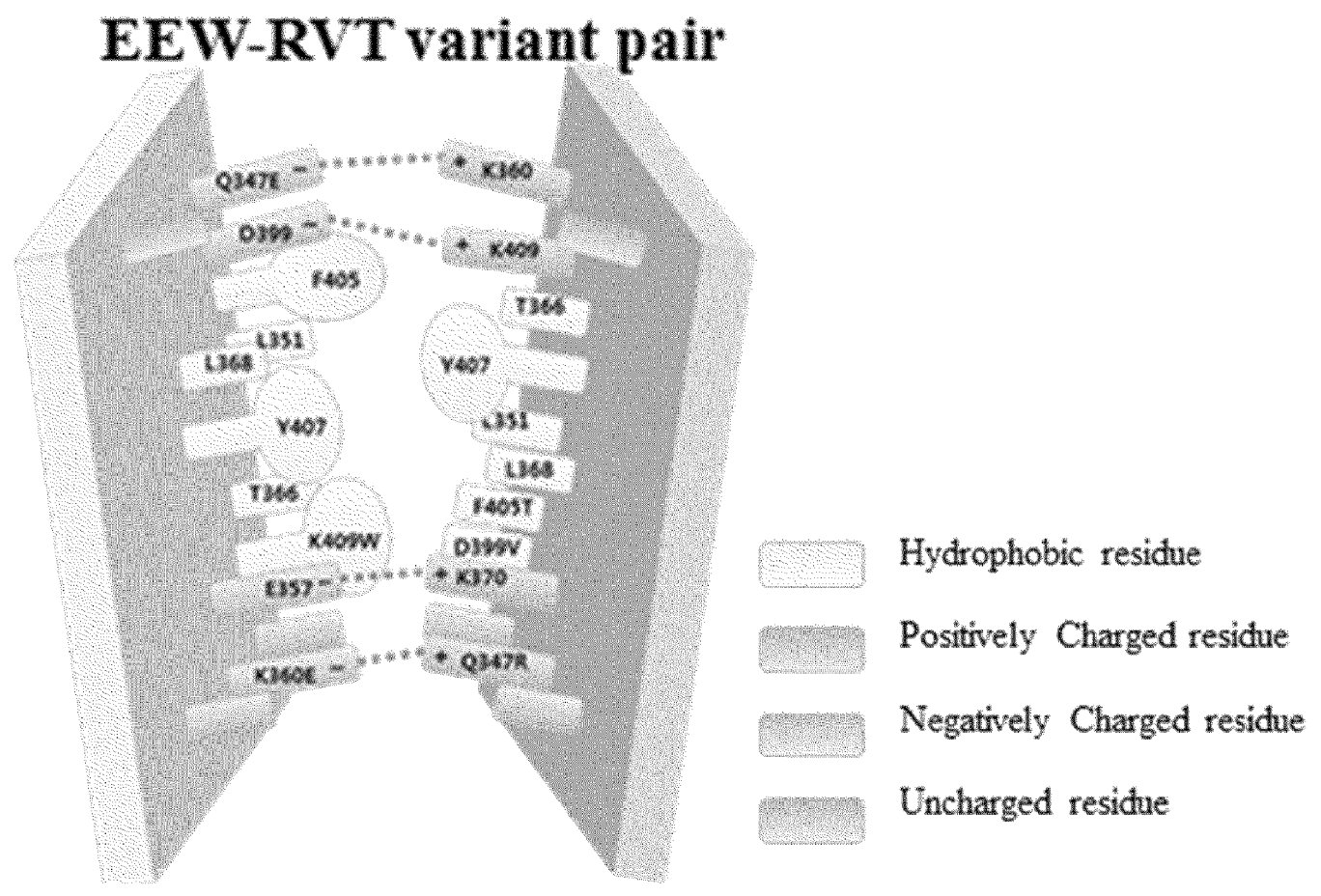

FIG. 11 and FIGS. 12(a) to 12(f) are diagrams schematically illustrating 5 CH3 mutation pairs whose formation yield are compared in a heterodimeric Fc that is expressed and purified in the present invention.

FIGS. 13 and 14 are schematic diagrams and vector maps designed for cloning scFv-Fc in which a single chain fragment variable (scFv) antibody constructed to evaluate a yield of formation of the heterodimer of a heavy chain constant region of an antibody through a prepared CH3 mutation pair is fused and a dummy Fc into a pcDNA3.1 vector serving as an animal cell expression vector.

FIG. 15 is a diagram illustrating a case in which, when the scFv-Fc and the dummy Fc animal cell expression vector constructed in FIGS. 13 and 14 are co-transfected and expressed in animal cells, a production yield of the heterodimer due to the CH3 mutation pair can be evaluated through size and assembly form analysis since a homodimer and a heterodimer are expressed as antibodies of different sizes.

FIGS. 16 and 19 show the results obtained by introducing the CH3 mutation pair prepared in FIGS. 13 and 14 into the animal cell expression vector in order to evaluate a formability of the heterodimer described in FIG. 15, temporarily expressing and purifying the CH3 mutation pair in HEK293F cells through co-transformation, and analyzing a size and an assembly form in an SDS-PAGE under non-reducing conditions in order to evaluate a heterodimer antibody formability. In this case, an antibody in which a wild type CH3 is employed was used as a negative control group, a knob-into-hole bispecific antibody was used as a positive control group, and an amount of proteins used for analysis was about 10 μg.

FIGS. 17 and 18 show the results obtained by temporarily expressing the CH3 mutation pair prepared in FIGS. 13 and 14 in HEK293F cells through co-transformation, and then analyzing a size and an assembly form of a purified heterodimer antibody are analyzed using an antibody that specifically recognizes a human Fc region in a western blot. In this case, an antibody in which a wild type CH3 is employed was used as a negative control group, and a knob-into-hole bispecific antibody was used as a positive control group.

FIG. 17 shows the result obtained under non-reducing conditions, while

FIG. 18 shows the result obtained under reducing conditions. An amount of proteins used for analysis was 0.1 µg.

FIG. 20 shows the result obtained by expressing a wild type, a mutation EW-RVT, and an Fc dimer of the knob-into-hole (positive control group) in the forms constructed in FIG. 13, and then measuring circular dichroism in order to confirm whether a secondary structure of an Fc dimer protein into which a mutation CH3 domain is introduced is preserved in the same form as that of a wild type. As a result, it was confirmed that the Fc dimer into which the CH3 mutation is introduced has the same circular dichroism as the wild type Fc dimer, and the secondary structure of the protein is maintained without modification.

FIG. 21 shows the result obtained by expressing a mutation EW-RVT in the heterodimer form illustrated in FIG. 14, and then performing surface plasmon resonance (SPR) in order to confirm whether an Fc dimer into which a mutation CH3 domain is introduced preserves a binding ability to FcRn. It was confirmed that the antibody including the mutation CH3 domain maintains the binding ability to FcRn, similar to the antibody including the wild type CH3 domain. In this case, Remicade™ (Infliximab, Janssen Biotech), which is an antibody including a human antibody IgG1, was used as a positive control group.

FIG. 22 (A) is a diagram schematically illustrating a bispecific antibody in which the CH3 mutation pair prepared in the present invention is introduced into a scFv-Fc form. A humanized hAY4a scFv antibody (Lee, Park et al. 2010) specifically binding to a target antigen DR4 and an affinity-improved AU5H scFv antibody of a human HW1 scFv antibody (Park, Lee et al. 2007) specifically binding to a target antigen DR5 were fused to the N-terminus of Fc in which the CH3 domain variant was used to constant a DR4×DR5 bispecific antibody in a form of scFv-Fc.

FIG. 22 (B) shows the result obtained by co-transforming HEK293F cells with a vector expressing a bispecific scFv-Fc antibody, temporarily expressing and purifying the antibody, and then analyzing the antibody through SDS-PAGE under non-reducing conditions. The constructed CH3 domain mutation pair EW-RVT was introduced into a heavy chain, and a knob-into-hole bispecific antibody was used as a positive control group.

FIG. 22 (C) shows the result obtained by performing a size exclusion chromatography to confirm a size of an expressed and purified bispecific scFv-Fc antibody in a native state. It was confirmed that only a desired protein of a size of 103 kD was detected, which is identical to the control group.

FIG. 23 (A) is a diagram schematically illustrating a bispecific antibody in which the CH3 mutation pair prepared in the present invention is introduced into a scFab-Fc form (scIgG). A used parent antibody includes a humanized hAY4a antibody and an AU5H antibody, which are the same as those used in the bispecific antibody of the scFv-Fc form in FIG. 20. A single chain Fab (scFab) form in which a VH-CH domain and a VL-CL domain are connected via 26 amino acid chain linkers was fused to the N-terminus of an Fc region to construct DR4×DR5 bispecific antibody in a form of scFab-Fc.

FIG. 23 (B) shows the result obtained by co-transforming HEK293F cells with a vector expressing the bispecific scFab-Fc antibody, temporarily expressing and purifying the antibody and then, analyzing the antibody through SDS-PAGE under non-reducing conditions and reducing conditions. The constructed CH3 domain mutation pair EW-RVT was introduced into a heavy chain, and a knob-into-hole bispecific antibody was used as a positive control group. It can be observed that a desired bispecific antibody is mainly generated, which is identical to the control group.

FIG. 23 (C) shows the result obtained by performing an enzyme linked immunosorbent assay (ELISA) in order to confirm a binding ability and specificity of the purified DR4×DR5 bispecific scFv-Fc antibody in FIG. 20 and the DR4×DR5 bispecific scFab-Fc antibody in FIG. 21 with respect to DR4 and DR5 antigens. As a result, it was confirmed that the prepared bispecific antibody has specificity to antigen DR4 and DR5. In this case, as similar antigens of DR4 and DR5, DcR1 and DcR2 was used as control antigens.

FIG. 24 shows the result obtained by performing a cytotoxicity experiment (MTT assay) in HCT116 and HeLa cell lines in order to confirm a cancer cell killing activity of the purified DR4×DR5 bispecific scFv-Fc antibody in FIG. 20 and the DR4×DR5 bispecific scFab-Fc antibody in FIG. 21. It is observed that the prepared bispecific antibodies of two forms have a higher cytotoxicity than their parent antibodies, hAY4 IgG and AU5H scFv, and have a cytotoxicity that is similar to or more excellent than TRAIL used as a positive control group.

MODES OF THE INVENTION

A heavy chain of an antibody exists as a homodimer in a native state. In this case, formation of a dimer between heavy chains is stabilized due to a disulfide bond of a hinge region when the dimer is generated by a non-covalent interaction between CH3-CH3 domains of a heavy chain constant region (Schroeder and Cavacini 2010) (see FIG. 1). The dimer between CH3 domains of the heavy chain constant region is generated when beta-sheet residues of one heavy chain bind non-covalently to side chains of opposite beta-sheet residues, and accordingly, a thermodynamically stabilized homodimer is formed (Schroeder and Cavacini 2010).

An interaction between CH3 domains forming the homodimer of a heavy chain constant region of an IgG antibody was analyzed by observing an X-ray crystal structure. A used structure is PDB code=1FC1, 1L6X and 3AVE.

According to the result of analyzing residues of an interface between CH3 domains, a hydrophobic interaction core structure that significantly contributes to formation of the homodimer due to hydrophobic interaction is present inside the interface, and this includes Leu351, Thr366, Leu368, and Tyr407 residues. Also, there are Asp356, Glu357, Lys370, Lys392, Asp399, Lys409, and Lys439 residues that contribute to formation of the dimer between CH3 domains through an electrostatic interaction on the interface. In particular, electrostatic interactions between Lys409 residues of the CH3 domain of one heavy chain and Asp399 residues of the CH3 domain of the opposite, different heavy chain and electrostatic interactions between Glu357 residues of the CH3 domain of one heavy chain and Lys370 residues of the CH3 domain of the opposite, different heavy chain occur inside between CH3 domains and contribute to increased formation of the homodimer through electrostatic interactions.

Also, there are Gln347, Tyr349, Thr350, Ser354, Lys360, Ser364, Asn390, Thr394, Pro395, Val397, 400S residues that are present in the interface but have no interaction for significantly contributing to formation of the dimer between CH3 domains such as a hydrophobic interaction or an electrostatic interaction with adjacent amino acid residues (see FIG. 2). Some of these residues contribute to an interaction between domains with a relatively weak non-covalent interaction.

In this case, the term "non-covalent interaction" refers to an interaction having a weak binding force when atoms or molecules form an aggregate due to an interaction other than a covalent interaction, and includes interactions of an electrostatic interaction, a hydrophobic interaction, hydrogen bonding, and a Van der Waals interaction.

The term "electrostatic interaction" refers to an interaction dependent on electrical attraction between oppositely charged ions. The term "hydrophobic interaction" refers to an interaction in which an interaction with a polar solvent is excluded and that is caused by a thermodynamically stabilizing tendency of hydrophobic molecules. The term "hydrogen bonding" refers to an interaction between a dipole and a dipole which is generated between polar covalent interaction molecules generated when hydrogen, fluorine, oxygen, and nitrogen meet. Also, the term "Van der Waals interaction" refers to an interaction in which molecules have polarity due to a Van der Waals force and an attractive force and a repulsive force act therebetween.

Also, the term "homodimer" refers to a dimer of an antibody domain having the same amino acid sequence or including a part of or an entire antibody including the same, and specifically, refers to a dimer between CH3 domains of a heavy chain constant region of an antibody or a dimer of a heavy chain constant region of an antibody including the same CH3 domain.

Also, the term "homodimeric Fc" refers to a dimer between heavy chain constant regions (hinge-CH2-CH3) having the same amino acid sequence.

In the present invention, amino acid residues contributing to an interaction between CH3 domains are modified, and formation of a pair (CH3A:CH3B) in which a CH3 domain (CH3A) of one heavy chain and a CH3 domain (CH3B) of the other heavy chain can selectively interact through the non-covalent interaction is induced. The present inventors have endeavored to increase a yield of formation of a heterodimeric Fc in a heavy chain constant region pair in which a CH3 mutation pair is fused to the C-terminus of hinge-CH2, that is, between hinge-CH2-CH3A and hinge-CH2-CH3B, and completed the present invention.

In this case, the term "heterodimer" refers to a dimer including two types of antibody domains having different amino acid sequences, or including a part of or an entire antibody including the same, and specifically, a dimer including a CH3 domain pair having different sequences of a heavy chain constant region of an antibody or including a part of or an entire antibody including a CH3 domain pair having different sequences.

Also, the term "heterodimeric Fc" refers to a dimer between heavy chain constant regions (hinge-CH2-CH3) including CH3A and CH3B respectively having different amino acid sequences.

Also, the term "yield of formation of the heterodimeric Fc" refers to a ratio (percentage) of a heavy chain constant region formed as a heterodimer to a total heavy chain constant region dimer (homodimer and heterodimer) or a sum of monomers when a heavy chain constant region pair including a CH3 domain mutation pair was simultaneously transformed in HEK293F animal cells, expressed and purified.

The present invention provides a heterodimer including antibody CH3 domains including the following binding (a): (a) in a first group of CH3 domain selected from the group consisting of Tyr349, Asp356, Glu357, Ser364, Lys370, Lys392, Asp399, Phe405 and Lys409, a binding between i) an amino acid selected from the group consisting of alanine (A), threonine (T), serine (S), valine (V), methionine (M), and glycine (G), which is substituted in at least one position of the first group, and ii) an amino acid selected from the group consisting of phenylalanine (F), tyrosine (Y) and tryptophan (W), which is substituted in at least one position of the first group (wherein, the positions are numbered according to the EU index).

The heterodimer including antibody CH3 domains may further include the following binding (b): (b) in a second group of CH3 domain selected from the group consisting of Gln347, Tyr349, Thr350, Ser354, Lys360, Ser364, Asn390, Thr394, Pro395, Val397 and Ser400, a binding between i) lysine (K) or arginine (R), which is substituted in at least one position of the second group, and ii) aspartic acid (D) or glutamic acid (E), which is substituted in at least one position of the second group (wherein, the positions are numbered according to the EU index).

The heterodimer including antibody CH3 domains in which the position of the first group is selected from the group consisting of Tyr349, Glu357, Asp399, Phe405 and Lys409 is preferable, but the present invention is not limited thereto.

The heterodimer including antibody CH3 domains in which Lys409 of one CH3 domain is substituted with tryptophan (W), and Asp399 and Phe405 of the other CH3 domain are substituted with valine (V) and threonine (T), is preferable, but the present invention is not limited thereto.

The heterodimer including antibody CH3 domains in which Tyr349 of one CH3 domain is substituted with serine (S), and Glu357 of the other CH3 domain is substituted with tryptophan (W) is preferable, but the present invention is not limited thereto.

Also, the heterodimer including antibody CH3 domains in which the position of the second group is Gln347 or Lys360 is preferable, but the present invention is not limited thereto.

The heterodimer including antibody CH3 domains in which Lys360 of one CH3 domain is substituted with glutamic acid (E), and Gln347 of the other CH3 domain is substituted with arginine (R) is preferable, but the present invention is not limited thereto.

The heterodimer including antibody CH3 domains in which Gln347 of one CH3 domain is substituted with glutamic acid (E) is preferable, but the present invention is not limited thereto.

The heterodimer including antibody CH3 domains in which Lys360 and Lys409 of one CH3 domain are substituted with glutamic acid (E) and tryptophan (W), respectively, and Gln347, Asp399 and Phe405 of the other CH3 domain are substituted with arginine (R), valine (V) and threonine (T), respectively, is preferable, but the present invention is not limited thereto.

The heterodimer including antibody CH3 domains in which Gln347, Lys360 and Lys409 of one CH3 domain are substituted with glutamic acid (E), glutamic acid (E) and tryptophan (W), respectively, and Gln347, Asp399 and Phe405 of the other CH3 domain are substituted with arginine (R), valine (V) and threonine (T), respectively, is preferable, but the present invention is not limited thereto.

Also, the heterodimer including antibody CH3 domains in which Tyr349 and Lys409 of one CH3 domain are substituted with serine (S) and tryptophan (W), respectively, and Glu357, Asp399 and Phe405 of the other CH3 domain are substituted with tryptophan (W), valine (V) and threonine (T), respectively, is preferable, but the present invention is not limited thereto.

The heterodimer including antibody CH3 domains may further include the following binding (c): (c) in a third group of CH3 domain selected from the group consisting of Tyr349 and Ser354, a binding between i) cysteine (C) substituted in at least one position of the third group, and ii) cysteine (C) substituted in at least one position of the third group (wherein the positions are numbered according to the EU index).

Also, the heterodimer including antibody CH3 domains that is included in an Fc region of an immunoglobulin selected from the group consisting of IgG, IgM, IgA, IgD and IgE is preferable, but the present invention is not limited thereto. The heterodimer including antibody CH3 domain in which the IgG is a human IgG is preferable, but the present invention is not limited thereto. The heterodimer including antibody CH3 domain in which the human IgG is selected from the group consisting of IgG1, IgG2, IgG3 and IgG4 is preferable, but the present invention is not limited thereto.

In an example of the present invention, in a mutation pair induced in heterogeneous CH3 domains (CH3A and CH3B), a yield of formation of the heterodimer increases using a method different from a conventional strategy. In order to form a stabilized heterodimeric Fc, a CH3 domain variant pair was designed.

Specifically, among amino acid residues that are positioned inside the interface between CH3 domains and not exposed to the outside, a hydrophobic core having a high contribution to formation of the dimer between CH3 domains was maintained, and a mutation was induced in Asp356, Glu357, Lys370, Lys392, Asp399, and Lys409 residues that are present inside the interface and contribute to formation of a homodimer between CH3 domains due to an electrostatic interaction. A mutation pair having a space complementary-hydrophobic interaction mutation was prepared such that a hydrophobic residue of an interface of one heavy chain could be inserted between hydrophobic residues of an interface of an opposite, different heavy chain. When this approach is used, a further increased formability of the heterodimer can be expected by removing an interaction contributing to formation of the homodimer between existing CH3 domains, and substituting the interaction with an interaction that can induce formation of a hydrophobic attraction only in the heterodimer. Also, in this approach, the maximum amount of amino acid residues of a hydrophobic core of a wild type CH3 domain interface is preserved and stability of the heterodimer to be generated therethrough can be increased. This approach is a strategy different from the knob-into-hole technique (Ridgway, Presta et al. 1996) in which a selective hydrophobic interaction is formed in an existing hydrophobic core part to prepare a heterodimer antibody.

Also, in Gln347, Tyr349, Thr350, Ser354, Lys360, Ser364, Asn390, Thr394, Pro395, Val397, Ser400 residues that are present in the interface between CH3 domains but do not significantly contribute to increased formation of the dimer between CH3 domains by a hydrophobic interaction or an electrostatic interaction with adjacent amino acid residues, a selective electrostatic interaction mutation pair in which a charge of an amino acid residue of one heavy chain and a charge of a residue of an opposite, different heavy chain are opposite was induced. As a result, the interaction between homogeneous CH3 domains was excluded, and a selective long-range electrostatic interaction capable of increasing formation of the heterodimer was induced. In this approach, an electrostatic interaction is introduced such that amino acid residues can interact with residues of the opposite CH3 domain at a relatively long distance. Accordingly, a new interaction is generated, and this interaction contributes to selective formation of the heterodimer.

Also, in the above approach, a heterodimer CH3 domain variant pair in which a hydrophobic core part positioned inside the interface between CH3 domains is preserved can maintain a thermodynamic stability, immunogenicity, and expression productivity in animal cells, which are similar to those of a wild type.

Also, Thr250, Met252, Ile253, Ser254, Thr256, Thr307, His310, Glu380, Met428, His433, Asn434, His435, and Tyr436, which are sites to which existing FcRn (neonatal Fc receptor) binds, and Leu234, Leu235, Gly236, and Gly237 which are sites to which FcgR (fc gamma receptors) binds, are preserved. Therefore, it is possible to provide a long serum half-life according to a binding between an antibody heavy chain and FcRn or FcgR, and maintain intrinsic activities of an antibody such as an antibody-dependent cellular cytotoxicity and a complement-dependent cellular cytotoxicity (Wines, Powell et al. 2000; Roopenian and Akilesh 2007).

Also, in another example of the present invention, a system for evaluating heterodimer formability of the designed CH3 domain variant was constructed. Specifically, the system expresses and purifies an antibody in which a heavy chain constant region of an antibody including each CH3 domain mutation pair is fused in animal cells. In this case, in the mutation pair, a single chain fragment variable (scFv) antibody was fused and expressed in only one heavy chain constant region in which the CH3A domain is included, and a heavy chain constant region in which the CH3B domain is included was expressed alone without antibody fragment fusion. As a result, the heavy chain in which the CH3A domain is included has a greater molecular weight than the heavy chain in which the CH3B domain is included. Therefore, the heterodimer (scFv-Fc:Fc) and the homodimer (scFv-Fc:scFv-Fc, Fc:Fc) have different movement rates in SDS-PAGE under non-reducing conditions so that an amount of the heterodimer among the expressed and purified antibodies can be relatively compared (see FIG. 15).

Also, in still another example of the present invention, when the constructed system for evaluating heterodimer formability is used, it was confirmed that the antibody including the CH3 domain variant pair according to the present invention has a formation yield of about 90 to 95%, which is significantly higher than a yield of formation of the heterodimer using the conventional knob-into-hole technique (see FIGS. 16 and 17).

Further, the present invention provides a heterodimeric Fc pair including the heterodimer containing a CH3 domain and a bispecific antibody including the heterodimer containing a CH3 domain.

Preferably, the bispecific antibody has a form selected from the group consisting of scFv-Fc, scIgG (scFab-Fc), (Fv)$_2$-Fc, mAb-Fv and Fv-Fc, but is not limited thereto. The fusion protein is preferably in the form of a protein-Fc, but is not limited thereto.

The CH3 heterodimer according to the present invention in which a mutation is induced in the CH3 domain of the heavy chain constant region of the antibody may form a heterodimeric Fc pair protein. The heterodimeric Fc pair protein may have a form of a bispecific antibody, and that can simultaneously bind to two different antigens, in which antibodies having different antigen specificity are fused in the form of a heavy chain variable region (VH), a light chain variable region (VL), a single chain fragment variable (scFv) antibody or a single chain antibody Fab (scFab) fragment, various forms of a bispecific variable region-fused single antibody (mAb-Fv) in which a single variable antigen binding domain (VH or VL) is fused to the C-terminus of a typical IgG heavy chain, an antibody (Fv-Fc) in which a heavy chain variable region (VH) and a light chain variable region (VL), which bind to a single antigen, are fused to monovalently bind to the single antigen, or a form of an antibody constant region-fused protein (Protein-Fc) in which cell membrane receptor extracellular domains capable of binding to a specific protein, a peptide, a single domain antibody, a ligand, a toxin and the like are fused to specifically recognize one type or two types of proteins.

Specifically, in an example of the present invention, the CH3 domain variant pair according to the present invention was used to prepare an anti-DR4×DR5 bispecific antibody in the form of scFv and scFab, and it was confirmed that the bispecific antibody has specificity for the target molecules DR4 and DR5 (see FIGS. 22 and 23). As a result, it can be understood that the bispecific antibody prepared using the CH3 domain variant pair of the present invention maintains a binding ability to an antigen binding site without change.

In this case, the term "single chain fragment variable (scFv) antibody" is a VH-L-VL to VL-L-VH polypeptide in which one VH and one VL are connected using a proper peptide linker (L) of 12 or more residues and refers to an antibody fragment having an antigen binding activity.

Also, the term "single chain Fab (scFab) antibody fragment" is a VL-CL-L-VH-CH1 to VH-CH1-L-VL-CL polypeptide in which a heavy chain fragment expressed from one VH to CH1 and a light chain including one VL and a CL part are connected using a proper peptide linker (L) of 34 or more residues, and refers to an antibody fragment having an antigen binding activity.

Also, the term "fragment variable (Fv)" refers to a minimum antibody fragment including a complete antigen binding site. The term "Fv-Fc" used herein refers to an antibody in which a heavy chain variable region (VH) and a light chain variable region (VL), which bind to a single antigen, are fused to the N-terminus or the C-terminus of the heterodimeric Fc pair protein and that can monovalently bind to the single antigen.

Also, the term "mAb-Fv" used herein refers to an antibody in which a heavy chain variable region (VH) and a light chain variable region (VL) are fused to the C-terminus of a typical IgG heavy chain and that can trivalently bind to an antigen, or a bispecific antibody that can bivalently bind to an mAb antigen and monovalently bind to an Fv antigen.

Also, the term "antibody constant region-fused protein (Protein-Fc)" used herein refers to a fusion protein in which cell membrane receptor extracellular domains capable of binding to a specific protein, a peptide, a single domain antibody, a ligand, a toxin and the like are fused to the N-terminus or the C-terminus of the heterodimeric Fc pair protein according to the present invention and that can specifically recognize one type or two types of proteins.

In addition, the present invention provides a pharmaceutical composition including a bispecific antibody or a fusion protein including the heterodimeric Fc pair protein.

Since the bispecific antibody or the fusion protein prepared in the present invention can specifically target an antigen or a protein related to tumors or immunological diseases, the bispecific antibody or the fusion protein can be usefully used for a pharmaceutical composition that can treat or prevent the diseases.

In this case, a pharmaceutical composition including the bispecific antibody or the fusion protein prepared in the present invention can simultaneously target two types of antigens related to tumors or immunological diseases that develop from redundant, indirect and gradual actions of several proteins, rather than pathogenesis induced by one protein. Therefore, it can increase a therapeutic effect of disease compared to a pharmaceutical composition including a monoclonal antibody targeting only one type of a target protein.

Specifically, in an example of the present invention, in order to investigate a cancer cell killing activity of anti-DR4×DR5 scFv-Fc and scFab-Fc bispecific antibodies prepared in the present invention, an cytotoxicity experiment (MTT assay) was performed on cell lines of a human-derived cancer cell HCT116 (colorectal carcinoma) and HeLa (adenocarcinoma). It can be understood that the two forms of bispecific antibodies have a greater cancer cell killing activity than parent antibodies, a humanized antibody hAY4a IgG and a human antibody AU5H-scFv, and have a similar or slightly better cytotoxicity than TRAIL used as a positive control group (see FIG. 24).

The term "treatment" used herein refers to improvement of symptoms of disease or all activities that are beneficially changed by administration of the composition of the present invention.

When the pharmaceutical composition according to the present invention is formulated, a diluent or a diluting agent such as a filler, an extending agent, a binding agent, a wetting agent, a disintegrating agent and a surfactant, which are commonly used, is used for preparation.

A solid preparation for oral administration includes tablets, pills, powders, granules, capsules, troches and the like. Such solid preparations are prepared when at least one diluting agent, for example, starch, calcium carbonate, sucrose, lactose or gelatin, is mixed with one or more compounds according to the present invention. In addition to the simple diluting agent, lubricants such as magnesium stearate and talc are also used. A liquid preparation for oral administration includes a suspending agent, an oral solution, an emulsion, a syrup and the like. In addition to water and liquid paraffin which are commonly used as simple diluents, several diluting agents, for example, a wetting agent, a sweetener, a fragrance, and a preservative may be included.

A preparation for parenteral administration includes a sterilized aqueous solution, a non-aqueous solvent, a suspending solvent, an emulsion, a freeze-dried preparation, a suppository and the like.

As the non-aqueous solvent and the suspending solvent, vegetable oils such as propylene glycol, polyethylene glycol, and olive oil, an injectable ester such as ethyl oleate and the like may be used. The suppository may use bases such as Witepsol, macrogol, Tween 61, cacao butter, laurin butter, glycerol, and gelatin.

The composition of the present invention may be administered orally or parenterally (for example, intravenously, subcutaneously, or locally) according to a desired method. The dose is changed according to a patient's condition, body weight, and a degree of disease, a drug form, and routes of administration, and time, and those skilled in the art can appropriately select the dose.

The composition of the present invention is administered at a pharmaceutically effective amount. In the present invention, the term "pharmaceutically effective amount" refers to an amount that is sufficient to treat disease at a reasonable benefit/risk ratio applicable for medical treatment. A level of the effective dose may be determined by factors including a patient's disease type and severity of disease, a drug activity, drug sensitivity, an administration time, routes of administration, a discharge ratio, a treatment period, and a simultaneously used drug, and other factors well-known in the field of medicine. The composition of the present invention may be administered as an individual therapeutic agent or in combination with other therapeutic agents. The composition of the present invention may be sequentially or simultaneously administered with a therapeutic agent in the related art, or administered at single or multiple times. It is important to administer an amount at which a maximum effect can be obtained with a minimum amount which does not cause side effects in consideration of the all above factors, which can be easily determined by those skilled in the art.

Specifically, the effective amount of the compound according to the present invention may be changed according to a patient's age, sex, and body weight, and generally administered at 0.01 g to 100 mg per kg of body weight, and preferably 0.01 g to 10 mg daily or every other day, or may be divided into one to three times per day. However, since the amount can be increased or decreased according to routes of administration, severity of obesity, sex, body weight, age and the like, the present invention is not limited to the dose.

The present invention also provides a method for preparing a CH3 domain variant (heterodimeric CH3) pair including the following steps.

The method includes: (a) preparing a mutation pair by i) in a first group of CH3 domain selected from the group consisting of Tyr349, Asp356, Glu357, Ser364, Lys370, Lys392, Asp399, Phe405 and Lys409, substituting at least one amino acid positioned in the first group with an amino acid selected from the group consisting of alanine (A), threonine (T), serine (S), valine (V), methionine (M) and glycine (G); and ii) substituting at least one amino acid positioned in the first group with an amino acid selected from the group consisting of phenylalanine (F), tyrosine (Y) and tryptophan (W); (b) preparing mutation pair by i) in a second group of CH3 domain selected from the group consisting of Gln347, Tyr349, Thr350, Ser354, Lys360, Ser364, Asn390, Thr394, Pro395, Val397 and Ser400, substituting at least one amino acid positioned in the second group with lysine (K) or arginine (R); and ii) substituting at least one amino acid positioned in the second group with aspartic acid (D) or glutamic acid (E); and (c) binding the mutation pairs in Step (a) and (b).

The present invention also provides a method for preparing a heterodimeric Fc pair (hinge-CH2-CH3A and hinge-CH2-Ch3B) protein, the method including: (d) preparing a recombinant Fc pair protein expression vector including nucleic acids in which the prepared CH3 domain variant pair is fused to the C-terminus of a wild-type hinge-CH2 domain of heavy chain constant region of an antibody; (e) expressing the recombinant Fc pair protein by co-transforming the prepared expression vector with cells; and (f) purifying and recovering the co-expressed recombinant Fc pair protein.

EXAMPLES

Hereinafter, preferred examples of the invention will be described for promoting an understanding of the invention. However, the following examples should be considered in a descriptive sense only and the scope of the invention is not limited to the following examples.

<Example 1> Design of CH3 Domain Variant for Increasing Heterodimer Formability of Heavy Chain Constant Region of Antibody In order to induce a CH3 domain mutation for forming a heterodimer of a heavy chain constant region (Fc) of a human antibody IgG1, as described above, first, residues of an amino acid pair (non-covalent interaction) that mainly acts in an interaction between CH3 domains were analyzed. Based on the analysis result, a mutation pair in which formation of the homodimer between CH3 domains is excluded and formation of the heterodimer is thermodynamically preferred was designed. That is, in order to increase a selective interaction between the CH3 domain (CH3A) of one heavy chain and the CH3 domain (CH3B) of the other heavy chain through modification of amino acid residues contributing to an interaction between CH3 domains, substitutions of non-covalent interaction forming amino acid residues were induced in the CH3A and CH3B, and thereby formation of heterodimeric Fc CH3A:CH3B was induced. In this case, a mutation pair induced in heterogeneous CH3A:CH3B was designed such that CH3A:CH3B is formed at a high yield and stably maintained by employing a different strategy from that used for a mutation pair for increasing formation of the heavy chain constant region heterodimer disclosed in the related document or patent. Also, in order to minimize potential immunogenicity, mutation of amino acid residues was restricted to residues in the interface between CH3 domains. A mutation in FcRn and FcRs binding site residue was excluded to maintain an intrinsic function of a heavy chain constant region of an antibody (Roopenian and Akilesh 2007). Also, by evaluating a yield of formation of the heterodimeric Fc formed of CH3A:CH3B having a minimum mutation pair and CH3A:CH3B having a combination thereof, the development of a CH3A:CH3B mutation pair having the highest yield of formation of the heterodimeric Fc was attempted.

For this purpose, among amino acid residues positioned at the interface between CH3 domains, mutation pairs 1) and 2) were designed and constructed; 1) the mutation pair in which residues contributing to formation of a CH3 domain homodimer due to an electrostatic interaction inside the CH3 domain interface are substituted with an amino acid residue mutation pair capable of generating a space complementary-hydrophobic interaction, and thus formation of the homodimer is excluded and formation of the heterodimer is preferred, and 2) the CH3 mutation pair in which amino acid residues that do not significantly contribute to formation of the dimer between CH3 domains are substituted with an amino acid residue mutation pair in which a long-range electrostatic interaction is selectively formed, and thus formation of the homodimer is excluded and formation of the heterodimer is thermodynamically preferred.

That is, in order to induce a selective space complementary-hydrophobic interaction mutation pair inside the CH3 domain interface, positions and interactions of hydrophilic and hydrophobic amino acid residues positioned inside the interface between CH3 domains were analyzed, and a mutation pair in which formation of a spatially selective hydrophobic interaction for forming the heterodimer is preferred among these was introduced into CH3A:CH3B.

Also, in order to induce a new long-range electrostatic interaction mutation pair in the CH3 domain interface, except residues at a hydrophobic binding region inside the interface and residues that have already participated in the electrostatic interaction, positions and interactions of residues that are in the CH3 domain interface but have no interaction with adjacent residues, residues that interact due to a relatively weak hydrogen bond or a Van Der Waals interaction, and residues that have a long inter-side chain distance from a relatively adjacent residue and are inappropriate for the interaction were analyzed. A mutation pair in which formation of a selective long-range electrostatic interaction for forming the heterodimer among these is preferred was introduced into CH3A:CH3B, and thus formation of the heterodimer was induced.

Other than hydrophobic interaction core amino acid residues inside the CH3 domain interface, an amino acid mutation pair capable of generating a selective hydrophobic interaction in place of the electrostatic interaction and an amino acid mutation pair in which a new electrostatic interaction is introduced into the interface were analyzed and constructed as follows.

[CH3A (Lys409Trp):CH3B (Asp399Val, Phe405Thr)]

Lys409 in CH3A is positioned inside the CH3 domain interface, and is adjacent to Leu368, Asp399, Phe405, and Tyr407 in CH3B. Among these, an electrostatic interaction between Lys409 and Asp399 of the other chain contributes to an interaction between CH3 domains. Asp399 in CH3B is adjacent to Lys392 and Lys409 in CH3A, and an electrostatic interaction therebetween contributes to the interaction between CH3 domains. When the electrostatic interaction adjacent to a hydrophobic interaction core between CH3 domains is substituted to form a selective hydrophobic interaction, the existing electrostatic interaction that has contributed to formation of the homodimer between CH3 domains is removed, formation of the heterodimer between CH3 domains is selectively induced due to a space complementary hydrophobic interaction, and thus an increase in heterodimer formability can be expected. For this purpose, a mutation pair was induced in Lys409Trp in CH3A and Asp399Val in CH3B (FIG. 4).

Also, Phe405 in CH3B is adjacent to Lys392, Thr394, and Lys409 in CH3A, and formation of the heterodimer may be inhibited due to a spatial collision between a side chain of Lys409Trp of CH3A in which a mutation is induced and a large hydrophobic side chain of Phe405 in CH3B. Therefore, a Phe405Thr mutation was induced to maintain a hydrophobic interaction while being spatially disposed with a side chain.

When Lys409 in the CH3A domain is substituted with tryptophan (W), generation of the homodimer between CH3A domain is inhibited. This is because it is not possible to maintain the existing electrostatic interaction of Lys409: Asp399 and a space layout in the CH3 domain interface is difficult due to side chains of Phe405 and Tyr407 of other adjacent chains.

When Asp399 in the CH3B domain is substituted with valine (V), the existing electrostatic interaction of Asp399: Lys392 and Asp399:Lys409 pairs is removed and thus generation of the homodimer can be relatively inhibited.

Also, when Phe405 in the CH3B domain is substituted with threonine (T), there is no effect of relatively inhibiting generation of the homodimer, but the substitution can contribute to a hydrophobic interaction with Lys409Trp in the CH3A domain when the heterodimer is formed.

Therefore, a combination of Lys409Trp substitution in the CH3A domain and Asp399Val substitution in the CH3B, and a combination of Lys409Trp substitution in the CH3A domain and Phe405Thr substitution in the CH3B domain maintain the most appropriate distance between an interaction interface between CH3 domains, and maintain a complementary hydrophobic interaction. Therefore, generation of the heterodimer of CH3A:CH3B is preferred.

[CH3A (Lys360Glu):CH3B (Gln347Arg)]

Lys360 in CH3A is positioned outside the CH3 domain interface, and is adjacent to side chains of Gln347 and Tyr349 in CH3B. Lys360 contributes to the interaction between CH3 domains with very weak hydrogen bonding due to a long distance. Therefore, when residues of Lys360 in CH3A and Gln347 in CH3B are changed to oppositely charged amino acid residues having a large side chain, formation of the heterodimer is preferred due to the long-range electrostatic interaction. Therefore, when Lys360 in CH3A is substituted with Glu, and Gln347 in CH3B is substituted with arginine (R), formation of CH3A:CH3B is preferred due to an interaction between Glu360 in CH3A and Arg347 in CH3B. However, in CH3B, formation of the homodimer is inhibited due to electrostatic repulsion of the Lys360:Gln347Arg pair (FIG. 5).

[CH3A (Gln347Glu):CH3B (Lys360)]

Similar to the weak interaction between side chains of Lys360 in the CH3A domain and Gln347 in the CH3B domain, long-range weak hydrogen bonding between a Gln347 side chain in the CH3A domain and a Lys360 side chain in the CH3B domain contributes to the interaction between CH3 domains. Therefore, when residues are changed to oppositely charged amino acid residue, a relatively long-range electrostatic interaction is introduced to assist formation of the heterodimer. In this case, in order to use together with the mutation pair of Lys360Glu in the CH3A domain and Gln347Arg in the CH3B domain, Gln347 in the CH3A domain was substituted with Glu to interact with Lys360 in the CH3B domain (FIG. 6).

Therefore, in the mutation pair of Lys360Glu in the CH3A domain and Gln347Arg in the CH3B domain and the mutation pair of Gln347Glu in the CH3A domain and Lys360 in the CH3B domain, formation of the heterodimer is preferred due to each electrostatic interaction, formation of the homodimer is inhibited between CH3A domains due to an electrostatic repulsive force between Gln347Glu and Lys360Glu, and formation of the homodimer is inhibited between CH3B domains due to an electrostatic repulsive force between Gln347Arg and Lys360.

[CH3A (Tyr349Ser):CH3B (Glu357Trp)]

Tyr349 in CH3A is positioned outside the CH3 domain interface, and is adjacent to side chains of Ser354, Asp356, Glu357, and Lys360 in CH3B. Glu357 in CH3B is positioned outside the CH3 domain interface, is adjacent to side chains of Tyr459 and Lys370 in CH3A and participates in the interaction between CH3 domains according to a long-range electrostatic interaction with Lys370.

Therefore, when Tyr349 in CH3A is substituted with serine (S), and Glu357 in CH3B is substituted with tryptophan (W), the existing electrostatic interaction between Glu357 in CH3B and Lys370 in CH3A is removed and formation of CH3A:CH3B is preferred due to a complementary interaction depending on sizes of side chains between Tyr349Ser and Glu357Trp in CH3A (FIG. 7).

Also, Glu357Trp in CH3B removes the electrostatic interaction with Lys370 in CH3A, and is adjacent to Tyr349 in CH3B. Therefore, a space layout in the domain interface becomes difficult, and thus formation of the homodimer between CH3B domains may be inhibited.

[CH3A (Ser354Cys):CH3B (Tyr349Cys)/CH3A (Tyr349Cys):CH3B (Ser354Cys)]

Ser354 in the CH3A domain is adjacent to Tyr349 in the CH3B domain, and when the two residues are substituted with cysteine (C), a disulfide bridge between the domains is formed. When the disulfide bridge is introduced, the formed heterodimer may be stabilized. Since the introduced one disulfide bridge is positioned asymmetrically to the CH3 domain interface, it assists to increase a heterodimer production yield. Substitution of Tyr349 residue in the CH3A domain and Ser354 residue in the CH3B domain with cysteine (C) may function similar to the above.

<Example 2> Method of Constructing CH3 Domain Mutation for Increasing Heterodimer Formability of Heavy Chain Constant Region of Antibody The CH3 domain mutation pair designed in Example 1 was constructed as CH3A:CH3B composed alone or in a combination thereof, and 5 types of CH3A:CH3B heterodimer pairs were constructed. In order to stabilize the constructed heterodimer pair and increase the heterodimer production yield, two types of mutations into which the disulfide bridge is introduced were constructed (FIG. 11 and Table 1).

In CH3A and CH3B mutations, DNA was synthesized (Bioneer, Korea) to induce the designed mutation based on heavy chain constant region CH3 domain base sequences of IgG1. The base sequences were checked through sequencing (Macrogen, Korea), and the constructed CH3A:CH3B mutation pairs are shown in the following [Table 1].

TABLE 1

Mutation pairs (CH3A:CH3B) constructed for forming human CH3 domain heterodimers and mutation pairs introduced into each domain

| Mutant name | CH3A | CH3B |
|---|---|---|
| E-R | K360E | Q347R |
| W-VT | K409W | D399V/F405T |
| EW-RVT | K360E/K409W | Q347R/D399V/F405T |
| EW-RVT (S-S) | Y349C/K360E/K409W | Q347R/S354C/D399V/F405T |
| EEW-RVT | Q347E/K360E/K409W | Q347R/D399V/F405T |
| SW-WVT | Y349S/K409W | E357W/D399V/F405T |
| SW-WVT (S-S) | Y349S/S354C/K409W | Y349C/E357W/D399V/F405T |

<Example 3> Construction of System for Evaluating Heterodimer Formability of CH3 Domain Variant Prepared in the Present Invention In order to evaluate the yield of formation of the heterodimer of the CH3 domain mutation prepared in <Example 2>, cloning in an animal expression vector was performed such that the constructed CH3A domain could be expressed in an scFv-Fc form and the CH3B domain could be expressed in a dummy-Fc form (FIGS. 13 and 14). A used scFv antibody is an antibody in which VH and VL regions of hAY4a, which is an affinity-improved humanized antibody hAY4 specifically binding to DR4, are connected (Lee, Park et al. 2010).

The hAY4a scFv-Fc and the dummy-Fc were cloned in pcDNA3.1(+) (Invitrogen, USA), which is an animal cell expression vector having a CMV promoter, to have a signal sequence-hAY4a-scFv-Hinge-CH2-CH3 or a signal sequence-Hinge-CH2-CH3 using an SacI/XbaI in-frame.

As described above, when the CH3A domain is expressed in the scFv-Fc form and the CH3B domain is expressed in the dummy-Fc form, it can be understood that yields of forming the homodimer and the heterodimer in the purified antibody may be checked by SDS-PAGE. This uses a principle that since the scFv-Fc form has a greater molecular weight than the dummy-Fc form, the scFv-Fc homodimer, the scFv-Fc/dummy-Fc heterodimer, and the dummy-Fc homodimer have different molecular weights, and that can be distinguished depending on a difference of a band movement distance in SDS-PAGE (FIG. 15). The following [Table 2] shows the constructed scFv-Fc/dummy-Fc CH3 domain variant pairs. scFv-Fc and dummy-Fc expression forms for evaluating heterodimer formability of the heavy chain constant region including the constructed CH3 domain mutation pair are shown. KiH was used as a control group.

TABLE 2

Mutation pairs used for system for evaluating heterodimer formability

| Mutant name | scFv-Fc (CH3A) | dummy-Fc (CH3B) |
|---|---|---|
| E-R | K360E | Q347R |
| W-VT | K409W | D399V/F405T |
| EW-RVT | K360E/K409W | Q347R/D399V/F405T |
| EW-RVT (S-S) | Y349C/K360E/K409W | Q347R/S354C/D399V/F405T |
| EEW-RVT | Q347E/K360E/K409W | Q347R/D399V/F405T |
| SW-WVT | Y349S/K409W | E357W/D399V/F405T |
| SW-WVT (S-S) | Y349S/S354C/K409W | Y349C/E357W/D399V/F405T |
| KiH (Genentech) | T366S/L368A/Y407V | T366W |

<Example 4> Expression and Purification of Antibody Including CH3 Domain Variant Using an HEK293-F system (Invitrogen), a heavy chain including each plasmid CH3A variant constructed in <Example 3> and a heavy chain including the CH3B variant were transiently transfected to generate a bispecific antibody. In a shake flask or a stirred fermenter, HEK293-F cells (Invitrogen) that are suspended and grown in a serum-free FreeStyle 293 expression medium (Invitrogen) were transfected with a mixture of two expression plasmids and polyethylenimine (PEI, Polyscience). HEK293-F cells were seeded in 1 L shake flasks (Corning) at a density of 1.0E*6 cells/mL in 200 mL, and cultured at 120 rpm, 8% $CO_2$. One day later, at a cell density of about 2.0E*6 cells/mL at the same molar ratio, the cells were transfected with about 21 mL of mixture of 10 mL FreeSytle™ 293 expression medium (Invitrogen) and 10 mL FreeSytle™ 293 expression medium+800 PEI (4/mL), which contain a total of 400 (2/mL) of plasmid DNAs encoding a heavy chain including the CH3A variant and a heavy chain including the CH3B variant. A supernatant was collected five days later.

With reference to a standard protocol, a protein was purified from the collected cell culture supernatant. Antibodies were applied to a protein A Sepharose column (GE healthcare), and washed with PBS (pH 7.4). The antibodies were eluted at pH 3.0 using 0.1M glycine buffer solution, and then the sample was immediately neutralized using a 1M Tris buffer solution. Eluted antibody fractions were concentrated using a MILLIPORE Amicon® Ultra (10 MWCO) centrifugal concentrator after the buffer solution is changed to PBS (pH7.4) using a Pierce™ Dextran Desalting Column (5K MWCO). Purified Fc variant antibodies were quantified through a BCA technique.

<Example 5> Evaluation of Heterodimer Formability of Antibody Including CH3 Domain Variant, Yield Comparison, and Analysis of Protein Secondary Structure and Binding Ability to FcRn 10 g of the antibody into which the CH3 mutation pair purified in <Example 4> is introduced was analyzed by SDS-PAGE under 12% non-reducing conditions (FIG. 16). The homodimer of the CH3A variant was observed at 103 kD, the homodimer of the CH3B variant was observed at 53 kD, the monomer of the CH3B variant was observed at 25 kD, and the heterodimer of the CH3A variant and CH3B variant was observed at 78 kD.

It was confirmed that, when the plasmid DNAs including the heavy chain including the CH3A variant and the heavy chain including the CH3B variant were transiently transfected at the same molar concentration, and expressed and purified, heterodimer formability of the mutant increased compared to the control group (the heterodimer into which the wild type CH3 domain is introduced). It was confirmed that EW-RVT and EEW-RVT variants in which two pairs were assembled had heterodimer formability that further increased to about 91% compared to the E-R variant and the W-VT variant. The two variants showed a further increased heterodimer formability than that of control group, about 86% of the knob-into-hole (Table 3). Also, a small amount of an Fc monomer was observed in all variants including a wild type antibody. This is considered to be caused by an expression degree difference between heavy chains.

Also, it was confirmed that the E-R variant has scFv-Fc/Fc heterodimer formability of about 53%, and the W-VT variant has scFv-Fc/Fc heterodimer formability of about 77%. A newly added long-range electrostatic interaction can contribute to an increase in the heterodimer formability. However, it can be understood that a strategy that the existing interaction applied for homodimer formability inside the interface is removed and a selective space complementary-hydrophobic interaction is added relatively greatly contributes to an increase in the heterodimer formability.

Also, it was confirmed that, when two strategies are simultaneously performed, heterodimer formability is further promoted than when the strategy that an additional space complementary-hydrophobic interaction is introduced into the CH3 domain interface or the strategy that a new long-range electrostatic interaction mutation pair is additionally introduced into the interface is performed alone.

Also, the heavy chain constant region Fc dimer protein into which the constructed CH3 mutation pair is introduced is well purified with a protein A resin similar to the wild type heavy chain constant region Fc. This indicates the fact that the mutation introduced into the CH3 mutation pair has no influence on the interaction between the protein A and the heavy chain constant region.

Also, a purified wild type and the heterodimer antibody including the mutation CH3 domain of 0.1 g were observed in a western blot under non-reducing and reducing conditions (FIGS. 17 and 18). A gel in which SDS-PAGE is performed by the above method was moved to a PVDF film, and a goat anti-human IgG (Sigma) and an anti-goat IgG HRP (SantaCruz) were labeled, detected by a PowerOpti-ECL reagent (Animal Genetics Inc), and analyzed by ImageQuant™ LAS4000 mini (GE Healthcare). Formation of the heterodimer was observed in a western blot. It can be understood from the result that, similar to the result observed by SDS-PAGE (FIG. 16), compared to the E-R variant, the W-VT variant and the knob-into-hole (control group), formation of the homodimer of the EW-RVT and EEW-RVT variant in which two pairs are assembled was inhibited.

It was confirmed in the above experiment that, when the existing interaction applied for homodimer formability inside the interface is removed and a selective space complementary-hydrophobic interaction is added, this strategy relatively further contributes to an increase in heterodimer formability than when a long-range electrostatic interaction is newly added (FIG. 16). Therefore, an SW-WVT variant in which an additional space complementary binding pair (Tyr349Ser:Glu357Trp) is assembled to the W-VT variant was constructed and heterodimer formability was observed (FIG. 19). It was confirmed that the SW-WVT variant has slightly less homodimer formability than the EW-RVT variant, but has heterodimer formability of about 89% due to the observed Fc monomer (Table 3). This is caused by an expression degree difference between heavy chains. If a molar ratio of a plasmid is regulated when transfection is performed, an increase in heterodimer formability can be expected.

Also, the disulfide bridge was introduced into the EW-RVT variant and the SW-WVT variant, and heterodimer formability was compared (FIG. 19). In the EW-RVT variant, a long-range electrostatic interaction by the introduced E-R mutation pair (Lys360Glu:Gln347Arg) is asymmetrically provided to the outside region of the CH3 domain interface. Therefore, in order to introduce the disulfide bridge into an opposite region in which there is no electrostatic interaction, a Tyr349Cys mutation was introduced into the CH3A domain, and a Ser354Cys mutation was introduced into the CH3B domain. When the disulfide bridge is introduced into the SW-WVT variant, in order not to influence space complementary binding introduced by the S-W mutation pair (Tyr349Ser:Glu357W), a Ser354Cys mutation was introduced into the CH3A domain, and a Tyr349Cys mutation was introduced into the CH3B domain. The disulfide bridge was generated at the CH3 domain interface opposite to a position of the S-W mutation pair.

The variant into which the disulfide bridge is introduced has greater heterodimer formability than the variant into which no disulfide bridge is introduced, at about 3% in EW-RVT, and about 9% in SW-WVT (Table 3). It was confirmed that introduction of the disulfide bridge contributes to an increase in heterodimer formability. It was observed by SDS-PAGE that the variant into which the disulfide bridge is introduced has a smaller size than the variant into which no disulfide bridge is introduced. It is determined that this is because the heterodimer has a relatively dense form due to the disulfide bridge under SDS denaturing conditions and thus shows a moving ability difference in PAGE, not because of a real size difference of the heterodimer in a natural state.

Also, the heterodimer in which each mutation is included is repeatedly expressed and purified, and a density of each band in SDS-PAGE was analyzed using an ImageJ program (Wayne Rasband, NIH). As a result, it can be understood that a yield of formation of the heterodimer including the EW-RVT and EEW-RVT mutation is about 90 to 95%, which is higher than that of a knob-into-hole heterodimer (the existing positive control group) yield, i.e., about 85 to 90% (Table 3). In the following [Table 3], heterodimer formability of the heavy chain constant regions including the constructed CH3 domain mutation pair is compared, KiH was used as a control group, and result values were represented as a standard error of mean (mean S.E.M) after the experiment was independently performed three or more times.

TABLE 3

Heterodimer yields (SDS-PAGE result analysis)

| Mutant name | AA Homodimer (CH3A:CH3A) (scFv-Fc)2 | AB Heterodimer (CH3A:CH3B) (scFv-Fc)(Fc) | BB Homodimer (CH3B:CH3B) (Fc)2 | BMonomer (CH3B) Fc |
|---|---|---|---|---|
| E-R | 5.7 ± 2.6 | 52.7 ± 2.3 | 32.0 ± 2.4 | 9.6 ± 3.2 |
| W-VT | ND | 77.3 ± 1.5 | 16.0 ± 1.4 | 6.7 ± 2.8 |
| EW-RVT | 0.5 ± 0.6 | 91.4 ± 1.2 | 1.6 ± 0.6 | 6.6 ± 1.3 |
| EW-RVT (S-S) | 0.6 ± 0.4 | 94.2 ± 0.4 | 2.2 ± 0.4 | 3.0 ± 1.2 |
| EEW-RVT | ND | 90.9 ± 5.7 | 6.3 ± 3.7 | 5.5 ± 2.1 |
| SW-WVT | 0.1 ± 0.1 | 89.2 ± 1.2 | 1.7 ± 0.2 | 9.0 ± 1.1 |
| SW-WVT (S-S) | ND | 98.6 ± 0.8 | 0.8 ± 1.1 | 0.6 ± 0.5 |
| KiH | 4.4 ± 1.8 | 86.4 ± 1.7 | 5.9 ± 1.3 | 3.2 ± 1.1 |

An expression yield of a heterodimer protein including the CH3 domain variant was observed (Table 4). Transient transfection with HEK293 cells was performed, and expression was performed in a culture solution (about 20 ml) for 5 days. A concentration and a volume of the protein upon completion of the purification process were quantified to calculate an expression yield of the protein. The experiment was repeated 3 to 5 times and results were represented as a standard error of mean (mean S.E.M).

The result showed that the heterodimer protein including the CH3 domain variant has a yield that is slightly less than the heterodimer including the wild type CH3 domain and is similar to or slightly greater than the knob-into-hole (control group). Accordingly, it can be determined that the mutation pair introduced into the CH3 domain does not significantly inhibit protein stability, compared to the wild type antibody.

TABLE 4

Total protein yields (scFv-Fc/Fc-heterodimer, HEK293 cell, ~5 days expression)

| Mutant name | Final product after buffer change (mg/culture volume 20 ml) |
|---|---|
| Wild type | 0.33 ± 0.16 |
| E-R | 0.49 ± 0.05 |
| W-VT | 0.14 ± 0.05 |
| EW-RVT | 0.37 ± 0.12 |
| EW-RVT (S-S) | 0.27 ± 0.05 |
| EEW-RVT | 0.44 ± 0.12 |
| SW-WVT | 0.29 ± 0.01 |
| SW-WVT (S-S) | 0.22 ± 0.03 |
| KiH | 0.31 ± 0.08 |

Circular dichroism was measured in order to check whether a protein secondary structure of the CH3 domain including the mutation pair is preserved the same as a protein secondary structure of the wild type CH3 domain. Each of the CH3A domain and the CH3B domain was constructed as a dummy-Fc vector, and an Fc domain dimer was produced and used for analysis (FIG. 14). The Chirascan™ plus spectrometer (Applied Photophysics, UK) was used, and an analysis temperature was 25° C. As a measurement buffer solution, PBS (pH 7.4) was used. Analysis was performed at a range of 195 nm to 260 nm.

As a result, it can be understood that the Fc dimer including the CH3 domain into which the EW-RVT mutation pair is introduced has the same mean residue ellipticity as the Fc dimer including the wild type CH3 domain. This indicates that there is no change in the secondary structure of the protein even when the mutation pair is introduced (FIG. 20).

Also, in order to check whether the antibody including the CH3 domain into which the mutation pair is introduced maintains the binding ability to FcRn compared to the antibody including the wild type CH3 domain, surface plasmon resonance (SPR) was performed. Biacore™ 2000 (GE healthcare, USA) was used. A binding ability to sFcRn (Feng et al., 2011) was analyzed with respect to the heterodimer antibody including the EW-RVT mutation pair CH3 variant and the control group, i.e., Remicade™ (Inflilximab, Janssen Biotech) which is an IgG1 antibody including the wild type CH3 domain. sFcRn was diluted in a 10 mM Na-acetate buffer solution (pH 4.0), and fixed to a CM5 sensor chip (GE healthcare, USA) at about 1000 response units (RU). As a running buffer solution, a PBS (pH 6.0) in which 0.005% of Tween 20 was included and an HBS-EP buffer solution (pH 7.4) were used. The CH3 mutation was analyzed at concentrations of 0.625, 1.25, 2.5, and 5 µM.

As a result, it was confirmed that the antibody including the CH3 domain into which the mutation pair is introduced maintains the binding ability to FcRn, similar to the antibody including the wild type CH3 domain (FIG. 21).

<Example 6> Analysis of Expression and Purification of Anti-DR4xDR5 scFv-Fc Bispecific Antibody Using CH3 Domain Variant in which scFv Form Anti-DR4xDR5 Antibody is Fused A humanized hAY4a scFv antibody (Lee, Park et al. 2010) specifically binding to a target antigen DR4, and an affinity-improved AUSH scFv antibody of a human HW1 scFv antibody (Park, Lee et al. 2007) specifically binding to a target antigen DR5 were fused to the N-terminus of Fc in which the CH3 domain variant is used to construct the bispecific antibody (FIG. 22A).

In this case, the used mutation pair was the EW-RVT pair, the constructed scFv-Fc form bispecific antibody was expressed and purified using the method as in <Example 5>, and a protein was analyzed by SDS-PAGE. It was confirmed that, compared to the scFv-Fc form antibody into which the knob-into-hole is introduced (control group), the scFv-Fc form anti-DR4xDR5 bispecific antibody into which the mutation pair is introduced was purified while being assembled in the form of a dimer or without cut byproducts due to protein instability (FIG. 22B).

Also, in order to measure a binding state of the bispecific antibody, HPLC (The Agilent 1200 Series LC Systems and Modules, Agilent, USA) was used to perform size exclusion chromatography (Superdex 10/300GL, GE Healthcare, Sweden). As an elution buffer solution, PBS (pH 7.4, 137 mM NaCl, 10 mM Phosphate, 2.7 mM KCl, SIGMA-ALDRICH co., USA) was used and a flow rate was 0.5 ml/min. A protein size marker, IgG (150 kD), albumin (66 kDa), and a carbonic anhydrase (29 kDa) protein were used. It was confirmed that, compared to the scFv-Fc form antibody in which the knob-into-hole is introduced (control group), the scFv-Fc form anti-DR4×DR5 bispecific antibody into which the M7 mutation pair is introduced was purified while being assembled in the form of a dimer or without cut byproducts due to protein instability on size exclusion chromatography (FIG. 22C).

<Example 7> Preparation of Anti-DR4×DR5 scFab-Fc Bispecific Antibody Using a CH3 Domain Variant in which an scFab Form Anti-DR4×DR5 Antibody is Fused and Analysis of the Binding Ability to an Antigen of the Bispecific Antibody The prepared CH3 mutation pair was introduced to construct a bispecific antibody in the form of scFab-Fc (scIgG). The used parent antibodies were the humanized hAY4a antibody and the AU5H antibody, which are the same as those in the scFv-Fc form bispecific antibody in <Example 6>. A single chain Fab (scFab) in which a VH-CH domain and a VL-CL domain are connected by 26 amino acid chains was fused to the N-terminus of Fc (FIG. 23A).

In this case, the used mutation pair was the EW-RVT pair. The constructed scFab-Fc form bispecific antibody was expressed and purified using the method as in Example 6, and a protein was analyzed by SDS-PAGE. It was confirmed that, under non-reducing conditions, the scFab-Fc form bispecific antibody into which the mutation pair is introduced was purified mainly as an antibody assembled in the form of a desired bivalent, similar to the bispecific antibody into which the knob-into-hole is introduced (control group), and under reducing conditions, the monomer of the desired bispecific antibody was purified without aggregation or cleavage (FIG. 23B).

In order to measure a bispecific binding ability of the purified Fc variant bispecific antibody, an enzyme linked immunosorbent assay (ELISA) was performed. Target molecules BSA, DR4, and DR5 and the control groups DcR1 and DcR2 were assembled in a 96 well EIA/RIA plate (COSTAR Corning In., USA) at 37° C. for 1 hour, and then washed with 0.1% PBST (0.1% Tween20, pH 7.4, 137 mM NaCl, 10 mM Phosphate, 2.7 mM KCl, SIGMA-ALDRICH co., USA) three times for 10 minutes. The sample was combined with 5% Skim milk (5% Skim milk, pH 7.4, 137 mM NaCl, 10 mM Phosphate, 2.7 mM KCl, SIGMA-ALDRICH co., USA) for 1 hour, and then washed with 0.1% PBST (0.1% Tween20, pH 7.4, 137 mM NaCl, 10 mM Phosphate, 2.7 mM KCl, SIGMA-ALDRICH co., USA) three times for 10 minutes. The purified Fc variant bispecific antibody was assembled and then washed with 0.1% PBST three times for 10 minutes. The sample was combined with alkaline phosphatase-conjugated anti-human mAb (Sigma, USA), and then reacted with pNPP (p-nitrophenyl palmitate, SIGMA-ALDRICH co., USA) and absorbance at 405 nm was measured. According to the ELISA result, it was confirmed that the expressed and purified scFv-Fc form and scFab-Fc form bispecific antibodies have specificity to the target molecules DR4 and DR5, respectively (FIG. 23C). The scFv-Fc form and scFab-Fc form bispecific antibodies into which the mutation pair M7 is introduced had a binding force to the target molecules DR4 and DR5 that is similar to the bispecific antibody into which the knob-into-hole is introduced (control group). Specificity to the target molecules was maintained without cross-reactivity in DcR1 and DcR2. Accordingly, it was confirmed that introduction of the improved CH3 domain mutation pair has no influence on a binding ability of an antigen binding site.

<Example 8> Evaluation of Cytotoxicity of Anti-DR4×DR5 scFv-Fc and scFab-Fc Bispecific Antibody Using CH3 Domain Variant in which Anti-DR4×DR5 Antibody is Fused In order to check a cancer cell killing activity of anti-DR4×DR5 scFv-Fc and scFab-Fc bispecific antibodies prepared in <Example 6> and <Example 7>, a cytotoxicity experiment (MTT assay) was performed on cell lines of a human-derived cancer cell HCT116 (colorectal carcinoma) and HeLa (adenocarcinoma).

Specifically, cancer cell lines were seeded in a 96 well plate at a density of $1 \times 10^4$ cells per well, cultured in 5% $CO_2$ incubator at 37° C. for 1.5 days, and the parent antibodies, anti-DR4 humanized antibody hAY4a IgG and anti-DR5 human antibody AU5H-scFv, prepared scFv-Fc and scFab-Fc form bispecific antibodies, and TNF-related apoptosis inducing ligand (TRAIL) that is a ligand of DR4 and DR5 serving as a positive control group were cultured in an incubator for 20 hours. In this case, the TRAIL expressed and purified in E. coli was used. Then, a treatment of an MTT solution (Sigma) of 5 mg/ml was applied at 20 μl per well, the sample was cultured for 34 hours, the culture solution in the well was removed, formazan was dissolved in DMSO (100 μl), and absorbance of the dissolved formazan was measured at 595 nm to quantify the cytotoxicity.

As a result, it can be understood that the bispecific antibodies of two forms had a greater cancer cell killing activity than the parent antibodies, humanized antibody hAY4a IgG and human antibody AU5H-scFv, and had a cytotoxicity that is similar to or more excellent than the TRAIL used as the positive control group (FIG. 24).

The following Table 5 shows heterodimers of antibody CH3 domains and sequence information of heterodimeric Fc pairs of the present invention.

TABLE 5

| Mutant name | CH3A (EU numbering 341~447) | CH3B (EU numbering 341~447) |
|---|---|---|
| Wild type | (EU number 341) GQPREPQVYTLPPSRDELT KNQVSLTCLVKGFTPSDIAVE WESBGQPENNYKTTPPVLDSD GSFFLYSKLTVDKSRWQQGN VFSCSVMHEALHNHYTQKSLS LSPGK (EU number 447) (SEQ ID NO 1) | (EU number 341) GQPREPQVYTLPPSRDELT KNQVSLTCLVKGFYPSDIAVE WESNGQPENNYKTTPPVLDSD GSFFLYSKLTVDKSRWQQGNV FSCSVMHEALHNHYTQKSLSL SPGK (EU numver 447) (SEQ ID NO 2) |

TABLE 5-continued

| Mutant name | | |
|---|---|---|
| E-R | (EU number 341) GQPREPQVYTLPPSRDELT ENQVSLTCLVKGFYPSDIAVE WESNGQPENNYKTTPPVLDSD GSFFLYSKLTVDKSRWQQGN VFSCSVMHEALHNHYTQKSLS LSPGK (EU number 447) (SEQ ID NO 3) | (EU number 341) GQPREPRVYTLPPSRDELT KNQVSLTCLVKGFYPSDIAVE WESNGQPENNYKTTPPVLDSD GSFFLYSKLTVDKSRWQQGNV FSCSVMHEALHNHYTQKSLSL SPGK (EU number 447) (SEQ ID NO 4) |
| W-VT | (EU number 341) GQPREPQVYTLPPSRDELT KNQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 5) | (EU number 341) GQPREPRVYTLPPSRDELT KNQVSLTCLVKGFYPSDIAVE WESNGQPENNYKTTPPVLDSD GSFTLYSKLTVDKSRWQQGN VFSCSVMHEALHNHYTQKSLS LSPGK (EU number 447) (SEQ ID NO 6) |
| EW-RVT | (EU number 341) GQPREPQVYTLPPSRDELT KNQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 7) | (EU number 341) GQPREPRVYTLPPSRDELT KNQVSLTCLVKGFYPSDIAVE WESNGQPENNYKTTPPVLVSD GSFTLYSKLTVDKSRWQQGN VFSCSVMHEALHNHYTQKSLS LSPGK (EU number 447) (SEQ ID NO 8) |
| EW-RVT (S-S) | (EU number 341) GQPREPQVYTLPPSRDELT ENQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 9) | (EU number 341) GQPREPRVYTLPPCRDELT KNQVSLTCLVKGFYPSDIAVE WESNGQPENNYKTTPPVLVSD GSFTLYSKLTVDKSRWQQGN VFSCSVMHEALHNHYTQKSLS LSPGK (EU number 447) (SEQ ID NO 10) |
| EEW-RVT | (EU number 341) GQPREPEVYTLPPSRDELT ENQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 11) | (EU number 341) GQPREPRVYTLPPCRDELT KNQVSLTCLVKGFYPSDIAVE WESNGQPENNYKTTPPVLVSD GSFTLYSKLTVDKSRWQQGN VFSCSVMHEALHNHYTQKSLS LSPGK (EU number 447) (SEQ ID NO 12) |
| SW-WVT | (EU number 341) GQPREPEVSTLPPSRDELT KNQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 13) | (EU number 341) GQPREPQVYTLPPSRDWL TKNQVSLTCLVKGFYPSDIAV EWESNGQPENNYKTTPPVLVSD GSFTLYSKLTVDKSRWQQGN VFSCSVMHEALHNHYTQKSLS LSPGK (EU number 447) (SEQ ID NO 14) |
| SW-WVT (S-S) | (EU number 341) GQPREPEVSTLPPCRDELT KNQVSLTCLVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 15) | (EU number 341) GQPREPQVCTLPPSRDWL TKNQVSLTCLVKGFYPSDIAV EWESNGQPENNYKTTPPVLVSD GSFTLYSKLTVDKSRWQQGN VFSCSVMHEALHNHYTQKSLS LSPGK (EU number 447) (SEQ ID NO 16) |
| KiH (Genentech) | (EU number 341) GQPREPQVYTLPPCRDELT KNQVSLSCAVKGFYPSDIAVE WESNGQPENNYKTTPPVLDSD GSFFLYSWLTVDKSRWQQGN VFSCSVMHEALHNHYTQKSLS LSPGK (EU number 447) (SEQ ID NO 17) | (EU number 341) GQPREPQVYTLPPSRDEL TKNQVSLWCLVKGFYPSDIAV EWESNGQPENNYKTTPPVLVSD GSFFLYSKLTVDKSRWQQGN VFSCSVMHEALHNHYTQKSLS LSPGK (EU number 447) (SEQ ID NO 18) |

TABLE 5-continued

| Mutant name | Fc (A chain) (EU numbering 225~447) | Fc (B chain) (EU numbering 225~447) |
| --- | --- | --- |
| Wild type | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTKNQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 19) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTKNQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 20) |
| E-R | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTENQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 21) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPRV<br>YTLPPSRDELTKNQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 22) |
| W-VT | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTKNQVSLTCLV<br>KGFYPSDIAVEWESNGQPENN<br>YKTTPPVLDSDGSFFLYSWLTV<br>DKSRWQQGNVFSCSVMHEAL<br>HNHYTQKSLSLSPGK (EU<br>number 447) (SEQ ID NO 23) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTKNQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 24) |
| EW-RVT | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTENQVSLTCLV<br>KGFYPSDIAVEWESNGQPENN<br>YKTTPPVLDSDGSFFLYSWLTV<br>DKSRWQQGNVFSCSVMHEAL<br>HNHYTQKSLSLSPGK (EU<br>number 447) (SEQ ID NO 25) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>YTLPPSRDELTKNQVSLTCLV<br>KGFYPSDIAVEWESNGQPENN<br>YKTTPPVLDSDGSFFLYSKLTV<br>DKSRWQQGNVFSCSVMHEAL<br>HNHYTQKSLSLSPGK (EU<br>number 447) (SEQ ID NO 26) |
| EW-RVT (S-S) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPQV<br>CTLPPSRDELTENQVSLTCLV<br>KGFYPSDIAVEWESNGQPENN<br>YKTTPPVLDSDGSFFLYSWLTV<br>DKSRWQQGNVFSCSVMHEAL<br>HNHYTQKSLSLSPGK (EU<br>number 447) (SEQ ID NO 27) | (EU number 225)<br>TCPPCPAPELLGGPSVFLFP<br>PKPKDTLMISRTPEVTCVVVD<br>VSHEDPEVKFNWYVDGVEVH<br>NAKTKPREEQYNSTYRVVSVL<br>TVLHQDWLNGKEYKCKVSNK<br>ALPAPIEKTISKAKGQPREPRV<br>YTLPPCRDELTKNQVSLTCLV<br>KGFYPSDIAVEWESNGQPENN<br>YKTTPPVLVSDGSFTLYSKLTV<br>DKSRWQQGNVFSCSVMHEAL<br>HNHYTQKSLSLSPGK (EU<br>number 447) (SEQ ID NO 28) |

TABLE 5-continued

| Mutant name | | |
|---|---|---|
| EEW-RVT | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPEV YTLPPSRDELTENQVSLTCLV KGFYPSDIAVEWESNGQPENN YKTTPPVLDSDGSFFLYSWLTV DKSRWQQGNVFSCSVMHEAL HNHYTQKSLSLSPGK (EU number 447) (SEQ ID NO 29) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPRV YTLPPCRDELTKNQVSLTCLV KGFYPSDIAVEWESNGQPENN YKTTPPVLVSDGSFTLYSKLTV DKSRWQQGNVFSCSVMHEAL HNHYTQKSLSLSPGK (EU number 447) (SEQ ID NO 30) |
| SW-WVT | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV STLPPSRDELTKNQVSLTCLV KGFYPSDIAVEWESNGQPENN YKTTPPVLDSDGSFFLYSWLTV DKSRWQQGNVFSCSVMHEAL HNHYTQKSLSLSPGK (EU number 447) (SEQ ID NO 31) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV CTLPPCRDWLTKNQVSLTCLV KGFYPSDIAVEWESNGQPENN YKTTPPVLVSDGSFTLYSKLTV DKSRWQQGNVFSCSVMHEAL HNHYTQKSLSLSPGK (EU number 447) (SEQ ID NO 32) |
| SW-WVT (S-S) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV STLPPCRDELTKNQVSLTCLV KGFYPSDIAVEWESNGQPENN YKTTPPVLDSDGSFFLYSWLTV DKSRWQQGNVFSCSVMHEAL HNHYTQKSLSLSPGK (EU number 447) (SEQ ID NO 33) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV CTLPPSRDWLTKNQVSLTCLV KGFYPSDIAVEWESNGQPENN YKTTPPVLVSDGSFTLYSKLTV DKSRWQQGNVFSCSVMHEAL HNHYTQKSLSLSPGK (EU number 447) (SEQ ID NO 34) |
| KiH (Genentech) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV YTLPPSRDELTKNQVSLSCAV KGFYPSDIAVEWESNGQPENN YKTTPPVLDSDGSFFLYSWLTV DKSRWQQGNVFSCSVMHEAL HNHYTQKSLSLSPGK (EU number 447) (SEQ ID NO 35) | (EU number 225) TCPPCPAPELLGGPSVFLFP PKPKDTLMISRTPEVTCVVVD VSHEDPEVKFNWYVDGVEVH NAKTKPREEQYNSTYRVVSVL TVLHQDWLNGKEYKCKVSNK ALPAPIEKTISKAKGQPREPQV CTLPPSRDWLTKNQVSLTCLV KGFYPSDIAVEWESNGQPENN YKTTPPVLVSDGSFTLYSKLTV DKSRWQQGNVFSCSVMHEAL HNHYTQKSLSLSPGK (EU number 447) (SEQ ID NO 34) |

While the invention has been described with respect to the above specific embodiments, it should be recognized that various modifications and changes may be made to the invention by those skilled in the art which also fall within the scope of the invention as defined by the appended claims.

What is claimed is:

1. A heterodimer comprising a first peptide chain and a second peptide chain, said first peptide chain comprising a first CH3 domain and said second peptide chain comprising a second CH3 domain,
    wherein Lys409 of one of the first and the second CH3 domains is substituted with tryptophan (W), and Asp399 and Phe405 of the other CH3 domain are substituted with valine (V) and threonine (T), respectively
    and
    wherein the positions are numbered according to the EU index.

2. The heterodimer of claim 1, which further comprises the following amino acid substitutions:
    Lys360 of one of the first and the second CH3 domains being substituted with glutamic acid (E), and Gln347 of the other CH3 domain is substituted with arginine (R), and
    wherein the positions are numbered according to the EU index.

3. The heterodimer of claim 2, wherein the first CH3 domain comprises substitutions of Lys360Glu and Lys409Trp and the second CH3 domain comprises substitutions of Gln347Arg, Asp399Val and Phe405Thr.

4. The heterodimer of claim 3, wherein the first CH3 domain further comprises a substitution of Gln347Glu.

5. The heterodimer of claim 1, wherein Tyr349 and Lys409 of one of the first and the second CH3 domains are substituted with serine (S) and tryptophan (W), respectively, and Glu357, Asp399 and Phe405 of the other CH3 domain are substituted with tryptophan (W), valine (V) and threonine (T), respectively.

6. The heterodimer of claim 1, which further comprises the following amino acid substitutions:
    a substitution at at least one position selected from the group consisting of Tyr349 and Ser354 of one of the first and the second CH3 domains with cysteine (C), and
    a substitution at at least one position selected from the group consisting of Tyr349 and Ser354 of the other CH3 domain with cysteine (C),
    wherein the positions are numbered according to the EU index.

7. An immunoglobulin comprising, in its Fc region, the heterodimer of claim 1, wherein the immunoglobulin is selected from the group consisting of IgG1, IgG2, IgG3, IgG4, IgM, IgA, IgD and IgE.

8. A heterodimeric Fc pair protein comprising the heterodimer of claim 1, wherein the first peptide chain further comprises a first CH2 domain and the second peptide chain further comprises a second CH2 domain.

9. A bispecific antibody comprising a heterodimeric Fc pair protein of claim 8, wherein the antibody is selected from the group consisting of scFv-Fc, scIgG(scFab-Fc), (Fv)2-Fc and mAb-Fv forms,
    wherein the scFv-Fc has a structure in which two scFvs, each having a different antigen specificity from the other, are fused to the N-terminus or C-terminus of a heterodimeric Fc pair protein, or
    wherein the scIgG(scFab-Fc) has a structure in which two different scFabs are fused to a heterodimeric Fc pair protein, or
    wherein the (Fv)2-Fc has a structure in which an antigen-binding Fv consisting of a variable region of a heavy chain and an antigen-binding Fv consisting of a variable region of light chain fused to the N-terminus and C-terminus of a heterodimeric Fc pair protein, respectively, or
    wherein the mAb-Fv is a bispecific variable region-fused monoclonal antibody in which a single variable antigen-binding domain of a heavy chain or a single variable antigen-binding domain of a light chain is fused to the C-terminus of IgG heavy chain consisting of a heterodimeric Fc pair protein.

10. A monovalent antigen-binding antibody comprising the heterodimeric Fc pair protein of claim 8, the antibody being in a form of Fv-Fc in which a variable region of heavy chain (VH) and a variable region of light chain (VL), which both bind to a single antigen, are fused to the N-terminus or C-terminus of the heterodimeric Fc pair protein, and
    wherein the monovalent antigen-binding antibody is capable of monovalently binding to the single antigen.

11. A fusion protein comprising at least two proteins and the heterodimeric Fc pair protein of claim 8, wherein the at least two proteins are bound to the N-terminus or the C-terminus of the heterodimeric Fc pair protein.

12. A pharmaceutical composition comprising the heterodimeric Fc pair of claim 8 and a pharmaceutically acceptable carrier.

13. A pharmaceutical composition comprising the bispecific antibody of claim 9 and a pharmaceutically acceptable carrier.

14. A pharmaceutical composition comprising the monovalent antigen-binding antibody of claim 10 and a pharmaceutically acceptable carrier.

15. A pharmaceutical composition comprising the fusion protein of claim 11 and a pharmaceutically acceptable carrier.

16. A method for preparing a heterodimeric Fc pair protein, the method comprising:
   transforming a host cell with the expression vector encoding the heterodimeric Fc pair protein of claim 8;
   culturing the transformed host cell to produce the heterodimeric Fc pair protein of claim 8; and
   purifying and recovering the heterodimeric Fc pair protein.

17. The heterodimer of claim 2, which further comprises the following amino acid substitutions:
   a substitution at at least one position selected from the group consisting of Tyr349 and Ser354 of one of the first and the second CH3 domains with cysteine (C), and
   a substitution at at least one position selected from the group consisting of Tyr349 and Ser354 of the other CH3 domain with cysteine (C),
   wherein the positions are numbered according to the EU index.

18. An immunoglobulin comprising, in its Fc region, the heterodimer of claim 2, wherein the immunoglobulin is selected from the group consisting of IgG1, IgG2, IgG3, IgG4, IgM, IgA, IgD and IgE.

19. A heterodimeric Fc pair protein comprising the heterodimer of claim 2.

20. A bispecific antibody comprising a heterodimeric Fc pair protein, said heterodimeric Fc pair protein comprising the heterodimer of claim 2 and wherein the first peptide chain further comprises a first CH2 domain and the second peptide chain further comprises a second CH2 domain, wherein the antibody is selected from the group consisting of scFv-Fc, scIgG(scFab-Fc), (Fv)2-Fc and mAb-Fv forms,
   wherein the scFv-Fc has a structure in which two scFvs, each having a different antigen specificity from the other, are fused to the N-terminus or C-terminus of a heterodimeric Fc pair protein, or
   wherein the scIgG(scFab-Fc) has a structure in which two different scFabs are fused to a heterodimeric Fc pair protein, or
   wherein the (Fv)2-Fc has a structure in which an antigen-binding Fv consisting of a variable region of a heavy chain and an antigen-binding Fv consisting of a variable region of light chain re fused to the N-terminus and C-terminus of a heterodimeric Fc pair protein, respectively, or
   wherein the mAb-Fv is a bispecific variable region-fused monoclonal antibody in which a single variable antigen-binding domain of a heavy chain or a single variable antigen-binding domain of a light chain is fused to the C-terminus of IgG heavy chain consisting of a heterodimeric Fc pair protein.

21. A monovalent antigen-binding antibody comprising the heterodimeric Fc pair protein of claim 19, the antibody being in a form of Fv-Fc in which a variable region of heavy chain (VH) and a variable region of light chain (VL), which both bind to a single antigen, are fused to the N-terminus or C-terminus of the heterodimeric Fc pair protein, and
   wherein the monovalent antigen-binding antibody is capable of monovalently binding to the single antigen.

22. A fusion protein comprising at least two proteins and the heterodimeric Fc pair protein of claim 19, wherein the at least two proteins are bound to the N-terminus or the C-terminus of the heterodimeric Fc pair protein.

23. A pharmaceutical composition comprising the heterodimeric Fc pair of claim 19 and a pharmaceutically acceptable carrier.

24. A pharmaceutical composition comprising the bispecific antibody of claim 20 and a pharmaceutically acceptable carrier.

25. A pharmaceutical composition comprising the monovalent antigen-binding antibody of claim 21 and a pharmaceutically acceptable carrier.

26. A pharmaceutical composition comprising the fusion protein of claim 22 and a pharmaceutically acceptable carrier.

* * * * *